US009889568B2

(12) United States Patent
Kilroy et al.

(10) Patent No.: US 9,889,568 B2
(45) Date of Patent: Feb. 13, 2018

(54) COMPACT ROBOTIC WRIST

(71) Applicant: SRI INTERNATIONAL, Menlo Park, CA (US)

(72) Inventors: Pablo Eduardo Garcia Kilroy, Menlo Park, CA (US); Kenneth C. Miller, Aptos, CA (US); Thomas D. Egan, Marblehead, MA (US); Thomas P. Low, Belmont, CA (US); Arthur Maxwell Crittenden, Menlo Park, CA (US); Karen Shakespear Koenig, San Francisco, CA (US)

(73) Assignee: SRI International, Menlo Park, CA (US)

( * ) Notice: Subject to any disclaimer, the term of this patent is extended or adjusted under 35 U.S.C. 154(b) by 569 days.

(21) Appl. No.: 14/388,208

(22) PCT Filed: Mar. 13, 2014

(86) PCT No.: PCT/US2014/026721
§ 371 (c)(1),
(2) Date: Sep. 25, 2014

(87) PCT Pub. No.: WO2014/151952
PCT Pub. Date: Sep. 25, 2014

(65) Prior Publication Data
US 2015/0150635 A1 Jun. 4, 2015

Related U.S. Application Data

(60) Provisional application No. 61/781,092, filed on Mar. 14, 2013, provisional application No. 61/791,248, filed on Mar. 15, 2013.

(51) Int. Cl.
*A61B 17/00* (2006.01)
*B25J 17/02* (2006.01)
(Continued)

(52) U.S. Cl.
CPC .............. *B25J 17/02* (2013.01); *A61B 17/29* (2013.01); *A61B 34/30* (2016.02); *A61B 34/71* (2016.02);
(Continued)

(58) Field of Classification Search
CPC ............ A61B 17/29; A61B 2017/2908; A61B 2017/2927; A61B 2017/2929;
(Continued)

(56) References Cited

U.S. PATENT DOCUMENTS 4,843,921 A  7/1989 Kremer
5,339,723 A  8/1994 Huitema
(Continued)

FOREIGN PATENT DOCUMENTS

CN  102143714 A  8/2011
EP  2415418 A1  2/2012
(Continued)

OTHER PUBLICATIONS

Supplemental Partial European Search Report dated Mar. 9, 2016 in EP Application No. 14770569.
(Continued)

*Primary Examiner* — Ashley Fishback
(74) *Attorney, Agent, or Firm* — Cooley LLP

(57) ABSTRACT

A surgical tool includes a tool shaft, and end effector and a wrist that couples the end effector to the tool shaft. The tool includes a drive mechanism configured to effect movement of one or both of the wrist and the end effector in yaw and pitch via independent actuation of four independent cable ends of two or more independent cables that extend between the drive mechanism and the wrist.

17 Claims, 43 Drawing Sheets

(51) Int. Cl.
*A61B 17/29* (2006.01)
*B25J 15/00* (2006.01)
*B25J 15/02* (2006.01)
*A61B 34/30* (2016.01)
*A61B 34/00* (2016.01)

(52) U.S. Cl.
CPC ....... B25J 15/0028 (2013.01); B25J 15/0286 (2013.01); *A61B 2017/2938* (2013.01); *A61B 2034/305* (2016.02); *A61B 2034/306* (2016.02); *A61B 2034/715* (2016.02); *Y10S 901/29* (2013.01); *Y10S 901/36* (2013.01); *Y10S 901/38* (2013.01)

(58) Field of Classification Search
CPC .............. A61B 34/71; A61B 2034/305; A61B 2034/306; A61B 2034/715; B25J 15/0028; B25J 15/0286
See application file for complete search history.

(56) References Cited

U.S. PATENT DOCUMENTS

| | | |
|---|---|---|
| 5,720,742 A | 2/1998 | Zacharias |
| 5,855,583 A | 1/1999 | Wang et al. |
| 6,270,508 B1 | 8/2001 | Klieman et al. |
| 6,331,181 B1 | 12/2001 | Tierney et al. |
| 6,450,978 B1 | 9/2002 | Brosseau et al. |
| 6,451,027 B1 | 9/2002 | Cooper et al. |
| 6,459,926 B1 | 10/2002 | Nowlin et al. |
| 6,471,642 B1 | 10/2002 | Igarashi |
| 6,490,490 B1 | 12/2002 | Uchikubo et al. |
| 6,491,701 B2 | 12/2002 | Tierney et al. |
| 6,522,906 B1 | 2/2003 | Salisbury et al. |
| 6,535,756 B1 | 3/2003 | Simon et al. |
| 6,582,358 B2 | 6/2003 | Akui et al. |
| 6,587,750 B2 | 7/2003 | Gerbi et al. |
| 6,608,628 B1 | 8/2003 | Ross et al. |
| 6,659,939 B2 | 12/2003 | Moll et al. |
| 6,669,635 B2 | 12/2003 | Kessman et al. |
| 6,682,478 B2 | 1/2004 | Nakamura |
| 6,793,625 B2 | 9/2004 | Cavallaro et al. |
| 6,799,065 B1 | 9/2004 | Niemeyer |
| 6,892,090 B2 | 5/2005 | Verard et al. |
| 6,951,535 B2 | 10/2005 | Ghodoussi et al. |
| 6,962,581 B2 | 11/2005 | Thoe |
| 6,995,744 B1 | 2/2006 | Moore et al. |
| 7,008,362 B2 | 3/2006 | Fitzgibbon |
| 7,012,203 B2 | 3/2006 | Hanson et al. |
| 7,046,270 B2 | 5/2006 | Murata et al. |
| 7,048,745 B2 | 5/2006 | Tierney et al. |
| 7,076,286 B2 | 7/2006 | Mizoguchi et al. |
| 7,101,334 B2 | 9/2006 | Takahashi |
| 7,106,479 B2 | 9/2006 | Roy et al. |
| 7,206,627 B2 | 4/2007 | Abovitz et al. |
| 7,217,269 B2 | 5/2007 | Ei-Galley et al. |
| 7,277,120 B2 | 10/2007 | Gere et al. |
| 7,317,955 B2 | 1/2008 | McGreevy |
| 7,319,466 B1 | 1/2008 | Tarr et al. |
| 7,369,116 B2 | 5/2008 | Logue |
| 7,379,790 B2 | 5/2008 | Toth et al. |
| 7,417,665 B2 | 8/2008 | Banju et al. |
| 7,498,532 B2 | 3/2009 | Kuhner et al. |
| 7,524,320 B2 | 4/2009 | Tierney et al. |
| 7,671,888 B2 | 3/2010 | Nogami et al. |
| 7,683,926 B2 | 3/2010 | Schechterman et al. |
| 7,768,702 B2 | 8/2010 | Hirose et al. |
| 7,781,941 B2 | 8/2010 | Horvath et al. |
| 7,783,133 B2 | 8/2010 | Dunki-Jacobs et al. |
| 7,789,874 B2 | 9/2010 | Yu et al. |
| 7,789,875 B2 | 9/2010 | Brock et al. |
| 7,806,891 B2 | 10/2010 | Nowlin et al. |
| 7,840,042 B2 | 11/2010 | Kriveshko et al. |
| 7,843,158 B2 | 11/2010 | Prisco |
| 7,865,266 B2 | 1/2011 | Moll et al. |
| 7,883,458 B2 | 2/2011 | Hamel |
| 7,907,166 B2 | 3/2011 | Lamprecht et al. |
| 7,947,050 B2 | 5/2011 | Lee et al. |
| 7,955,322 B2 | 6/2011 | Devengenzo et al. |
| 7,979,157 B2 | 7/2011 | Anvari |
| 7,983,793 B2 | 7/2011 | Toth et al. |
| 8,004,229 B2 | 8/2011 | Nowlin et al. |
| 8,062,288 B2 | 11/2011 | Cooper et al. |
| 8,079,950 B2 | 12/2011 | Stern et al. |
| 8,086,008 B2 | 12/2011 | Coste-Maniere et al. |
| 8,095,200 B2 | 1/2012 | Quaid et al. |
| 8,118,805 B2 | 2/2012 | Jinno et al. |
| 8,126,114 B2 | 2/2012 | Naylor et al. |
| 8,131,031 B2 | 3/2012 | Lloyd |
| 8,142,447 B2 | 3/2012 | Cooper et al. |
| 8,147,503 B2 | 4/2012 | Zhao et al. |
| 8,155,479 B2 | 4/2012 | Hoffman et al. |
| 8,190,238 B2 | 5/2012 | Moll et al. |
| 8,206,406 B2 | 6/2012 | Orban et al. |
| 8,256,319 B2 | 9/2012 | Cooper et al. |
| 8,284,234 B2 | 10/2012 | Bjelkhagen et al. |
| 8,332,072 B1 | 12/2012 | Schaible et al. |
| 8,398,541 B2 | 3/2013 | DiMaio et al. |
| 8,469,947 B2 | 6/2013 | Devengenzo et al. |
| 8,473,031 B2 | 6/2013 | Nixon et al. |
| 8,504,136 B1 | 8/2013 | Sun et al. |
| 8,506,555 B2 | 8/2013 | Morales |
| 8,508,173 B2 | 8/2013 | Goldberg et al. |
| 8,521,331 B2 | 8/2013 | Itkowitz |
| 8,527,094 B2 | 9/2013 | Kumar et al. |
| 8,562,594 B2 | 10/2013 | Cooper et al. |
| 8,594,841 B2 | 11/2013 | Zhao et al. |
| 8,600,551 B2 | 12/2013 | Itkowitz et al. |
| 8,634,957 B2 | 1/2014 | Toth et al. |
| 8,638,056 B2 | 1/2014 | Goldberg et al. |
| 8,648,896 B2 | 2/2014 | Takahashi |
| 8,672,922 B2 | 3/2014 | Loh et al. |
| 8,682,489 B2 | 3/2014 | Itkowitz et al. |
| 8,706,184 B2 | 4/2014 | Mohr et al. |
| 8,712,115 B2 | 4/2014 | Kirchberg et al. |
| 8,747,288 B2 | 6/2014 | Strotzer et al. |
| 8,749,190 B2 | 6/2014 | Nowlin et al. |
| 8,761,337 B2 | 6/2014 | Naylor et al. |
| 8,806,359 B2 | 8/2014 | Garibaldi et al. |
| 8,828,023 B2 | 9/2014 | Neff et al. |
| 8,831,782 B2 | 9/2014 | Itkowitz |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,989,903 B2 | 3/2015 | Weir et al. |
| 8,996,173 B2 | 3/2015 | Itkowitz et al. |
| 9,002,517 B2 | 4/2015 | Bosscher et al. |
| 9,026,247 B2 | 5/2015 | White et al. |
| 9,068,824 B2 | 6/2015 | Findeisen et al. |
| 9,101,267 B2 | 8/2015 | Umasuthan et al. |
| 9,108,318 B2 | 8/2015 | Diolaiti |
| 9,129,422 B2 | 9/2015 | Mountney et al. |
| 9,138,135 B2 | 9/2015 | Oderwald et al. |
| 9,161,681 B2 | 10/2015 | Galstian et al. |
| 9,179,980 B2 | 11/2015 | Yoon |
| 9,192,286 B2 | 11/2015 | Kazakevich et al. |
| 9,198,731 B2 | 12/2015 | Balaji et al. |
| 9,215,293 B2 | 12/2015 | Miller |
| 9,221,172 B2 | 12/2015 | Williamson et al. |
| 9,232,984 B2 | 1/2016 | Guthart et al. |
| 9,241,768 B2 | 1/2016 | Sandhu et al. |
| 9,254,078 B2 | 2/2016 | McDowall |
| 9,254,572 B2 | 2/2016 | Strotzer |
| 9,256,936 B2 | 2/2016 | Jacobs et al. |
| 9,259,276 B2 | 2/2016 | Mintz et al. |
| 9,259,282 B2 | 2/2016 | Azizian et al. |
| 9,345,544 B2 | 5/2016 | Hourtash et al. |
| 2002/0082612 A1 | 6/2002 | Moll et al. |
| 2004/0106916 A1 | 6/2004 | Quaid et al. |
| 2004/0199147 A1 | 10/2004 | Nishizawa et al. |
| 2004/0243147 A1 | 12/2004 | Lipow |
| 2007/0049435 A1 | 3/2007 | Jinno et al. |
| 2008/0046122 A1* | 2/2008 | Manzo .............. A61B 1/00149 700/245 |

(56) References Cited

U.S. PATENT DOCUMENTS

| | | |
|---|---|---|
| 2008/0154246 A1 | 6/2008 | Nowlin et al. |
| 2009/0192519 A1 | 7/2009 | Omori |
| 2010/0004663 A1 | 1/2010 | Murphy et al. |
| 2010/0016852 A1 | 1/2010 | Manzo et al. |
| 2010/0175701 A1 | 7/2010 | Reis et al. |
| 2010/0198253 A1 | 8/2010 | Jinno et al. |
| 2011/0118752 A1 | 5/2011 | Itkowitz et al. |
| 2012/0130399 A1 | 5/2012 | Moll et al. |
| 2012/0277663 A1 | 11/2012 | Millman et al. |
| 2012/0316681 A1 | 12/2012 | Hagn et al. |
| 2013/0063580 A1 | 3/2013 | Ogawa et al. |
| 2014/0100588 A1 | 4/2014 | Blumenkranz et al. |
| 2014/0171965 A1 | 6/2014 | Loh et al. |
| 2014/0188131 A1 | 7/2014 | Toth et al. |
| 2015/0025549 A1 | 1/2015 | Kilroy et al. |
| 2015/0038981 A1 | 2/2015 | Kilroy et al. |
| 2015/0038982 A1 | 2/2015 | Kilroy et al. |
| 2015/0157410 A1 | 6/2015 | Kilroy et al. |
| 2015/0209965 A1 | 7/2015 | Low et al. |
| 2015/0321355 A1 | 11/2015 | Kishi |

FOREIGN PATENT DOCUMENTS

| | | |
|---|---|---|
| GB | 2523224 | 8/2015 |
| WO | WO-2010/009223 A2 | 1/2010 |
| WO | WO-2010/009223 A3 | 1/2010 |
| WO | WO 2011/060185 | 5/2011 |
| WO | WO2014084408 | 6/2014 |
| WO | WO 2014/151621 | 9/2014 |
| WO | WO 2014/151952 | 9/2014 |

OTHER PUBLICATIONS

Supplemental European Search Report dated Mar. 10, 2016 in EP Application No. 14767688.
Supplemental European Search Reportdated Jun. 29, 2016 in EP Application No. 14770569.
International Search Report and Written Opinion dated Aug. 18, 2014 in PCT Application No. PCT/US2014/026721.
International Search Report and Written Opinion dated Nov. 2, 2015 in PCT Application No. PCT/US2015/042991.
International Search Report and Written Opinion dated Jan. 7, 2016 in PCT Application No. PCT/US2015/052354.
International Search Report and Written Opinion dated Aug. 21, 2014 in PCT Application No. PCT/US2014/026115.
International Preliminary Report on Patentability dated Sep. 15, 2015 in PCT Application No. PCT/US2014/026115.
International Preliminary Report on Patentability dated Sep. 15, 2015 in PCT Application No. PCT/US2014/026721.
Non-Final Office Action dated Mar. 22, 2017, for U.S. Appl. No. 14/677,509, filed Apr. 2, 2015, 11 pages.

* cited by examiner

Top View (cable 760B)

Bottom View (cable 760B)

Top View (Cable 760A)

Bottom View (Cable 760A)

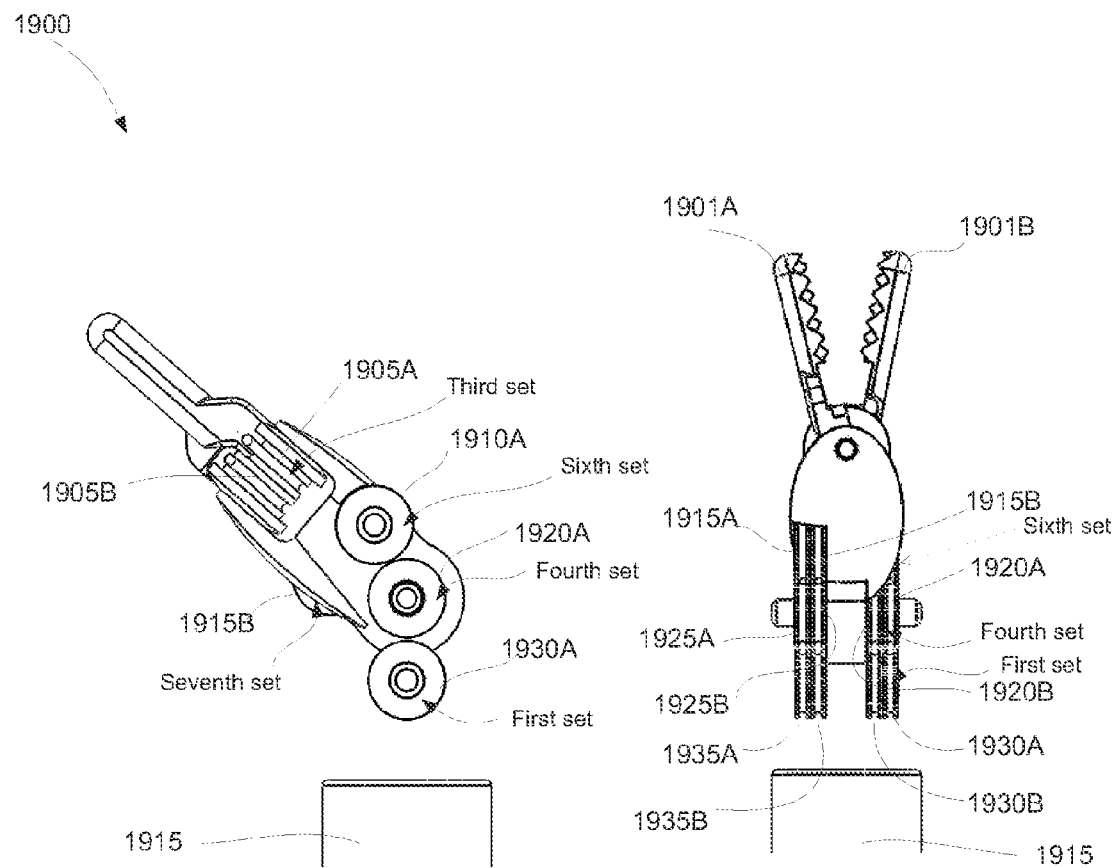

COMPACT ROBOTIC WRIST

INCORPORATION BY REFERENCE TO ANY PRIORITY APPLICATIONS

This application is a U.S. National Stage Application under 35 U.S.C. § 371 of International Application PCT/US2014/026721 filed Mar. 13, 2014, which claims the priority benefit under 35 U.S.C. § 119(e) of U.S. Provisional Application No. 61/781,092 filed Mar. 14, 2013, and U.S. Provisional Application No. 61/791,248 filed Mar. 15, 2013, all of which are hereby incorporated by reference in their entirety and should be considered a part of this specification.

STATEMENT REGARDING FEDERALLY SPONSORED R&D

This invention was made with Government support under Government contract number HSHQDC-10-C-00118, awarded by the Department of Homeland Security. The Government has certain rights in this invention.

BACKGROUND

Field

Robotic end effectors allow robots to manipulate objects. The present application relates to robotic tools, end effectors of the tools, and methods of operating the same.

Description of the Related Art

Robots are used for various purposes including industrial, research, medical and non-medical purposes. Each different type of robot may have its own set of unique features and characteristics in addition to features and characteristics that are common among most robots. One common characteristic of most robots is the use of tools. Tools controlled by robots are used to perform a variety of tasks. Each tool controlled by a robot may be specially designed for the task to be performed. Typically, robotic tools are elongate in shape and have an end effector (e.g., grasper).

With respect to surgical systems, typical on-market robotic systems use straight rigid tools or flexible tools (e.g., curved tools) controlled by cables or other mechanisms. Straight rigid tools are insufficient in some surgical settings, for example when an organ or anatomical structure is between the incision point or port (e.g., the location the tool enters into the body) and the tissue to be operated upon, because the straight shaft is unable to reach around the organ or anatomical structure to access the tissue. Another deficiency of straight rigid tools is that they are not well suited for use in what is referred to as single port surgery, where more than one tool is introduced through a single surgical incision or port, which is sometimes desirable to limit trauma to the patient. In such single port surgeries, cooperative interaction between the multiple tools is needed for tasks such as suturing. To interact cooperatively, the tools need to converge on the operative space from different angles, which straight rigid tools are not well suited for.

With respect to flexible tools, such as curved or bent tools, these tools overcome some of the access and maneuverability issues of straight rigid tools discussed above, but also have deficiencies. One shortcoming of flexible tools is that they typically are not rigid enough to resist bending loads during surgical procedures. Commonly, to improve rigidity, the curved or bent profile of the tools is pre-formed outside the body, either by the manufacturer or by the user using a bending tool, and is therefore unable to be bent within the body to accommodate operative geometry in situ. Other flexible tools are available that are segmented or have flexible shafts, and can be controlled for example by cables. These flexible tools also have shortcomings, such as being unable to achieve sufficient rigidity to withstand bending loads once bent during a surgical procedure.

Straight rigid tools and curved or bent tools are also used in non-medical applications and have the same deficiencies noted above when used in said non-medical applications.

SUMMARY

Accordingly, there is a need for improved robotic tools and end effectors that address the deficiencies noted above with on-market tools. There is a need for improved robotic tools and end effectors that provide for less occlusion of a worksite, enhanced ability to perform complex operations, and enhanced ability to work in areas where access is limited, relative to on-market robotic tools.

In accordance with one aspect of the invention, a tool is provided with a wrist coupled to an end effector. The wrist can include four independent cable ends. The four independent cable ends can be arranged such that each independent cable end may be driven independently. In one embodiment, the four independent cable ends are defined by four independent cables. In another embodiment, the four independent cable ends are defined by two cables, where each end of each cable defines an independent cable end.

The tool can be arranged in one embodiment such that it includes four motors to control each cable end independently.

In accordance with one aspect of the invention, a tool with a wrist coupled to an end effector can have one or more twisted strings instead of cables. A single string may be arranged to behave like a twisted string. The tool can have one or more twisted strings that drive the end effector.

The tool with the wrist and end effector can be arranged to have three or more sets of pulleys. Each cable can be arranged such that each cable winds around the three or more sets of pulleys in two orthogonal directions. Each cable can be arranged such that the relative tension between the two sides of each cable may result in a yaw motion. Each cable can be arranged such that the relative tension between two cables may result in a pitch motion.

The tool with the wrist and end effector can be arranged to have three sets of pulleys and two additional sets of pulleys. Each cable can be arranged such that each cable winds around the three sets of pulleys in two orthogonal directions. The two additional sets of pulleys can be angled relative to the three sets of pulleys. The two additional sets of pulleys can be arranged between the three sets of pulleys.

In accordance with one aspect of the invention, three sets of pulleys are provided and three additional sets of pulleys are provided. Each cable can be arranged such that each cable winds around the three sets of pulleys in two orthogonal directions. The three additional sets of pulleys can be arranged between the three sets of pulleys. The two sets of pulleys and the two additional sets of pulleys can be arranged in first direction, and the one set of pulleys and the one additional set of pulleys can be arranged an orthogonal direction to the first direction.

In accordance with one aspect of the invention, three sets of pulleys are provided and two additional sets of pulleys are provided. Each cable can be arranged such that each cable winds around the three sets of pulleys in two orthogonal directions. The two additional sets of pulleys can be arranged between the three sets of pulleys. The two sets of pulleys and the two additional sets of pulleys can be arranged in first direction, and the one set of pulleys can be arranged an orthogonal direction to the first direction.

The tool can be arranged such that the two cable loops are controlled with three motors. The third motor can be arranged to control a mechanism. The mechanism can be arranged such that the mechanism applies tension to both sides of the same cable. The mechanism can be arranged such that the mechanism enables a pitch motion.

The tool can be arranged such that the mechanism is a rocker member that increases the tension on one cable relative to a tension on another cable. The rocker mechanism can be arranged such that the rocker mechanism rotates (e.g., rocks back and forth) about an axis to move one pulley distally and one pulley proximally to thereby increase tension on one of the two cables and relax tension on the other of the two cables.

The tool can be arranged such that the mechanism is a shuttle mechanism that increases the tension on one cable relative to a tension on another cable. The shuttle mechanism can be arranged to linearly translate along the axis of the tool shaft to move the orientation of shuttle pulleys to thereby increase the distance one cable must travel relative to the distance the other cable must travel. The shuttle mechanism can be arranged such that the motion of the shuttle mechanism applies tension to one of the two cables and relaxes tension on the other of the two cables.

In accordance with another aspect of the invention, a tool has a wrist coupled to an end effector. The wrist can include one or more vertebra, where each vertebra is controllable with one or more independent cables. The one or more cables can be arranged to affect a bend in yaw and pitch. The tool can be arranged such that each vertebra is controllable with two or more cables, where the two or more cables can be arranged to affect a bend in yaw and pitch.

In accordance with another aspect of the invention, a tool is provided that includes one or more rigid sections and one or more flexible sections. The one or more flexible sections can be controllable and selectively locked and unlocked, for example in a bent configuration.

The tool with one or more rigid sections and one or more flexible sections can be arranged such that the one or more flexible sections are passively controlled. The one or more flexible sections can be passively controlled by one or more vertebra. In one embodiment the one or more flexible sections can be controlled by one or more vertebra to rigidize a sheath of the tool to, for example, provide a joint proximal of a wrist of the tool. The joint and wrist can provide redundant mechanisms to effect a motion of the distal end of the tool (e.g., the end effector of the tool). In one embodiment, a configuration (e.g., position, angle) of the joint can be controlled by the same mechanism that controls the actuation of the wrist distal of the joint. In one embodiment, the mechanism can be a locking mechanism, such as one employing a low melting point solid. In another embodiment, the mechanism can be a set of cables actuated to effect movement of the wrist and the joint proximal of the wrist.

The tool with one or more rigid sections and one or more flexible sections can be arranged such that the one or more flexible sections are actively controlled. The one or more flexible sections can be actively controlled by one or more cables. In one embodiment, the one or more flexible sections can be actively controlled by two or more cables.

The tool with one or more rigid sections and one or more flexible sections can be arranged such that the one or more flexible sections are selectively locked with a locking mechanism. The locking mechanism can be arranged to include a low melting point solid. In one embodiment, the melting point solid can be a polymer. The one or more flexible sections can be arranged to include a sheath. The sheath can include a braid of conductive material with filaments impregnated with a matrix of said low melting point solid that can change state from solid to liquid. The locking mechanism can include an activating element actuatable such that the low melting point solid becomes pliable, thereby allowing the one or more flexible sections to bend. The locking mechanism can be arranged so that the activating element includes a heater and/or heater wires. In other embodiments, rigidizing mechanisms based on electrostatic effect or magnetic effects may be used instead of, or in addition to, using low melting point solids.

The tool with one or more rigid sections and one or more flexible sections can be arranged such that the one or more flexible sections can include one or more sensors. The one or more sensors can be one or more strain sensors, one or more position sensors, and/or one or more pressure sensors.

The tool with one or more rigid sections and one or more flexible sections can be arranged such that the one or more flexible sections can be monitored. In one embodiment, the one or more flexible sections can be monitored on a periodic basis. In another embodiment, the one or more flexible sections can be monitored on a continuous basis. The one or more flexible sections can be monitored by one or more cameras. The cameras can be endoscopic cameras. The one or more cameras can produce images, and the images can be processed to obtain the bend parameters of the tool and/or wrist. The bend parameters can further inform the user and/or the control system of a system regarding the control of the tool, such that once the location of the bends are known, this information can be fed into a control loop of the control system to control the tool.

In accordance with another aspect of the invention, a tool has a wrist coupled to an end effector, where one or more cables control the wrist and the end effector. The end effector is arranged such that the one or more cables that control end effector are independent from the one or more cables that control the wrist.

The wrist can include three sets of pulleys. The first set of pulleys can include four pulleys. The four pulleys can be arranged in two sets of two pulleys. In one embodiment, the four pulleys can be arranged so that the first set of two pulleys is parallel to the second set of two pulleys. The second set of pulleys is arranged such that the second set of pulleys is angled relative to the first set of pulleys. The third set of pulleys is arranged such that the third set of pulleys is orthogonal to the first set of pulleys. The third set of pulleys can be coupled to the end effector.

The wrist can include three sets of pulleys. The first set of pulleys can include four pulleys. The four pulleys can be arranged in two sets of two pulleys. The four pulleys can be arranged parallel in two sets of two pulleys. The second set of pulleys is arranged such that the second set of pulleys is not angled relative to the first set of pulleys. The third set of pulleys is arranged such that the third set of pulleys is not orthogonal to the first set of pulleys. The third set of pulleys is arranged such that the third set of pulleys is not orthogonal to the second set of pulleys. The third set of pulleys is arranged such a cable from the second set of pulleys follows a straight path to the third set of pulleys to thereby minimize friction between the cable and pulleys.

The tool with the wrist and end effector can be arranged to have three sets of pulleys and two additional sets of pulleys. The two sets of pulleys and the two additional sets of pulleys can be arranged in first direction, and the one set of pulleys can be arranged in another direction, angled to the first direction. The two additional sets of pulleys can be arranged between the three sets of pulleys. The third set of pulleys is arranged such that a cable from the two additional sets follows a straight path to the third set of pulleys to thereby minimize friction between the cable and pulleys.

The tool with the wrist and end effector can be arranged to have three sets of pulleys and three additional sets of pulleys. The two sets of pulleys and the two additional sets of pulleys can be arranged in first direction, and the one set of pulleys and the one additional set of pulleys can be arranged in an orthogonal direction to the first direction. The three additional sets of pulleys can be arranged between the three sets of pulleys. The two additional sets of pulleys arranged in first direction can have pulleys with offset centers of rotation. The two additional sets of pulleys arranged in first direction can have pulleys with different diameters.

The tool with the wrist and end effector can be arranged to have three sets of pulleys and four additional sets of pulleys. The two sets of pulleys and the four additional sets of pulleys can be arranged in first direction, and the one set of pulleys can be arranged in an orthogonal direction to the first direction. The four additional sets of pulleys can be arranged between the three sets of pulleys. The center of rotation of the first additional set of pulleys is offset from the center of rotation of the second additional set of pulleys. The center of rotation of the third additional set of pulleys is aligned with the center of rotation of the fourth additional set of pulleys.

In accordance with one aspect, a minimally-invasive surgical tool is provided. The tool comprises a tool shaft, an end effector and a multi-axial wrist disposed between the tool shaft and the end effector, the wrist comprising three or more sets of pulleys arranged in two orthogonal directions. The tool further comprises a drive mechanism comprising four electric motors configured to effect movement of one or both of the wrist and the end effector. Each of the four electric motors is configured to independently control one of four independent cables that wind at least partially around one or more of the three or more sets of pulleys. The motors are configured to vary relative tension between the four independent cables to effect a yaw or pitch motion.

In accordance with another aspect, a minimally-invasive surgical tool is provided. The tool comprises a tool shaft, an end effector and a multi-axial wrist disposed between the tool shaft and the end effector, the wrist comprising three or more sets of pulleys arranged in two orthogonal directions. The tool further comprises a drive mechanism configured to effect movement of one or both of the wrist and the end effector. The drive mechanism is configured to independently control four independent cables that wind at least partially around one or more of the three or more sets of pulleys to vary relative tension between the four independent cables to effect a yaw or pitch motion.

In accordance with another aspect, a minimally-invasive surgical tool is provided. The tool comprises a tool shaft, an end effector and a multi-axial wrist disposed between the tool shaft and the end effector, the wrist comprising three or more sets of pulleys arranged in two orthogonal directions. The tool further comprises a drive mechanism comprising three electric motors configured to effect movement of one or both of the wrist and the end effector. The drive mechanism is configured to independently control two cable loops that wind at least partially around one or more of the three or more sets of pulleys to vary relative tension between the two cable loops and between two ends of each cable loop to effect a yaw or pitch motion. One of the three motors is coupled to a mechanism configured to tension two sides of the same cable loop to effect a pitch motion.

In accordance with another aspect, a minimally-invasive surgical tool is provided. The tool comprises a tool shaft, an end effector and a multi-axial wrist disposed between the tool shaft and the end effector, the wrist comprising three or more sets of pulleys arranged in two orthogonal directions. The tool further comprises means for effecting movement of one or both of the wrist and the end effector via independent control of four independent cables that wind at least partially around one or more of the three or more sets of pulleys to vary relative tension between the four independent cables to effect a yaw or pitch motion.

BRIEF DESCRIPTION OF THE DRAWINGS

FIG. 18B illustrates the tool of FIG. 18A.

FIG. 18C illustrates the tool of FIG. 18A.

DETAILED DESCRIPTION

Described below are embodiments of tools, such as surgical tools, that have various advantages over on-market tools. At least some of the embodiments of tools described herein advantageously provide for less occlusion of the worksite, thereby allowing the operator improved visualization of the worksite. At least some of the embodiments of tools described herein provide for enhanced ability (e.g., of an operator of the tool, of a surgeon operating a tool) to perform complex operations by, for example, reducing the diameter of the wrist of the tool. At least some embodiments of tools describe herein provide enhanced ability to work in areas where access is limited (e.g., a smaller workspace), which can be made possible at least in part by a reduction in the diameter of the wrist of the tool.

In some embodiments disclosed below, a tool can include an end effector coupled to a tool shaft via a wrist, where the wrist allows for multi-axial motion (e.g., movement in pitch and yaw). The size of the wrist may be advantageously optimized by using a reduced number of cables to affect the control of the end effector of the tool. Tools so optimized can be used, for example, in minimally invasive surgical procedures due to such a feature of the wrist. However it should be understood that a general wrist described below can also be used in la large number of non-surgical and non-medical applications.

In several of the embodiments described below, the motion of the wrist and/or end effector of the tool is controlled by controlling four cable ends, which provides several advantages. One advantage is a reduction of the number of cables that extend to the wrist of the tool, which allows for minimizing the size and complexity of the mechanical assembly of the wrist. Another advantage is that the four cable arrangement allows independent control of tension on each cable of the wrist, without the need for pre-tensioning of the cables and the resulting friction in the joints of the tool wrist. The independent control of tension of each cable also enables variable compliance in the joints of the wrist and increased sensitivity to external loads. The independent control of tension of the cables further allows increased robustness to wear of the tool since tension can be readjusted. Further, the independent control of the tension of each cable allows the use of non-linear transmissions such as twisted strings since each cable can change length in different amounts. Independent control of each cable additionally enables wrist designs that do not require the sum of all cable lengths to be constant over the range of motion of the wrist, as is required when using fixed cable loops. Other advantages of the tools described herein will become apparent to persons of skill in the art based on the detailed description provided below.

Figure 1A:
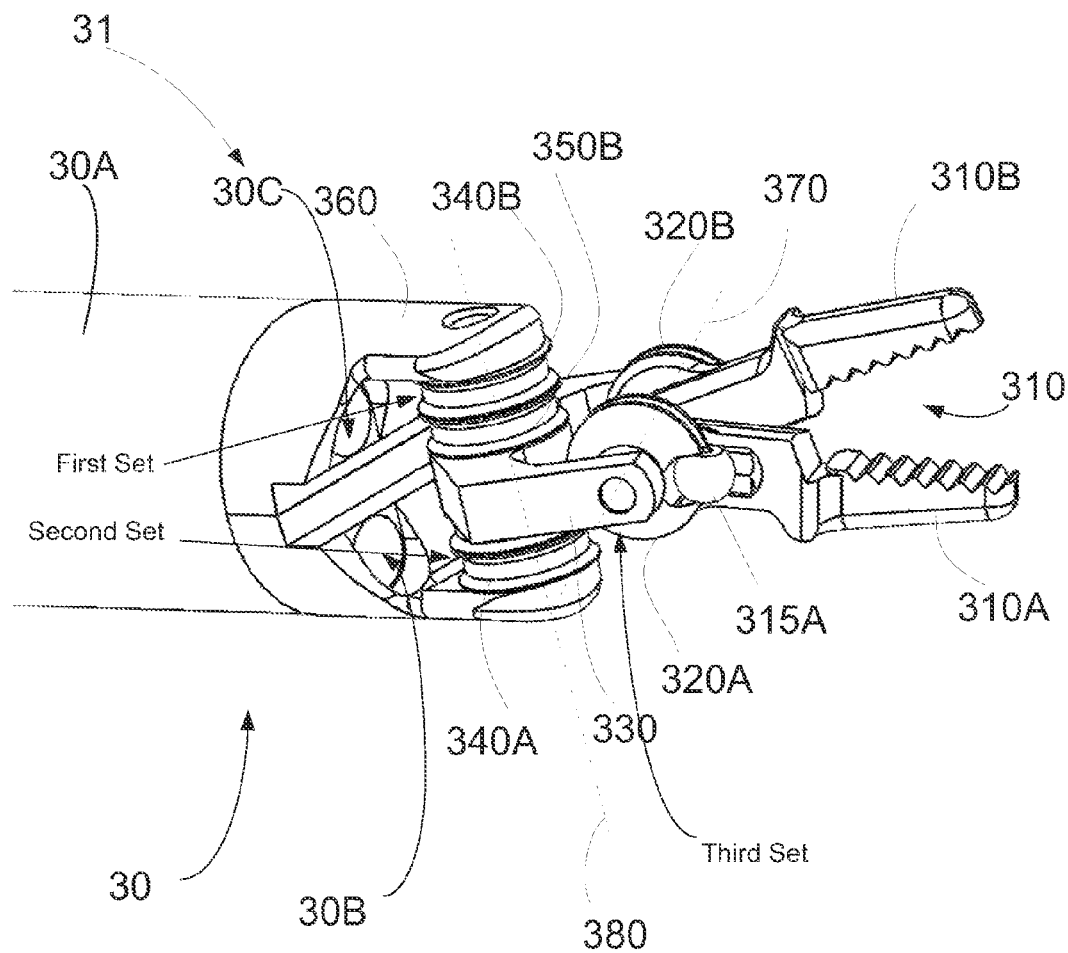
FIG. 1A illustrates a distal end of one embodiment of a tool including a wrist and an end effector.
Figure 1B:
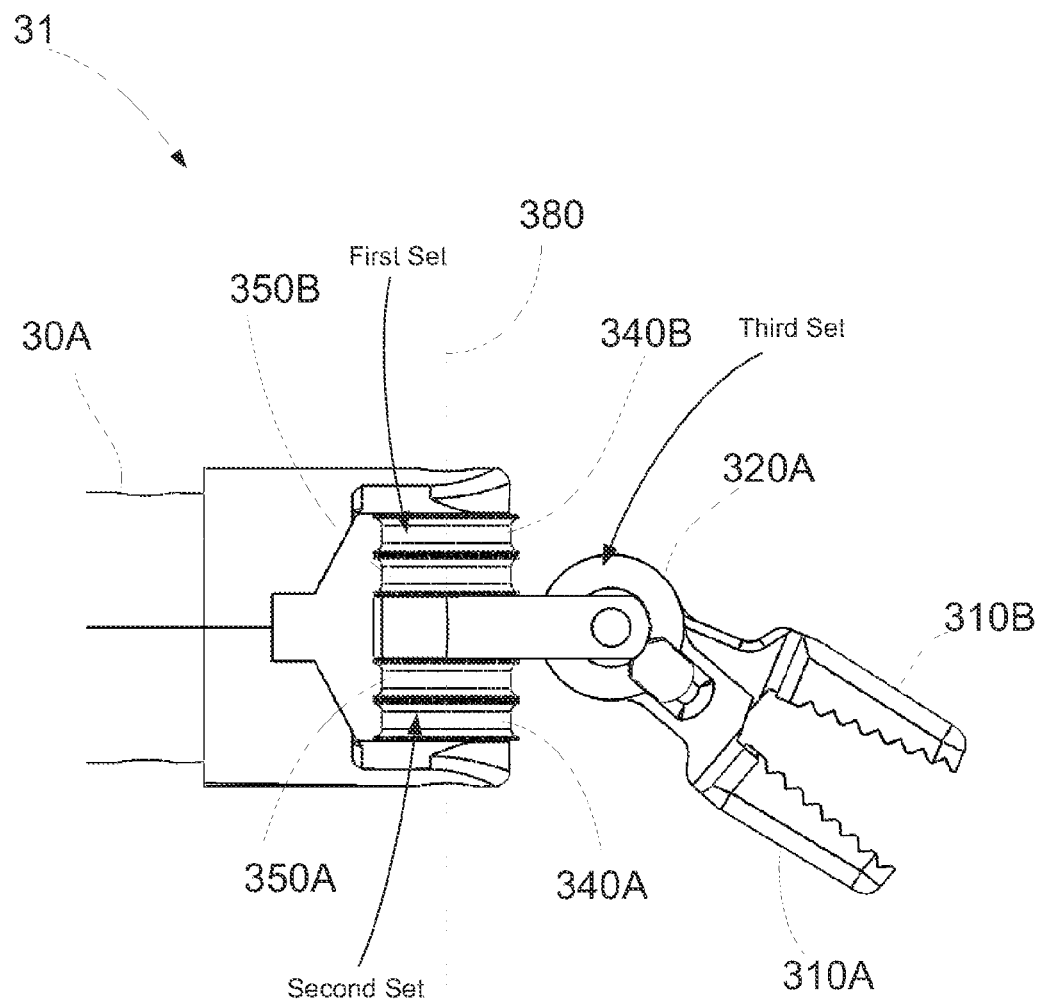
FIG. 1B illustrates the tool of FIG. 1A.

FIGS. 1A-1B show one embodiment of a tool 30 having a proximal end (not shown) and a distal end 31, where the configuration of the wrist of the tool and cable routing of the tool 30, as discussed below, advantageously allows for a reduction in the size of the wrist of the tool. In some embodiments, the reduction in the size of the wrist is enabled by cable routing that is simpler, which allows for a reduction in the complexity of the wrist assembly of the tool and allows for a shorted radius of curvature for the wrist. In some embodiments, the reduction in the size of the wrist of the tool 30 can include a reduction in the diameter of the wrist.

Figure 2:
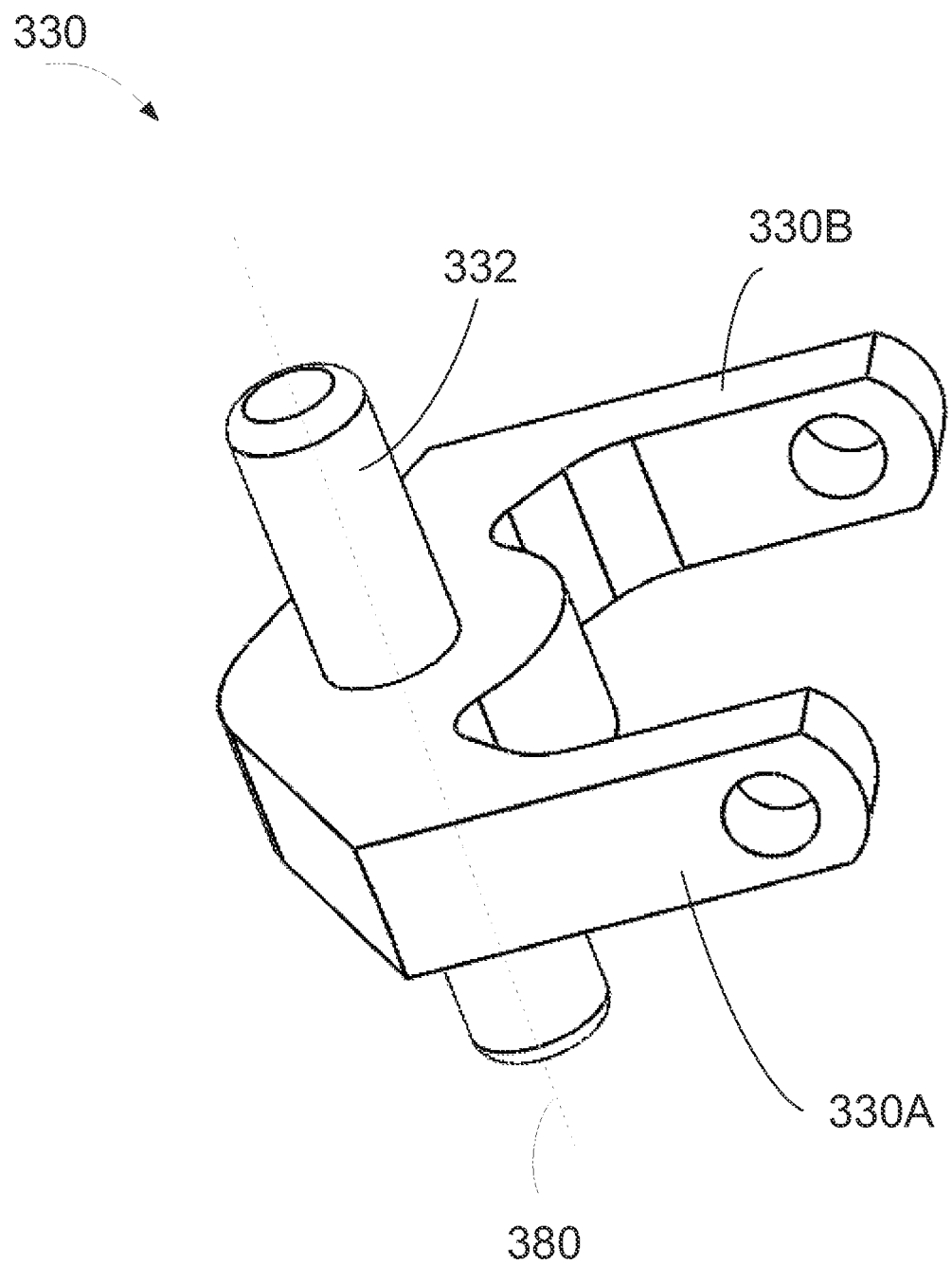
FIG. 2 illustrates a yoke of FIG. 1A.

As shown in FIG. 1A, the distal end 31 of the tool 30 can have a yoke 360 coupled to a shaft 30A of the tool 30. The yoke 360 is movably coupled to a second yoke 330 via an extended axle 332 that extends along an axis 380 (as shown in FIG. 2). In one embodiment, the extended axle 332 can be removable or integrally formed with the second yoke 330. In other embodiments, the extended axle 332 can be removable or integrally formed with the yoke 360, such that portions of the axle 332 are attached to the arms of the yoke 360 and the yoke 330 can be inserted between said portions of the axle 332. In one embodiment, the tool 30 can be a surgical tool. In another embodiment, the tool 30 can be a non-surgical tool.

As shown in FIG. 1B, the extended axle 332 of the second yoke 330 is coupled with pulleys 340A, 340B, 350A, 350B such that the pulleys 340A, 340B, 350A, 350B are arranged along the axis 380 of the extended axle 332. The pulleys 340A, 340B, 350A, 350B are arranged into a first set of pulleys 340B, 350B and a second set of pulleys 340A, 350A. The first set of pulleys 340B, 350B are on one side of the yoke 330, and the second set of pulley 340A, 350A are on the other side of the yoke 330. The pulleys 340A, 340B are outer pulleys and the pulleys 350A, 350B are inner pulleys.

The terms "inner" and "outer" indicate the orientation of the pulleys as shown in the Figures. As used herein, a "set" of pulleys can include any number of pulleys. A set of pulleys can include one pulley. A set of pulleys can include more than one pulley (e.g., two, three, four, five, six pulleys etc.).

With continued reference to FIGS. 1A-1B, the second yoke 330 is coupled to a third set of pulleys 320A, 320B. The third set of pulleys 320A, 320B can be spaced a distance (e.g., distally) from the axis 380. The third set of pulleys 320A, 320B are coupled to arms 330A, 330B of the second yoke 330 and arranged along an axis 370 defined through the arms 330A, 330B. In one embodiment, the second yoke 330 can include an extended axle that extends along the axis 370.

In one embodiment, the extended axle can be removably coupled with the second yoke 330. In another embodiment, the extended axle can be integrally formed with the second yoke 330 such that portions of the axle are attached to the arms of the second yoke 330 and the pulleys 320A, 320B can be inserted between said portions of the axle. In one embodiment, the axis 370 can be angled relative to the axis 380. In another embodiment, the axis 370 can be orthogonal to the axis 380. The first set of pulleys 340B, 350B can be orthogonal to the third set of pulleys 320A, 320B. The second set of pulleys 340A, 350A can also be orthogonal to the third set of pulleys 320A, 320B.

A pair of jaws 310A, 310B of a grasper 310 can be coupled to the second yoke 330 via the third set of pulleys 320A, 320B, so that the jaws 310A, 310B can rotate about the axis 370. In one embodiment, the jaw 310A is coupled to the pulley 320A. In another embodiment, the jaw 310A can be integrally formed with the pulley 320A. Similarly, in one embodiment, the jaw 310B is coupled to the pulley 320B. In another embodiment, the jaw 310B can be integrally formed with the pulley 320B. The jaw 310A and the pulley 320A can rotate about the axis 370. Similarly, the jaw 310B and the pulley 320B can rotate the about axis 370. In the illustrated embodiment, the grasper 310 is an end effector of the tool 30. However, in other embodiments, the end effector can be other suitable mechanisms, such as mechanisms used in surgical procedures (e.g., percutaneous surgical procedures).

The tool 30 can be actuated to move one of both of the jaws 310A, 310B in a variety of ways around the axis 370. For example, the jaws 310A, 310B may open and close relative to each other. The jaws 310A, 310B may also be actuated to rotate together as a pair to provide a yaw motion of the grasper 310. Additionally, the tool 30 can be actuated to affect various types of motions of the jaws 310A, 310B around the axis 380. For example, the second yoke 330, the pulleys 320A, 320B, and the jaws 310A, 310B can rotate about the axis 380 to provide a pitch motion of the grasper 310.

Figure 3A:
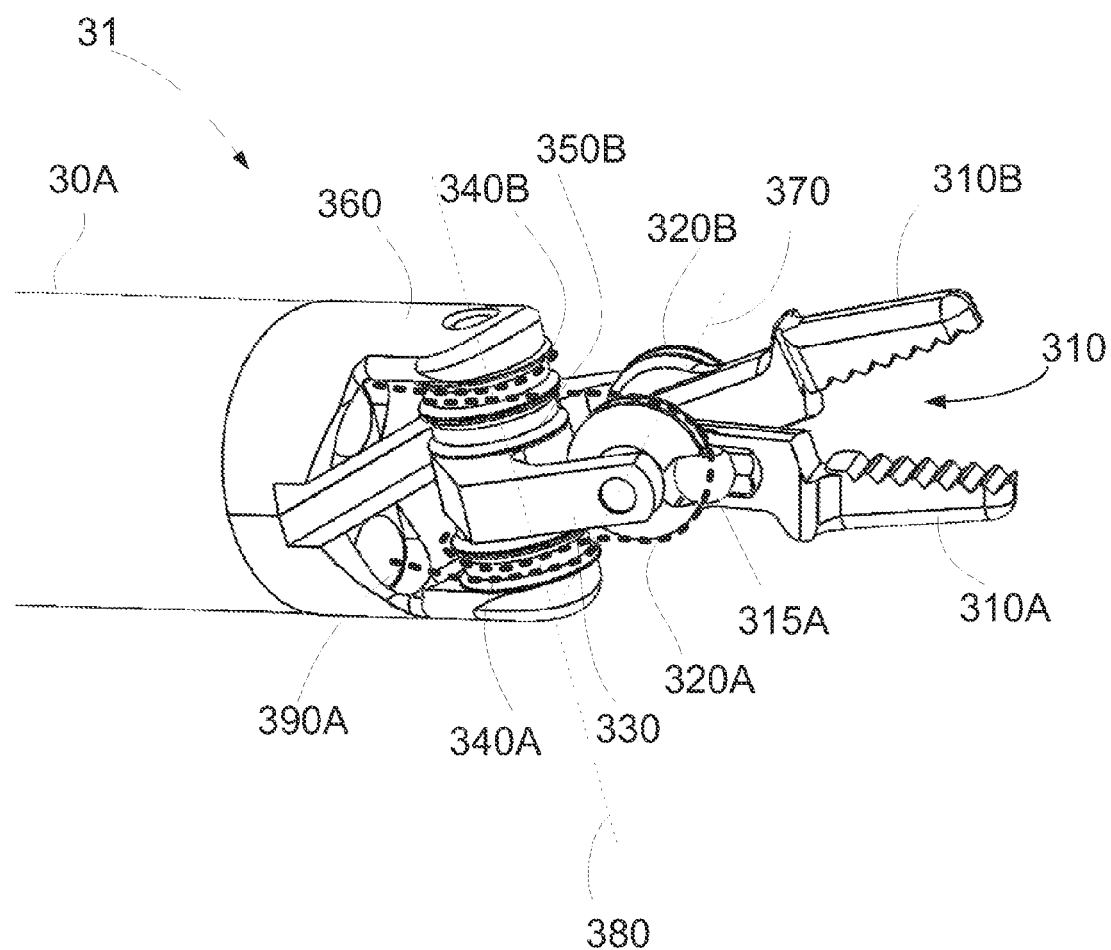
FIG. 3A illustrates the routing of a first cable of the tool of FIG. 1A.
Figure 3B:
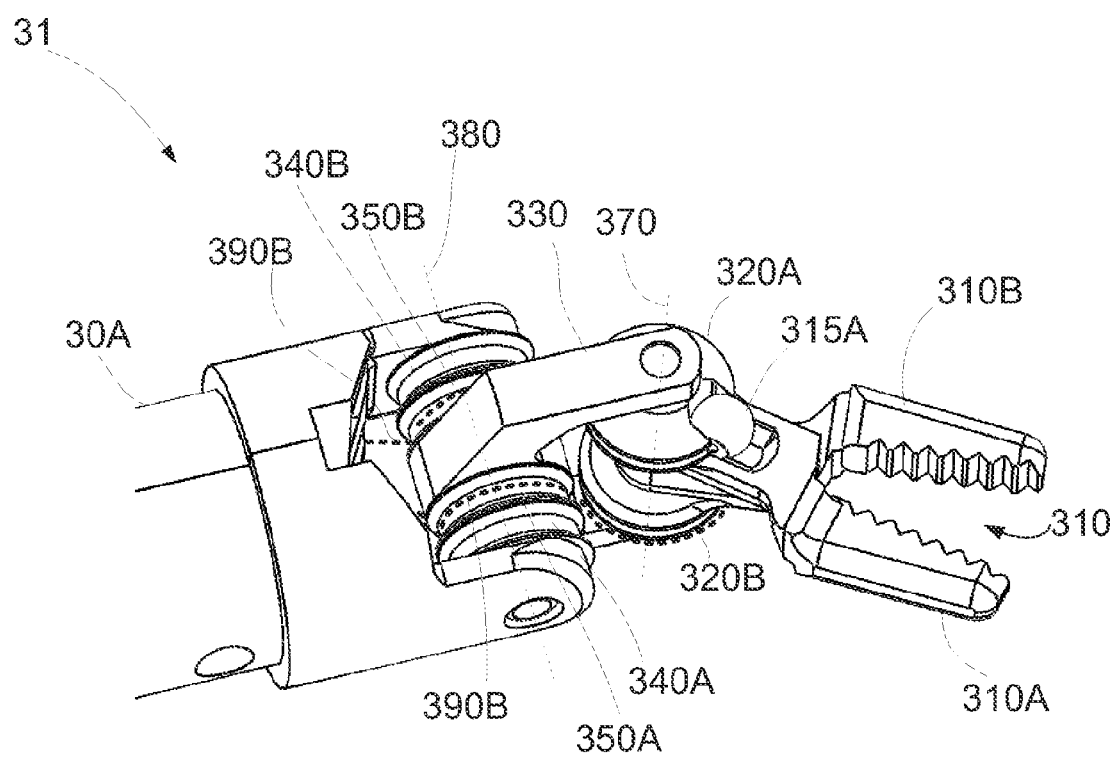
FIG. 3B illustrates the routing of a second cable of the tool of FIG. 1A.

FIGS. 3A-3B show an embodiment of the orientation of the cables of the tool 30. Advantageously, as described below, the routing of the cables allows the motion of the grasper 310 to be controlled via the actuation of four independent cable ends or two cable loops, which allows the number of cables used to control the grasper 310 to be reduced relative to on-market tools (which typically use three cable loops with six cable ends), thereby advantageously allowing the size and complexity of the wrist of the tool 30 to be reduced, as discussed above. This advantageous feature (e.g., ability to control movement of an end effector via the actuation of only four independent cable ends or two cable loops) is present in tools described in embodiments of this disclosure.

With reference to FIGS. 3A-3B, the third set of pulleys 320A, 320B can each include a pocket or recess. In one embodiment, the pocket is sized to at least partially retain a bead 315A, 315B. The bead 315B is not shown in FIGS. 3A-3B but can be similar to bead 315A as shown in these figures. The bead 315A can be affixed to a first cable 390A and the bead 315B can be affixed to a second cable 390B, where the cables 390A, 390B each have two independent cable ends. The beads 315A, 315B are affixed to the cables 390A, 390B in such a way as to inhibit (e.g., prevent) the cables 390A, 390B from slipping or sliding relative to the pulleys 320A, 320B. The cables 390A, 390B are coupled immovably to the beads 315A, 315B. In one embodiment, the beads 315A, 315B can be integrally formed with the cables 390A, 390B. In another embodiment, the beads 315A, 315B can be crimped on to the cables 390A, 390B.

FIG. 3A shows the cable routing of a first cable 390A, which is shown in dashed lines in FIG. 3A. The first cable 390A originates in the proximal end of the tool 30 and extends through the tool shaft 30A. The first cable 390A extends through a hole or aperture 30C (see FIG. 1A) in the yoke 360. The first cable 390A winds at least partially around one pulley in the first set of pulleys 340B, 350B. The first cable 390A winds at least partially around one pulley in the third set of pulleys 320A, 320B. The first cable 390A winds at least partially around one pulley in the second set of pulleys 340A, 350B. In some embodiments, the first cable 390A winds at least partially around the pulley 340B, the pulley 320A, and the pulley 340A, as shown in FIG. 3A. The first cable 390A then passes through another hole or aperture 30B (see FIG. 1A) in the yoke 360 and returns to the proximal end of the tool 30 via the tool shaft 30A.

In some embodiments, the first cable 390A can be replaced by two cables 390A' and 390A" (not shown) that may be coupled to the pulley 320A (e.g., where the cable 390A is replaced with two separate cable portions 390A', 390A"). The cable 390A' winds at least partially around one pulley in the first set of pulleys 340B, 350B and the cable 390A" winds at least partially around one pulley in the second set of pulleys 340A, 350A. In this embodiment, the cables 390A', 390A" traverse only one side of one pulley in the third set of pulleys 320A, 320B. In one embodiment, each of the cables 390A', 390A" traverse only one side of the pulley 320A. In some embodiments, the cables 390A', 390A" are coupled immovably to the pulley 320A (e.g., via bead 315A). For example, the bead 315A can be crimped onto an end of each of the cables 390A', 390A", and the bead 315A retained in the pocket of the pulley 320A, as discussed above, to thereby immovably couple the cables 390A', 390A" to the pulley 320A. The effect of having two independent cables 390A', 390A" affixed to a pulley 320A or having one cable 390A affixed to the pulley 320A is the same.

FIG. 3B shows a second cable 390B in dashed lines. The second cable 390B originates in the proximal end of the tool 30 and extends through the tool shaft 30A. The second cable 390B extends through the hole or aperture 30C (see FIG. 1A) in the yoke 360. The second cable 390B winds at least partially around one pulley in the first set of pulleys 340B, 350B. The second cable 390B winds at least partially around one pulley in the third set of pulleys 320A, 320B. The second cable 390B winds at least partially around one pulley in the second set of pulleys 340A, 350A. In some embodiments, the second cable 390B winds at least partially around the pulley 350B, the pulley 320B, and the pulley 350A, as shown in FIG. 3B. The second cable 390B then passes through the hole or aperture 30B (see FIG. 1A) in the yoke 360 and returns to the proximal end of the tool 30 via the tool shaft 30A.

In some embodiments, the second cable 390B can be replaced by two cables 390B' and 390B" (not shown) that may be coupled to the pulley 320B in a similar manner as described above for cables 390A', 390A". Therefore, in some embodiments, four independent cables 390A', 390A", 390B' and 390B" can be used. For example, in one embodiment, the cable 390B' winds at least partially around one pulley in the first set of pulleys 340B, 350B and the cable 390B" winds at least partially around one pulley in the second set of pulleys 340A, 350A. In this embodiment, the cables 390B', 390B" traverse only one side of one pulley in the third set of pulleys 320A, 320B. In one embodiment, each of the cables 390A', 390A" traverse only one side of the pulley 320B. In some embodiments, the cables 390B', 390B" are coupled immovably to the pulley 320B (e.g., via bead 315B, not shown). For example, the bead 315B can be crimped onto an end of each of the cables 390B', 390B", and the bead 315B retained in the pocket of the pulley 320B, as discussed above, to thereby immovably couple the cables 390B', 390B" to the pulley 320B. The effect of having two independent cables 390B', 390B" affixed to a pulley 320B or having one cable 390B affixed to the pulley 320B is the same.

The tool 30 can be actuated to move the jaws 310A, 310B in a variety of ways such as grasping (e.g., jaws rotating independently about axis 370), yaw (e.g., jaws rotating together about axis 370), and pitch (e.g., jaws rotating about axis 380) by imparting motion to one or more of the pulleys 340A, 340B, 350A, 350B, 320A, 320B to thereby impart motion on the yoke 330 and/or one or both of the jaws 310A, 310B. In one embodiment, where the tool 30 has two cables 390A, 390B that effect the movement of the grasper 310, each cable 390A, 390B has two independent cable ends which may be independently controlled or tensioned to impart motion on the third set of pulleys 320A, 320B and the jaws 310A, 310B. For example, motion of the pulley 320A and the jaw 310A can be controlled with the two cable ends of cable 390A. Similarly, motion of the pulley 320B and the jaw 310B can be controlled with the two cable ends of cable 390B. The system of FIGS. 1A-3B has four cable ends. The four cable ends may be controlled to impart motion on one or more of the pulleys, 340A, 340B, 350A, 350B, 320A, 320B. The four cable ends (a pair for each cable 390A, 390B) can be coupled to motors near the proximal end 32 (not shown) of the tool 30, as further described below. In other embodiments, the four cable ends (a pair for each cable 390A, 390B) are coupled to motors located at any distance along the tool shaft 30A.

In another embodiment, where the tool 30 has four cables 390A', 390A", 390B', 390B" that effect the movement of the grasper 310, each cable 390A', 390A", 390B', 390B" has one independent cable end which may be independently controlled or tensioned to impart motion on the yoke 330 and/or one or both of the third set of pulleys 320A, 320B. Independent cable ends can be considered free cable ends (e.g., the ends not coupled to the bead 315A, 315B). Motion of the pulley 320A can be controlled by the independent cable ends of cables 390A', 390A". Motion of the pulley 320B can be controlled by the independent cable ends of cables 390B', 390B". The system of FIGS. 1A-3B has four independent cable ends. The four cable ends may be controlled to impart motion on one or more of the pulleys, 340A, 340B, 350A, 350B, 320A, 320B to thereby impart motion on the yoke 330 and/or one or both of the jaws 310A, 310B. The four cable ends (an end for each cable 390A', 390", 390B', 390B") can be located near the proximal end (not shown) of the tool 30 or at any distance along the tool shaft 30A.

In some embodiments, a pitch motion of the yoke 330 and the jaws 310A, 310B about the axis 380 is achieved by tensioning both ends of one cable (e.g., 390A) and relaxing both ends of the other cable (e.g., 390B). For example, referring to FIGS. 3A-3B, to pitch the jaws 310A, 310B out of the plane of the paper, both ends of cable 390A are tensioned and both ends of cable 390B are relaxed. To pitch the jaws into the plane of the paper, both ends of cable 390A are relaxed and both ends of cable 390B are tensioned.

In some embodiments, a yaw motion of the jaws 310A, 310B of the grasper 310 about the axis 370 is achieved by moving the pulleys 320A, 320B in the same direction. For example, referring to FIG. 3A, to yaw the jaws 310A, 310B upward, both pulleys 320A, 320B have to move in a counterclockwise direction. The end of the cable 390A coupled to one pulley in the first set of pulleys 340B, 350B is tensioned and the end of the cable 390B coupled to one pulley in the first set of pulleys 340B, 350B is tensioned. In FIG. 3A, the end of the cable 390A coupled to 340B, and the end of the cable 390B coupled to 350B are tensioned. The other ends of the cables 390A, 390B are relaxed. The jaws 310A, 310B will therefore rotate about axis 370 upward. To yaw the jaws 310A, 310B downward, both pulleys 320A, 320B have to move in a clockwise direction. The end of the cable 390A coupled to one pulley in the second set of pulleys 340A, 350A and the end of the cable 390B coupled to one pulley in the second set of pulleys 340A, 350A are tensioned. In FIGS. 3A-3B, the end of the cable 390A coupled to 340A, and the end of the cable 390B coupled to 350A are tensioned. The other ends of the cables 390A, 390B are relaxed. Such a combination of tensioning and relaxation of the cables 390A, 390B will cause the jaws 310A, 310B to rotate about axis 370 downward.

The jaws 310A, 310B can be moved relative to each other, for example to effect a grasping action, a release action, or a scissoring motion. To move the jaws 310A, 310B toward each other, the pulley 320A can move in a counterclockwise direction and the pulley 320B can move in a clockwise direction. To achieve such motion, the end of the cable 390A coupled to one pulley in the first set of pulleys 340B, 350B and the end of the cable 390B coupled to one pulley in the second set of pulleys 340A, 350A are tensioned. In FIGS. 3A-3B, the end of the cable 390A coupled to 340B, and the end of the cable 390B coupled to 350A are tensioned. The other ends of the cables 390A, 390B are relaxed. Such a combination of tensioning and relaxation of the cables 390A, 390B will cause the jaws 310A, 310B to rotate about axis 370 toward each other.

To move jaws 310A, 310B apart, the pulley 320A can move in a clockwise direction and the pulley 320B can move in a counterclockwise direction. The end of the cable 390A coupled to one pulley in the second set of pulleys 340A, 350A and the end of the cable 390B coupled to one pulley in the first set of pulleys 340B, 350B are tensioned. In FIGS. 3A-3B, the end of the cable 390A coupled to 340A, and the end of the cable 390B coupled to 350B are tensioned. The other ends of the cables 390A, 390B are relaxed. Such a combination of the tensioning and relaxing of the cables 390A, 390B will cause the jaws 310A, 310B to rotate about axis 370 away from each other.

The jaws 310A, 310B can be moved toward or away from each other by applying different amounts of tension to each cable end. By applying varying amounts of tension, the jaws 310A, 310B will yaw differently, effectively emulating a grasping or release action. All three modes of movement (pitch, yaw and grasping action) can be obtained by varying the cable ends that are being tensioned and relaxed, and/or by varying the amount of tension and relaxation applied to each cable end. Although a specific routing configuration is described in FIGS. 1A-3B, other routing configurations are possible. For example, cable 390A may wind around the inner pulley 350B instead of winding around outer pulley 340B as described above.

Figure 4A:
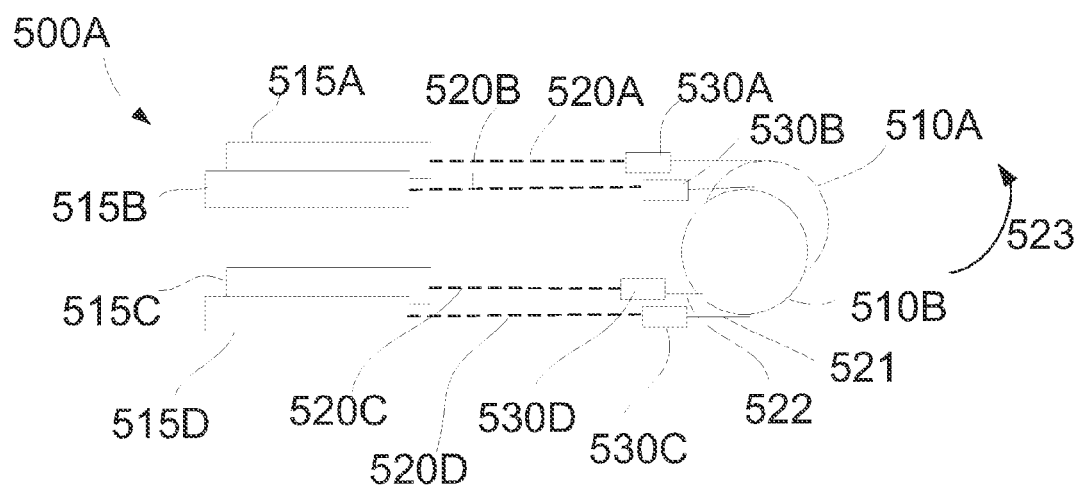
FIG. 4A schematically illustrates an embodiment of a twisted string based drive mechanism for a tool.

In some embodiments, motion of a wrist and/or end effector of a tool can be effected with one or more twisted strings. A twisted string pair works on the principle of twisting two component strings around each other so that the length of the twisted string pair can be shortened, thus creating tension along the twisted string pair. Similarly, as the component strings of a twisted string pair unwind, the length of the twisted string pair approaches the natural length of each component string. FIGS. 4A-4D show embodiments of drive mechanisms and methods of controlling a tool, such as tool 30, with twisted strings and cables. FIG. 4A schematically shows a drive mechanism 500A for controlling cables of a tool. The system includes two cables 521, 522. Each cable 521, 522 is associated with a pulley 510A, 510B. The pulleys 510A, 510B are the objects being driven. The cable 521 may be associated with multiple pulleys, although one pulley 510B is shown. Similarly, the cable 522 may be associated with multiple pulleys, although one pulley 510A is shown. Each cable 521, 522 has two cable ends. Each cable end is coupled to a transition block 530A, 530B, 530C, 530D. Each transition block 530A, 530B, 530C, 530D is coupled to a twisted string pair 520A, 520B, 520C, 520D. Each twisted string pair 520A, 520B, 520C, 520D is coupled to a motor 515A, 515B, 515C, 515D.

With continued reference to FIG. 4A, each twisted string pair 520A, 520B, 520C, 520D is driven by an axial motor 515A, 515B, 515C, 515D. For example, twisted string pair 520A is driven by axial motor 515A and twisted string pair 520B is driven by axial motor 515B.

The transition blocks 530A, 530B, 530C, 530D provide a transition between the twisted string pairs 520A, 520B, 520C, 520D and the cables 521, 522. As shown in FIG. 4A, the cable 521 extends between transition blocks 530B and 530C. The cable 522 extends between transition blocks 530A and 530D. The twisted strings pairs 520A, 520B, 520C, 520D may exhibit unpredictable behavior when contacting a surface over which the twisted strings pairs need to bend (e.g., a curved surface of the pulleys 510A, 510B), so the transition blocks 530A, 530B, 530C, 530D provide a transition between the twisted string pairs 520A, 520B, 520C, 520D and the cables 521, 522 so that only the cables 521, 522 contact the curved surfaces of the pulleys 510A, 510B.

Figure 4B:
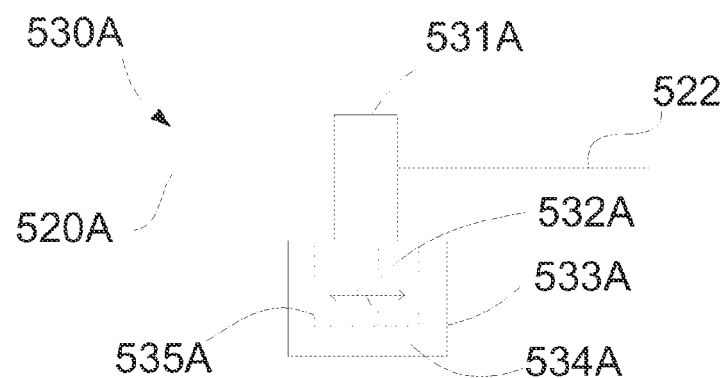
FIG. 4B schematically illustrates an embodiment of a transition block of a twisted string based drive mechanism.

FIG. 4B shows the transition block 530A. In one embodiment, all four transition blocks 530A, 530B, 530C and 530D have similar features to the transition block 530A. The twisted string pair 520A is coupled to a termination block 531A. The cable 522 is also coupled to the termination block 531A. The termination block 531A is coupled immovably to a peg 532A. In one embodiment, the termination block 531A can be integrally formed with the peg 532A.

The peg 532A can slide within a slot 535A in a base block 533A along arrow 534A to allow the twisted string pair 520A to shorten or increase in length. In the illustrated embodiment, the peg 532A and slot 535A are both internal structures of the base block 533A, and shown in dashed line form. The peg 532A and slot 535A advantageously prevent the termination block 531A from rotating or spinning due to the influence of the twisted string pair 520A. When the length of the twisted string pair 520A is decreased, the peg 532A coupled to the termination block 531A slides within the slot 535A in the base block 533A, and the termination block 531A in turn pulls the cable 522. The cable 522 transmits this tension to the pulley 510A to rotate the pulley 510A.

With continued reference to FIG. 4A, the twisted string pair 520A is moved relative to the twisted string pair 520C. The motor 515A may wind the twisted string pair 520A attached to the motor 515A, thereby shortening the length of the twisted string pair 520A. The motor 515C may unwind the twisted string pair 520C attached to the motor 515C, thereby extending the length of the twisted string pair 520C. These two actions cause the cable 522 to be pulled towards motor 515A, causing the pulley 510A to rotate in a counterclockwise direction. To move the pulley 510A in the clockwise direction, the motor 515A would unwind the twisted string pair 520A and the motor 515C would wind the twisted string pair 520C. The motors 515B, 515D can move the cable 521 and the pulley 510B in a similar manner. The cables 521, 522 can be coupled to a bead, similar to beads 315A, 315B, and the bead can be coupled to the pulleys 510A, 510B (e.g., retained in pockets of the pulleys 510A, 510B, in the manner discussed above). Additionally, in other embodiments, each of the cables 521, 522 can be replaced by two independent cables so that four cables extend between the transition blocks 530A, 530B, 530C, 530D and beads on the pulleys 510A, 510B.

In another mode of driving the pulleys 510A, 510B, both twisted string pairs can be wound equally. For example, motors 515A, 515C may both wind the twisted string pairs 520A and 520C, while motors 515B, 515D are not actuated. Pulley 510A will not rotate in this case but experience a pulling force in the direction of the motors 515A, 515C, causing a yaw motion into the page along arrow 523. If instead motors 515B, 515D are actuated to wind the twisted string pairs 520B, 530D, while motors 512A, 515C are not actuated, pulley 510B will not rotated but experience a pulling force in the direction of motors 515B, 515D, thereby causing a yaw motion out of the page in a direction opposite to arrow 523. Further to the description above, the amount of yaw motion can be controlled by the amount the twisted string pairs are wound.

Figure 4C:
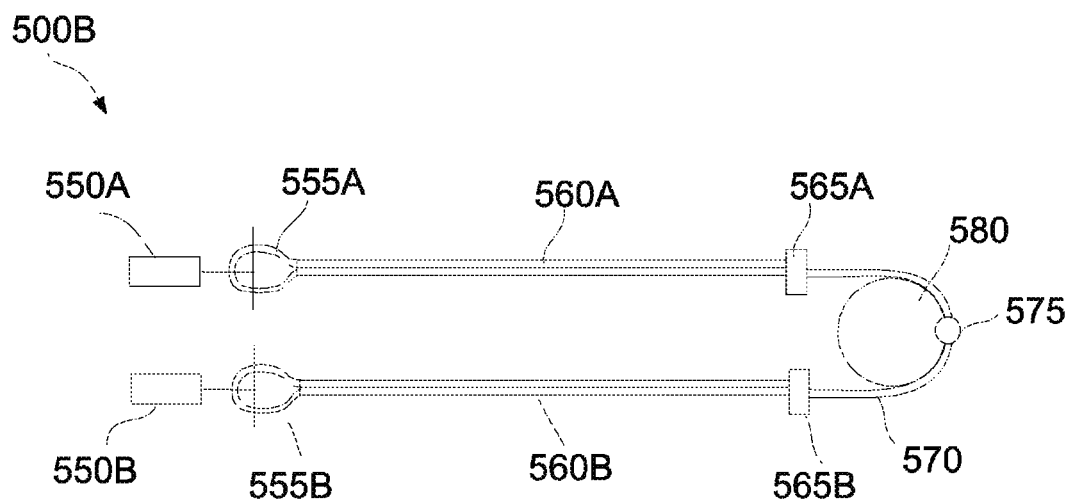
FIG. 4C schematically illustrates an embodiment of a twisted string based drive mechanism.

FIG. 4C schematically shows another drive mechanism 500B for controlling a tool, such as tool 30. The system includes a cable 570 associated with a pulley 580. In the illustrated embodiment, the cable 570 defines one or more twisted string pairs, as discussed further below. Although only one pulley 580 is shown, the cable can be associated with multiple pulleys, as discussed above. Additionally, the system can include a second cable (not shown) associated with a second pulley (not shown). In the illustrated embodiment, the pulley 580 is the object being driven. As described in previous embodiments, the cable 570 is coupled to two transition blocks 565A, 565B.

Each transition block 565A, 565B is coupled to a twisted string pair 560A, 560B. Each twisted string pair 560A, 560B forms a loop 555A, 555B. Each loop 555A, 555B is coupled to a motor 550A, 550B. The twisted string pair 560A is defined by the cable 570 doubled onto itself. In other words, the cable 570 couples to transition block 565A (e.g., couples to the peg of the transition block 565A so the peg can slide on the base block of the transition block 565A and not rotate, similar to transition block 530A), extends past the transition block 565A to define the twisted string pair 560A and loop 555A, and couples back to transition block 565A. Similarly, the twisted string pair 560B is defined by the cable 570 doubled onto itself. In other words, the cable 570 couples to transition block 565B and extends past the transition block 565B to define the twisted string pair 560B and loop 555B, and couples back to transition block 565B.

The motors 550A and 550B can wind or unwind the loops 555A, 555B and consequently wind or unwind the twisted string pair 560A, 560B. The cable 570 therefore extends from both sides of the termination block of the transition blocks 565A, 565B. The cable 570 can be attached to a bead 575, which can be similar to the attachment of cables to bead 315A in FIG. 3A. The drive mechanism 500B advantageously has fewer parts (e.g., one cable) compared to the drive mechanism 500A in FIG. 4A.

Figure 4D:
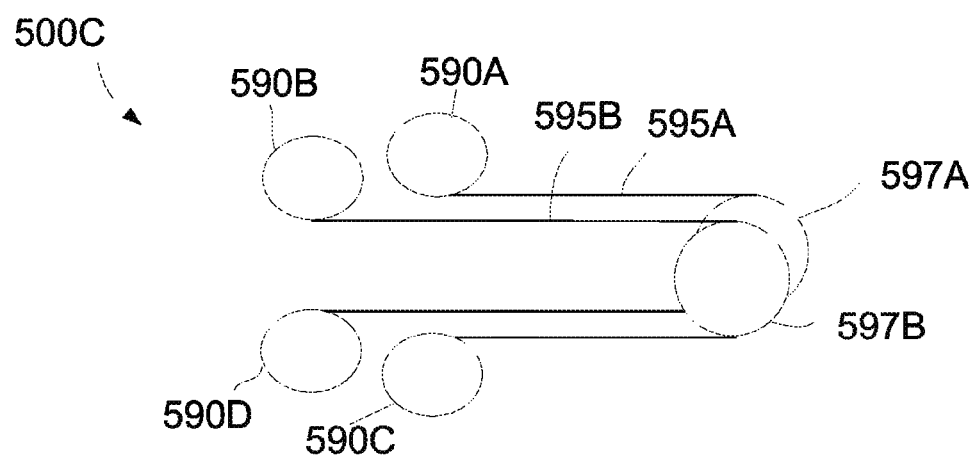
FIG. 4D schematically illustrates an embodiment of a cable based drive mechanism.

FIG. 4D schematically shows another drive mechanism 500C for controlling cables of a tool, such as tool 30. The system includes two cables 595A, 595B. Each cable 595A, 595B is associated with a pulley 597A, 597B. The pulleys 597A, 597B are the objects being driven. Each cable 595A, 595B has two cable ends. Each cable end is driven by a motor, 590A, 590B, 590C, 590D. The motors can be flat, high torque motors (electrical motors). In other embodiments, other types of motors can be used. The spools that wind and unwind the cables 595A, 595B are not shown.

Figure 5A:
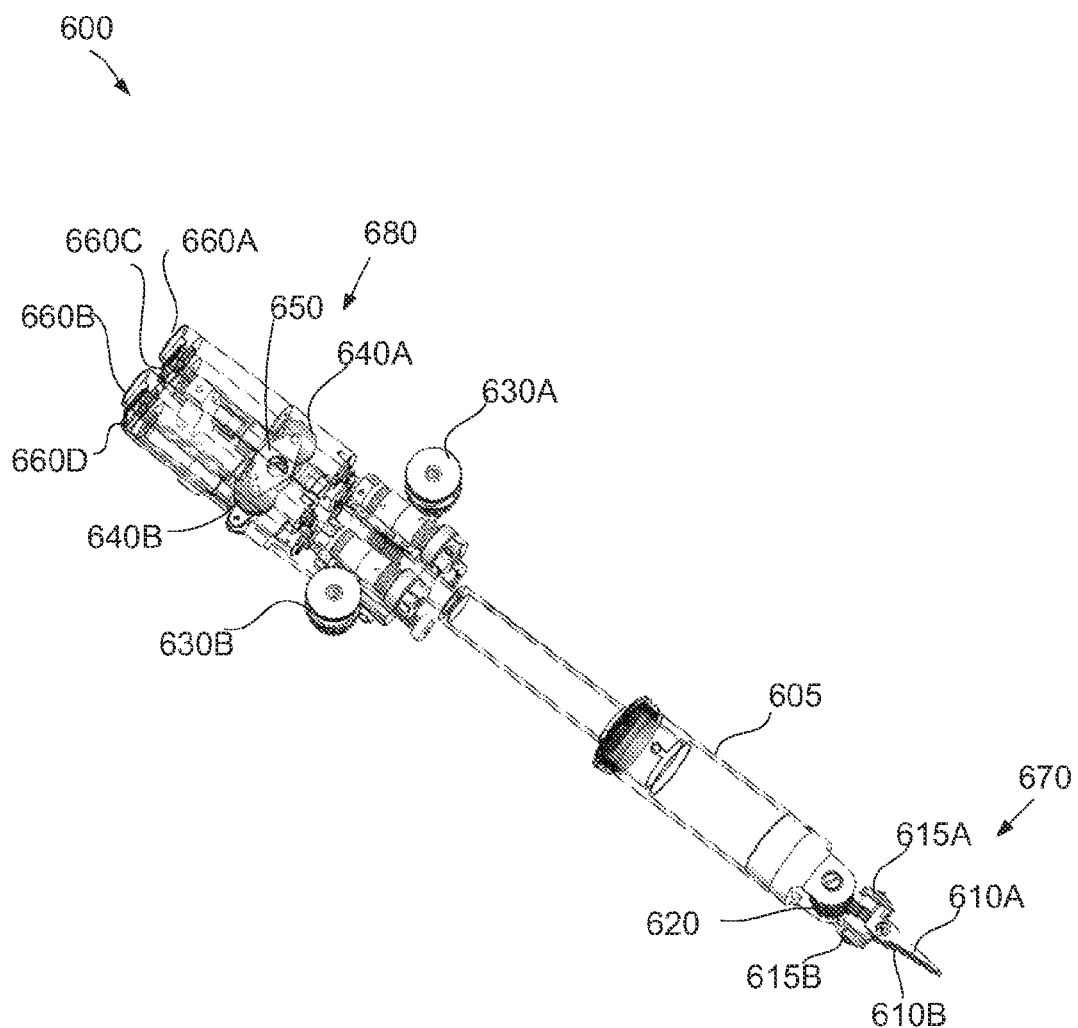
FIG. 5A illustrates an embodiment of a tool including a wrist and an end effector.

FIGS. 5A-6D show embodiments of mechanisms that can be incorporated with the tools described herein, including the drive mechanisms described above. FIG. 5A shows another embodiment of a tool. The tool 600 includes a distal end 670 and a proximal end 680. The distal end 670 can be substantially similar to the distal end 31 of the tool 30 shown in FIGS. 1A-3B. For clarity, the cables that drive the distal end 670 are not shown in FIG. 5A. As with the embodiments described previously, two cable loops having four cable ends are controlled to effect motion of a wrist and/or end effector of the tool 600. In the illustrated embodiment, the tool 600 can include four motors 660A, 660B, 660C, 660D. However, only three motors are required to drive the cables and control the four cable ends. In one embodiment, the fourth motor can provide roll or rotation of the distal end 670 of the tool 600 about its axis. In some embodiments, the tool 600 includes only three motors.

The tool 600 can include four pulleys 630A, 630B, 640A, 640B. The pulleys 630A, 630B can be located distally in relation to the pulleys 640A, 640B. The pulleys 630A, 630B can be considered front pulleys, and the pulleys 640A, 640B can be considered rear pulleys. The front pulleys 630A, 630B are each driven by a motor 660A, 660B, respectively. The rear pulleys 640A, 640B are coupled to a rocker mechanism 650.

Figure 5B:
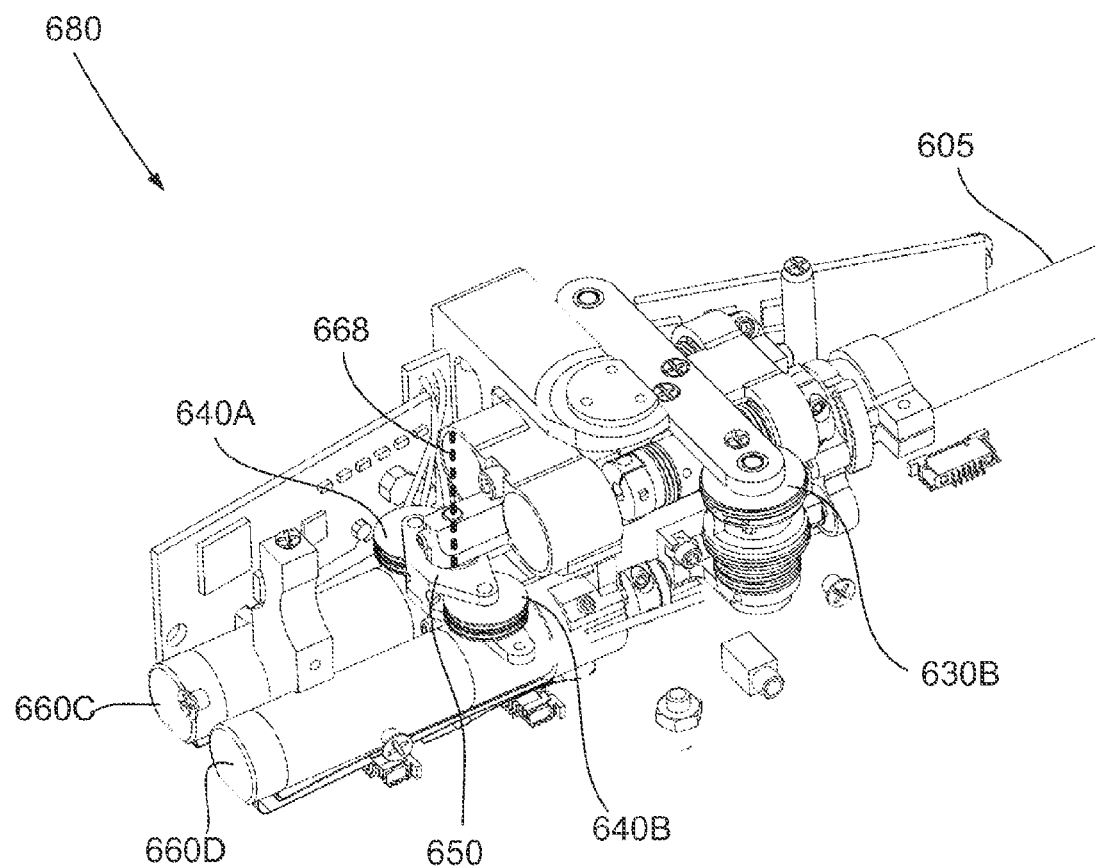
FIG. 5B illustrates a rocker mechanism of the tool of FIG. 5A

FIG. 5B shows the rocker mechanism 650. The motors 660A, 660B are not shown in FIG. 5B to more clearly illustrate the rocker mechanism 650. The rocker mechanism 650 can rock back and forth (in a clockwise and counterclockwise direction) about an axis 668. The axes of the pulleys 640A, 640B are coupled to the ends of rocker mechanism 650, as shown. In one embodiment, a plane defined by the axes of the pulleys 640A, 640B (e.g., a plane transverse to the longitudinal axis of the tool) can be axially offset from the axis 668 such that the axis 668 does not lie on said plane (e.g., so that planes defined by the axes of the rocker mechanism 650 and pulleys 640a, 640B define a triangle). In another embodiment, the axes of the pulleys 640A, 640B and the axis 668 can be on the same plane transverse to the longitudinal axis of the tool 600.

As the rocker mechanism 650 rotates counterclockwise, the pulley 640B is moved toward the distal end 670 of the tool 600 and the pulley 640A is moved toward the proximal end 680 of the tool 600. As the rocker mechanism 650 rotates clockwise, the pulley 640B is moved toward the proximal end 680 of the tool 600 and the pulley 640A is moved toward the distal end 670 of the tool 600. The position of the rocker mechanism 650 is determined by a motor (e.g., motor 660D). The motor 660D may be coupled to a lead screw. The lead screw may be coupled with a lead screw nut, which translates along the length of the lead screw. The lead screw nut may be coupled to a pushrod. The pushrod may be coupled to the rocker mechanism 650. As the motor 660D turns, the pushrod translates over the lead screw and alters the position of the rocker mechanism 150. The rocker mechanism 150 adjusts the position of the pulleys 640A, 640B, as discussed above, which in turn adjusts the tension imparted on the cables coupled to the pulleys 640A, 640B.

Figure 5C:
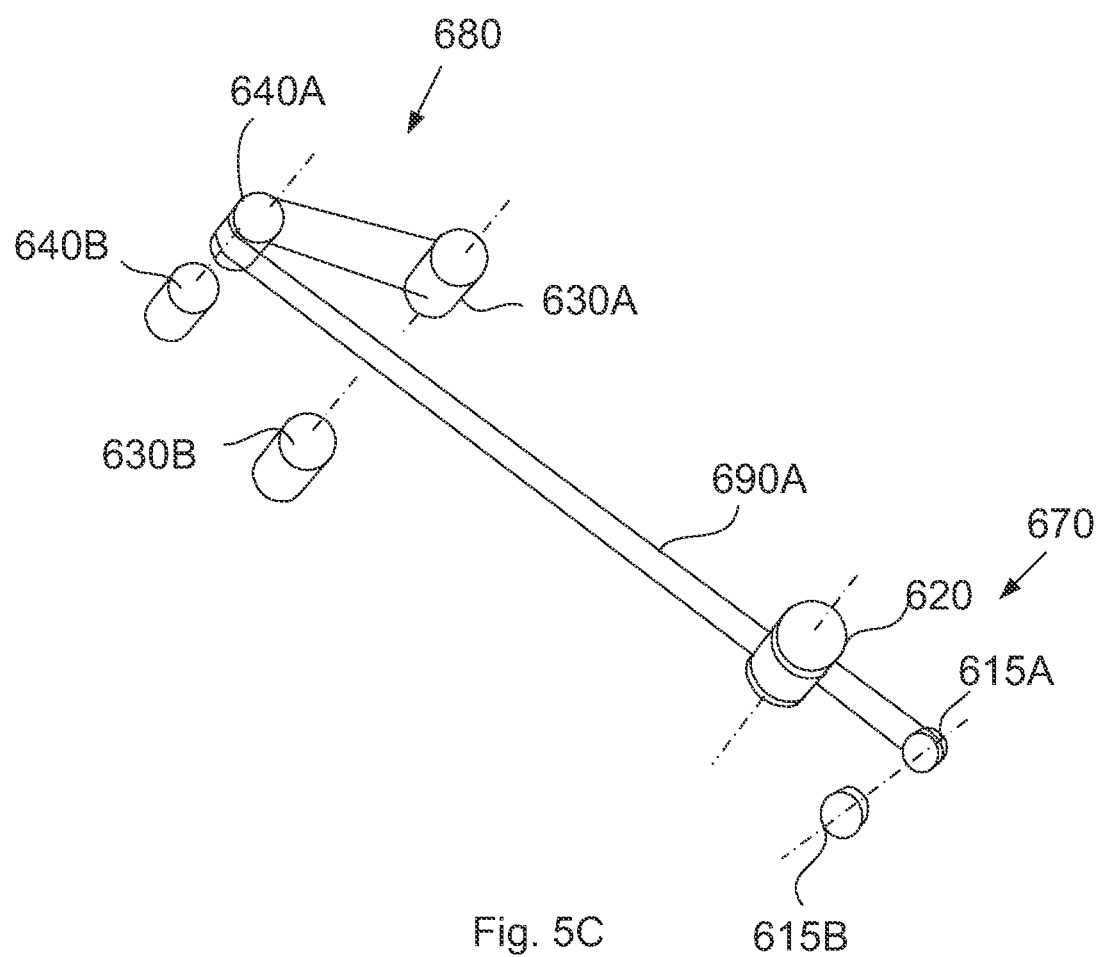
FIG. 5C schematically illustrates the cable routing of a first cable for the tool of FIG. 5A.

FIG. 5C illustrates the routing of a first cable 690A of the tool 600. The cable routing in the distal section 670 can be substantially similar to the cable routing illustrated in FIGS. 3A-3B. The pulleys 615A, 615B can be substantially similar to pulleys 320A, 320B. The pulleys 615A, 615B can be coupled to jaws 610A, 610B, as shown in FIG. 5A. The pulley 620 is similar to pulleys 340A, 340B, 350A, 350B. Both sides of the cable 690A wind around the pulley 620 in the same direction Proximal to pulley 620, the two sides of the cable 690A travel through the tool shaft 605 (see FIG. 5A) and wind at least partially around the pulley 640A, as shown in FIG. 5C. After exiting the pulley 640A, the free ends of the cable 690A are attached to the opposite sides of a spool 630A. The free ends of the cable 690A are at least partially wound around the spool 630A in opposite directions. The spool 630A is actuated by a motor (e.g., motor 660A). The speed with which spool 630A rotates can be controlled via gearboxes coupled to the motor 660A. As motor 660A turns, spool 630A turns, applying tension to one end of the cable 690A and releasing the tension on the other end of the same cable 690A. The cable 690A can couple to a bead retained in a pocket or recess of pulley 615A, in a manner similar to how cable 390A couples to the bead 315A in FIG. 3A.

As the spool 630A is rotated, a first cable end unwinds and the second cable end winds around spool 630A. The effect of this type of motion is that the pulley 620 will not rotate but the pulley 615A will rotate, which will cause the jaw 610A attached to the pulley 615A to move. For example, to yaw the jaw 610A upward, the pulley 615A has to move in a counterclockwise direction. To yaw the jaw 610 upward, the top cable end would need to be tensioned by winding the cable end around the spool 630A. To yaw the jaw downward, the bottom cable end would need to be tensioned. The rocker mechanism 650 can be in a neutral position (e.g., the pulleys 640A, 640B aligned along a plane orthogonal to the longitudinal axis of the tool 600).

Figure 5D:
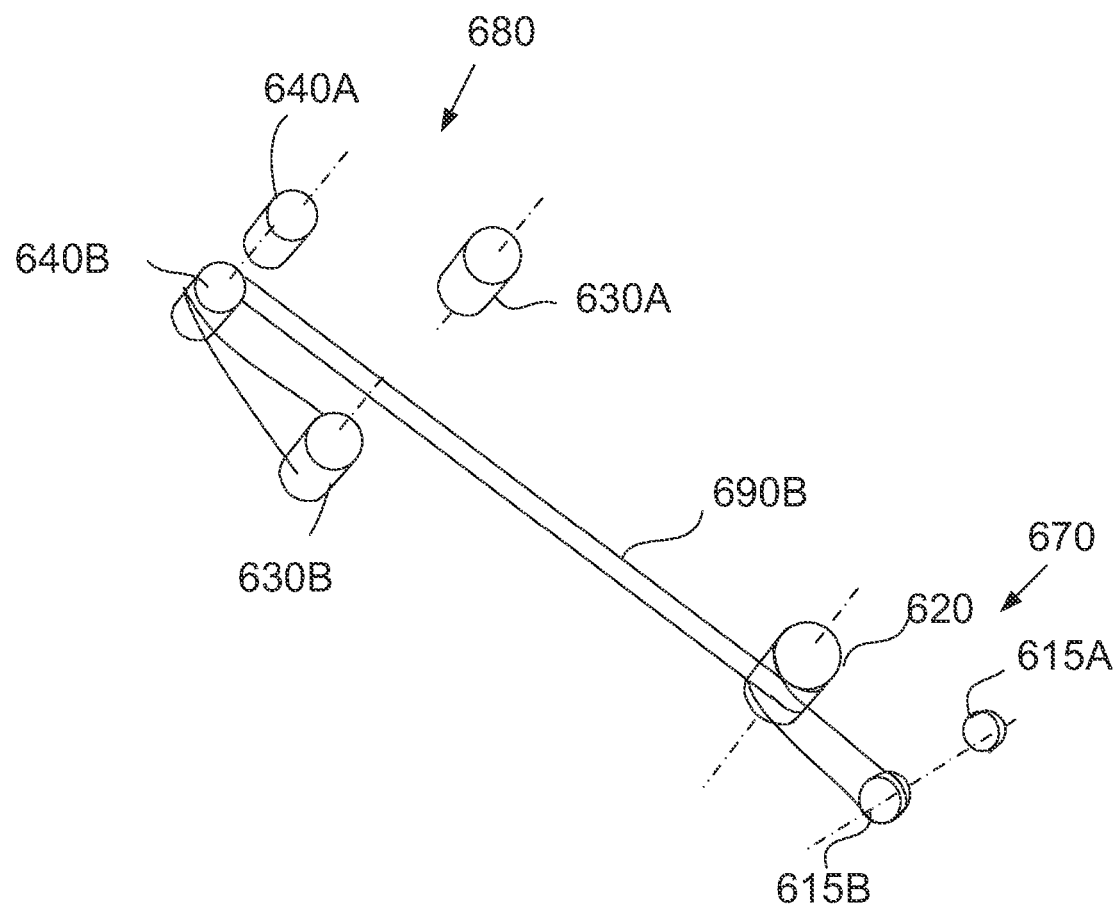
FIG. 5D schematically illustrates the cable routing of a second cable for the tool of FIG. 5A.

The tool 600 can be actuated to move the jaws 610A, 610B in a variety of ways such as grasping (e.g., jaws rotating independently via pulleys 615A, 615B), yaw (e.g., jaws rotating together via pulleys 615A, 615B), and pitch (e.g., jaws rotating about pulley 620). FIG. 5D illustrates the routing of a second cable in the tool 600. The routing is similar to that described in FIG. 5C. The cable 690B winds around pulley 620, around pulley 640B, and terminates at spool 630B. The spool 630B is driven by a motor (e.g., motor 660B). As the spool 630B rotates, tension is applied to one side of the cable 690B while tension on the other side of the cable 690B is relaxed. The effect of this rotation is to move the jaw 610B attached to the pulley 615B.

To move both of the jaws 610A, 610B upward at the same time, the spools 630A, 630B are driven by the motors to move pulleys 615A, 615B counterclockwise. This motion will provide yaw to the jaws 610A, 610B. To move both the jaws 610A, 610B downward at the same time, the spools 630A, 630B are driven by the motors to move pulleys 615A, 615B clockwise.

Figure 5E:
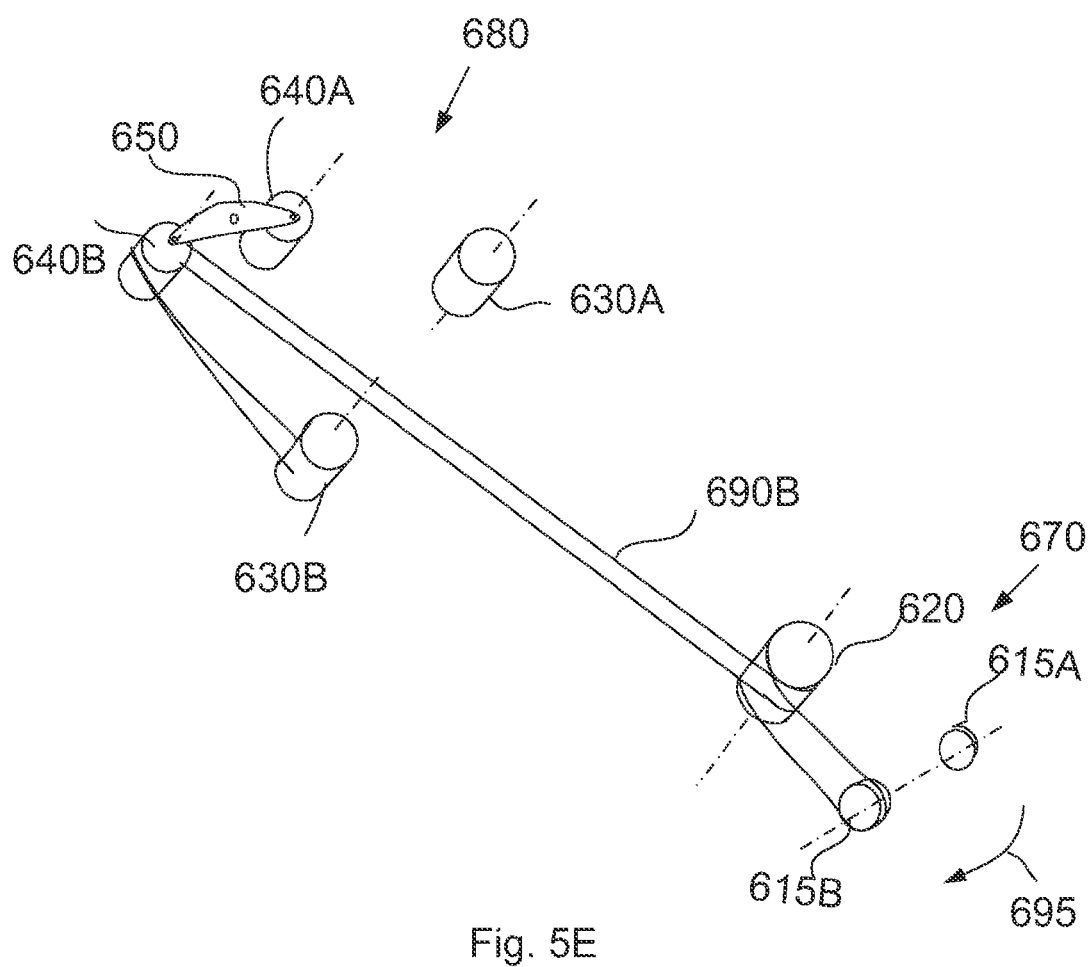
FIG. 5E schematically illustrates the rocker mechanism.

To provide pitch, the rocker mechanism 650 is manipulated, changing the position of the pulleys 640A, 640B relative to the longitudinal axis of the tool 600. FIG. 5E shows the rocker mechanism 650 rotated clockwise, moving the pulley 640A toward the distal end 670 of the tool 600 and the pulley 640B toward the proximal end 680 of the tool 600.

In this embodiment, the position of the rocker mechanism 650 increases the tension on both sides of the cable 690B. This tension causes the pulley 620 to rotate in the clockwise direction, which causes the wrist of the tool 600 and jaws 610A, 610B to pitch in the clockwise direction, as shown by the arrow 695. To rotate the pulley 620 in the opposite direction, the rocker mechanism 650 is rotated in the counterclockwise direction, moving the pulley 640A toward the proximal end 680 of the tool 600 and the pulley 640B toward the distal end 670 of the tool 600. This increases the tension on cable 690A, which causes the pulley 620 to rotate in the counterclockwise direction, which in turn causes the wrist of the tool 600 and jaws 610A, 610b to pitch in the counterclockwise direction (opposite to the direction shown by arrow 695). The implementation of the lead screw and the pushrod as describe herein can allow a pitch of up to +/−90° or greater (e.g., up to a total of 180° or greater). The use of the rocker mechanism 650 results in increasing the tension of one cable (e.g., lengthening the distance one cable must travel to reach pulleys 615A, 615B), while decreasing or relaxing the tension of another cable (e.g., shortening the distance one cable must travel to reach pulleys 615A, 615B).

Figure 6A:
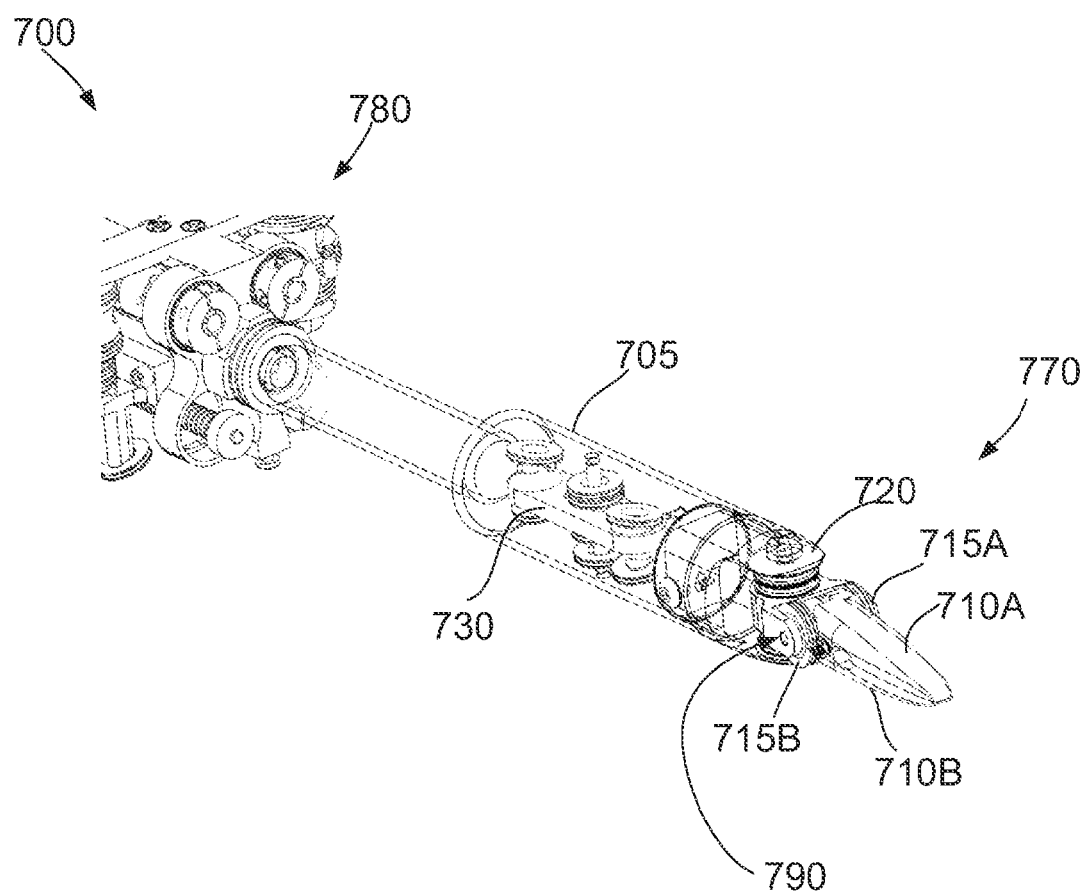
FIG. 6A illustrates a distal portion of a tool having a shuttle mechanism.

FIG. 6A shows another embodiment of a tool. The tool 700 includes a distal end 770 and a proximal end 780. The distal end 770 can be substantially similar to the distal end 31 of the tool 30 shown in FIGS. 1A-3B. The tool 700 can be actuated to move the jaws 710A, 710B in a variety of ways such as grasping (e.g., jaws rotating independently via pulleys 715A, 715B), yaw (e.g., jaws rotating together via pulleys 715A, 715B), and pitch (e.g., jaws rotating about pulley 720). The tool 700 includes a shuttle mechanism 730 which provides the pitch motion of the jaws, instead of the rocker mechanism 650 described in FIG. 5B. For clarity, the cable routing for the tool 700 is not shown in FIG. 6A. In one embodiment, the tool 700 can also include the rocker mechanism 650 to hold the rear pulleys (similar to pulleys 640A 640B) of the tool 700, and to reverse the cable routing in the proximal end (e.g., in a manner similar to how pulleys 640A, 640B reverse the cable routing toward pulleys 630A, 630B). That is, in one embodiment the proximal end of the tool 700 can have the same structure as the proximal end of the tool 600.

Figure 6B:
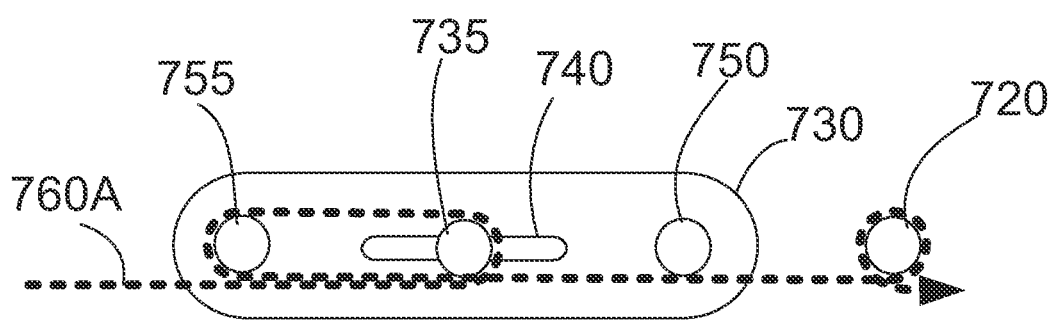
FIG. 6B schematically illustrates the cable routing of a first cable for the tool of FIG. 6A.
Figure 6B:
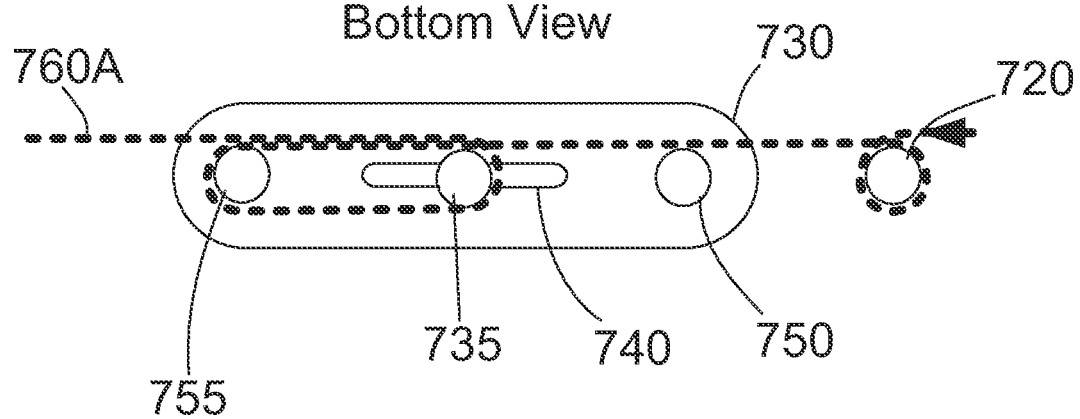

Referring now to FIG. 6B, the top view and the bottom view of the shuttle mechanism 730 with the cable routing for a first cable 760A is shown. In the illustrated embodiment, the axle of a central pulley 735 of the shuttle mechanism 730 is immovably coupled to the body of the tool shaft 705. The shuttle mechanism 730 can slide linearly back and forth along the longitudinal axis of the tool shaft 705.

Looking at the top view in FIG. 6B, the cable 760A enters the tool shaft body from the proximal end 780. The cable 760A winds at least partially around the central pulley 735. The cable 760A extends back toward the proximal end 780 and winds at least partially around shuttle pulley 755. The cable 760A then extends toward the distal end 770 and winds at least partially around a pulley 720. The pulley 720 can be substantially similar to pulley 620, described above, and can function as a wrist of the tool 700. The pulley 720 is coupled to a yoke 790 which is coupled to the jaws 710A, 710B, as shown in FIG. 6A. Looking at the bottom view in FIG. 6B, the cable 760A enters the tool shaft body from the distal end 770 after winding around the pulley 720. The cable 760A extends back toward the proximal end 780 and winds at least partially around the shuttle pulley 755. The cable 760A then extends toward the distal end 770 and winds at least partially around the central pulley 735, after which the cable 760A extends toward proximal end 780.

Figure 6C:
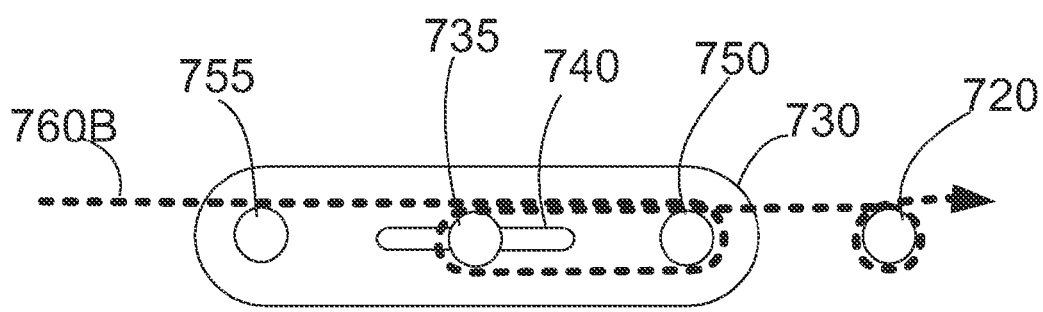
FIG. 6C schematically illustrates the cable routing of a second cable for the tool of FIG. 6A.
Figure 6C:
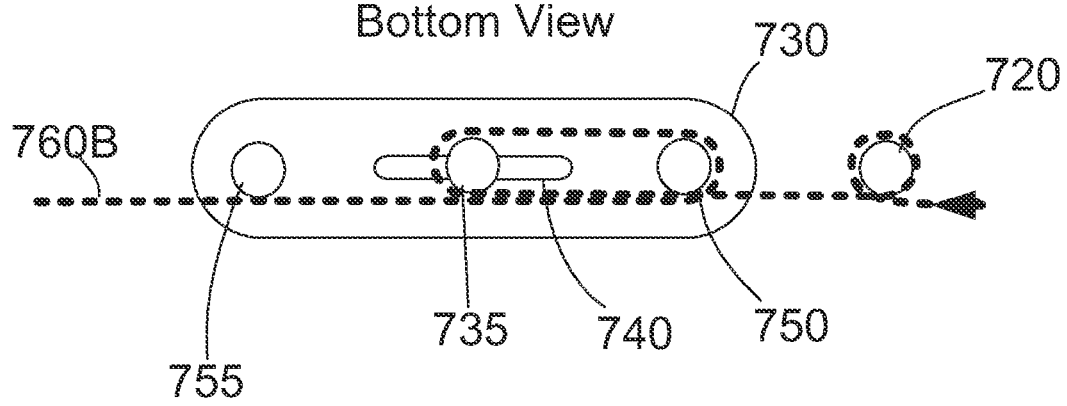

FIG. 6C illustrates the top view and the bottom view of the shuttle 730 with the cable routing for a second cable 760B. Looking at the top view in FIG. 6C, the cable 760B enters the tool shaft body 705 from the proximal end 780. The cable 760B winds at least partially around the shuttle pulley 750. The cable 760A extends back toward the proximal end 780 and winds at least partially around the central pulley 735. The cable 760A extends toward the distal end 770 and winds at least partially around the pulley 720. The pulley 720 is coupled to the yoke 790 which is coupled to the jaws 710A, 710B, as shown in FIG. 6A. Looking at the bottom view in FIG. 6C, the cable 760B enters the tool shaft body 705 from the distal end 770 after winding around the pulley 720. The cable 760B extends back toward the proximal end 780 and winds at least partially around the central pulley 735. The cable 760B then extends toward the distal end 770 and winds at least partially around the shuttle pulley 750, after which the cable 760B extends toward proximal end 780.

Figure 6D:
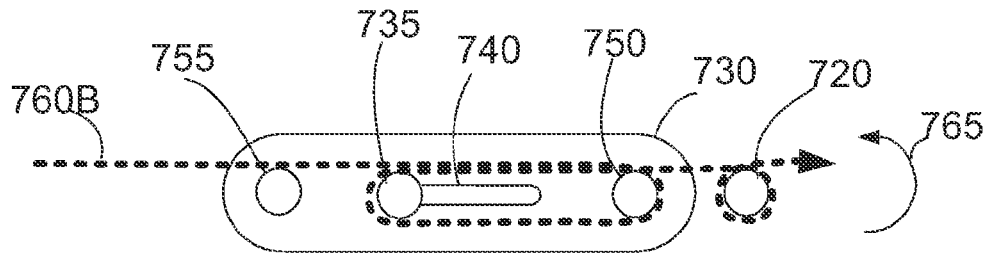
FIG. 6D schematically illustrates the shuttle mechanism.
Figure 6D:
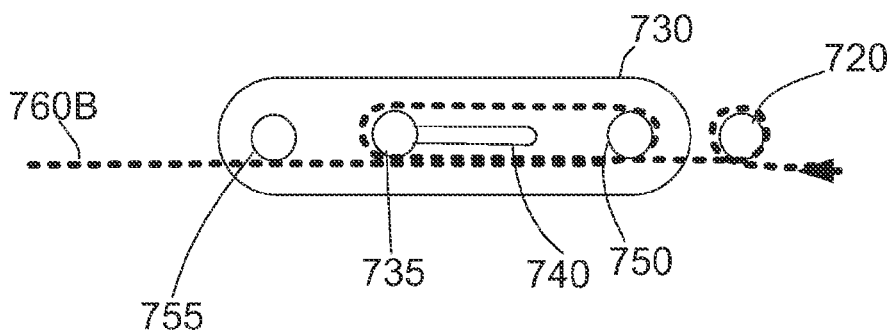
Figure 6D:
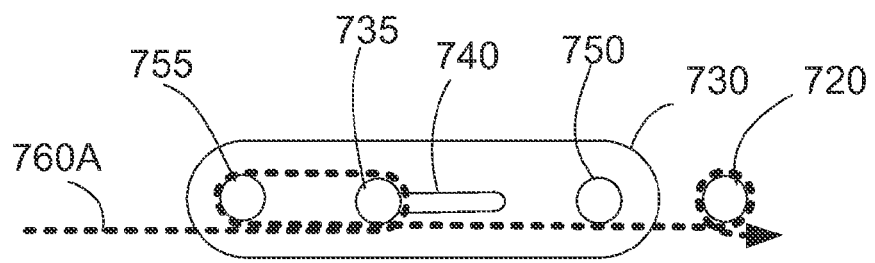
Figure 6D:
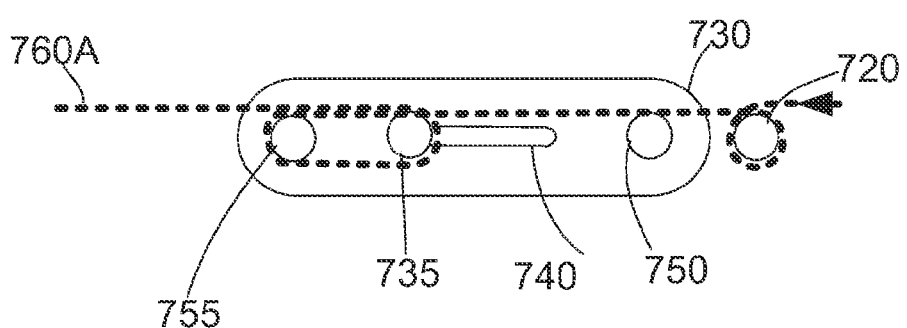

To provide pitch to the wrist and jaws 710A, 710B of the tool 700, the shuttle mechanism 730 is adjusted, changing the position of the shuttle mechanism 730 along the longitudinal axis of the tool 700. FIG. 6D shows the shuttle mechanism 730 shifted toward the distal end 770 of the tool 700. The position of the shuttle mechanism 730 is adjusted by a mechanism (e.g., a pushrod, lead screw, cable transmission) attached to a motor (e.g., motor 660D shown in FIG. 5A). FIG. 6D shows the effect of linearly translating the shuttle mechanism 730 towards the distal end 770. The top two diagrams in FIG. 6D illustrate the cable routing for cable 760B and the bottom two diagram illustrates the cable routing for cable 760A. The position of the shuttle mechanism 730 increases the tension on both sides of the cable 760B. The distance that the cable 760B has to travel to reach the pulley 720 has increased (e.g., the distance between the shuttle pulley 750 and central pulley 735 has increased), while the distance that the cable 760A has to travel to reach pulley 720 has decreased (e.g., the distance between the central pulley 735 and the shuttle pulley 755 has decreased). As a result, the tension imparted by cable 760B onto the pulley 720 increases and the tension imparted to the pulley 720 by cable 760A decreases. This tension rotates the pulley 720 in the counterclockwise direction in the direction of arrow 765. The cable routing described above can in other embodiments use alternate sets of pulleys than those described, but the use of the shuttle mechanism 730 results in increasing the tension of one cable (e.g., lengthening the distance one cable must travel to reach pulleys 715A, 715B), while decreasing or relaxing the tension of another cable (e.g., shortening the distance one cable must travel to reach pulleys 715A, 715B).

To rotate the pulley 720 (e.g., wrist pulley) in the opposite direction, the shuttle mechanism 730 is translated toward the proximal end 780 of the tool 700. This tension rotates the pulley 720 in the clockwise direction. With the shuttle positions towards the proximal end 780, the tension on cable 760A increases and the wrist (e.g., pulley 720) will pitch in the opposite direction as the arrow 765. The implementation of the shuttle mechanism 730 as describe herein can allow a pitch of up to +/−90° or greater (e.g., up to a total of 180° or greater).

As described above, the rocker mechanism 650 and shuttle mechanism 730 increase the tension on a first cable and release the tension on a second cable. The rocker mechanism 650 and shuttle mechanism 730 can be used to effect movement of one pulley 620, 720 or any combination of pulleys (e.g., the pulleys shown in FIG. 1A).

Figure 7A:
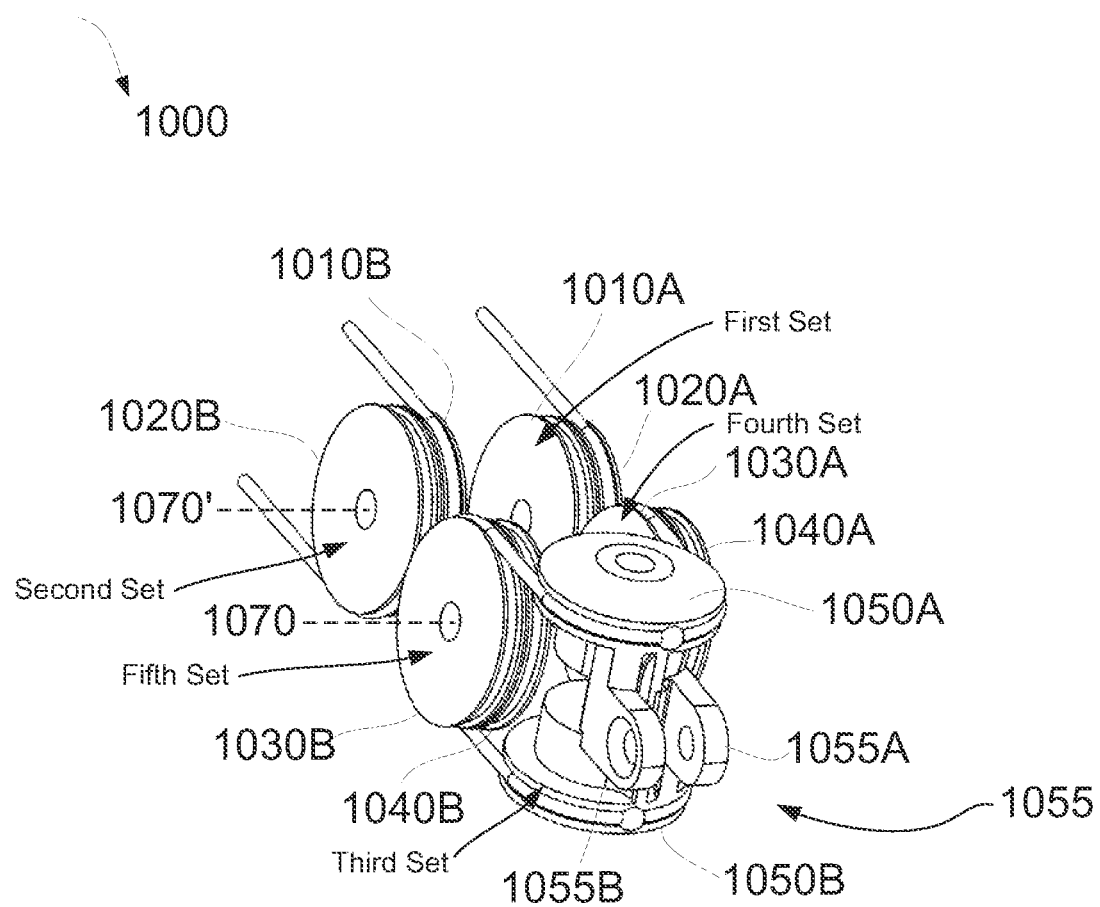
FIG. 7A illustrates an embodiment of a wrist.

FIG. 7A shows another embodiment of a tool. The tool 1000 has ten pulleys, 1010A, 1010B, 1020A, 1020B, 1030A, 1030B, 1040A, 1040B, 1050A, 1050B. The pulleys 1010A, 1020A are arranged in a first set. The pulleys 1010B, 1020B are arranged in a second set. The pulleys 1050A, 1050B are arranged in a third set. The third set of pulleys can be angled relative the first set of pulleys and/or the second set of pulleys.

The pulleys 1030A, 1040A are arranged in a fourth set. The pulleys 1030B, 1040B are arranged in a fifth set. The third set of pulleys can be angled relative the fourth set of pulleys and/or the fifth set of pulleys. In the illustrated embodiment, the first set of pulleys 1010A, 1020A can be in series with the fourth set of pulleys 1030A, 1040A. The second set of pulley 1010B, 1020B can be in series with the fifth set of pulley 1030B, 1040B. The first set of pulleys 1010A, 1020A can be arranged along an axis of rotation with the second set of pulleys 1010B, 1020B. The fourth set of pulleys 1030A, 1040A can be arranged along an axis of rotation with the fifth set of pulleys 1030B, 1040B. Other arrangements of the pulleys 1010A, 1010B, 1020A, 1020B, 1030A, 1030B, 1040A, 1040B are possible.

Figure 7B:
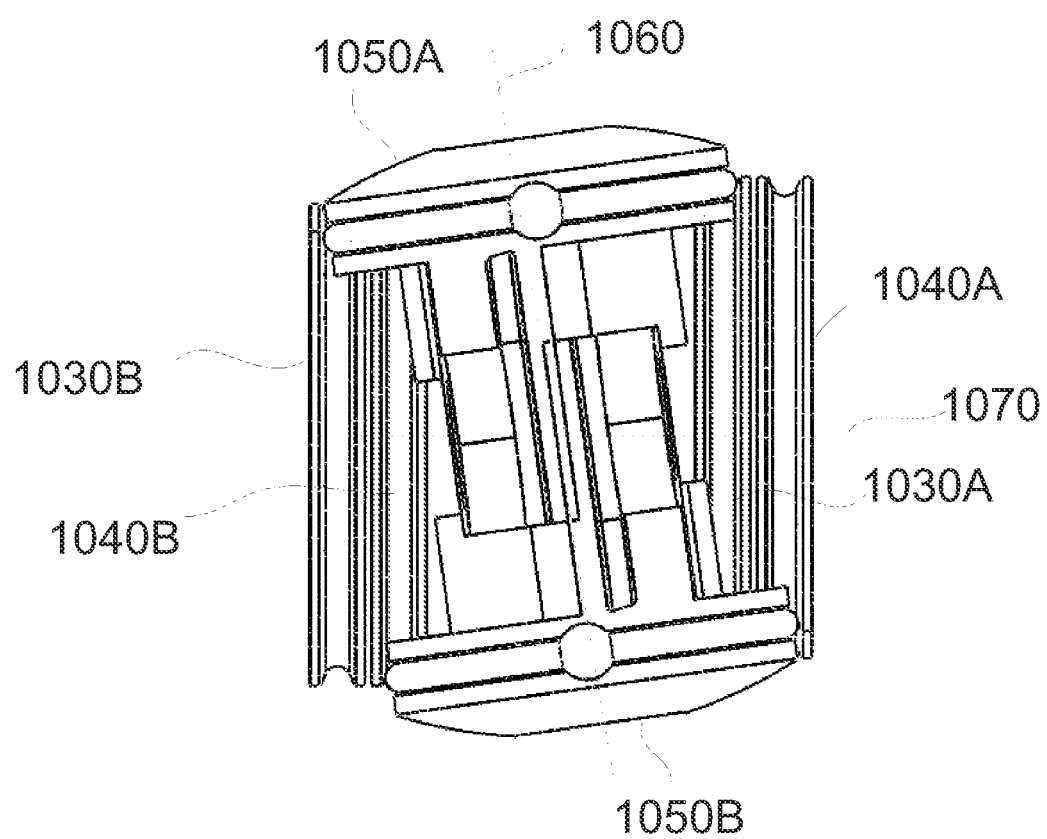
FIG. 7B illustrates a front view of the wrist of FIG. 7A.

Referring to FIG. 7B, the third set of pulleys 1050A, 1050B can be arranged along an axis of rotation 1060. The fourth set of pulleys 1030A, 1040A and the fifth set of pulleys 1030B, 1040B can be arranged along an axis of rotation 1070. The axis of rotation 1060 of third set of pulleys 1050A, 1050B can be angled relative to the axis of rotation 1070 of the fourth set of pulleys 1030A, 1040A and the fifth set of pulleys 1030B, 1040B such that the grooves on pulleys 1030B and 1040A are aligned with the grooves on pulleys 1050A and 1050B, respectively, thereby allowing the cables to follow a straight path between the pulleys 1030B and 1040A and the pulleys 1050A, 1050B to reduce cable bending and friction between the cables and pulleys.

The first set of pulleys 1010A, 1020A and the second set of pulleys 1010B, 1020B can be arranged along an axis of rotation 1070', shown in FIG. 7A. The axis of rotation 1060 of the third set of pulleys 1050A, 1050B can be angled relative to the axis of rotation 1070' of the first set of pulleys 1010A, 1020A and the second set of pulleys 1010B, 1020B.

The routing of a first cable and a second cable is shown in FIG. 7A. The pulleys 1050A, 1050B are coupled to a yoke 1055. The yoke 1055 can have two attachments 1055A, 1055B extending from a surface of the yoke 1055. In one embodiment, the jaws of the tool 1000 can be coupled to the pulleys 1050A, 1050B via the attachments 1055A, 1055B. The cable routing can be similar to the routing described with respect to FIGS. 1A-3B. Each cable winds at least partially around one pulley in the fourth set of pulleys 1030A, 1040A, and one pulley in the fifth set of pulleys 1030B, 1040B, as shown. In some embodiments, the angle of the third set of pulleys 1050A, 1050B is arranged such that the cables from and to the fourth set of pulleys 1030A, 1040A and the fifth set of pulleys 1030B, 1040B follow a straight path to the third set of pulleys 1050A, 1050B. The tool 1000 can be actuated to move the jaws (not shown) in a variety of ways such as grasping (e.g., jaws rotating independently via pulleys 1050A, 1050B), yaw (e.g., jaws rotating together via pulleys 1050A, 1050B), and pitch (e.g., jaws rotating about pulleys 1030A, 1040A, 1030B, 1040B).

In other embodiments, a tool can include a rigid portion and a flexible portion, where the flexible portion can selectively be made rigid and/or locked into place to thereby effect a bent configuration to at least a portion of the tool. In some embodiments, said flexible portion that can be selectively made rigid can be disposed proximal of a wrist of the tool, where the wrist of the tool can have any configuration disclosed in the embodiments herein. Accordingly, in some embodiments, a tool can have a wrist and a flexible portion proximal of the wrist that provides another joint that can be actuated to position an end effector of the tool at different orientations, thereby advantageously increasing the range of motion of the distal end of the tool.

Figure 8A:
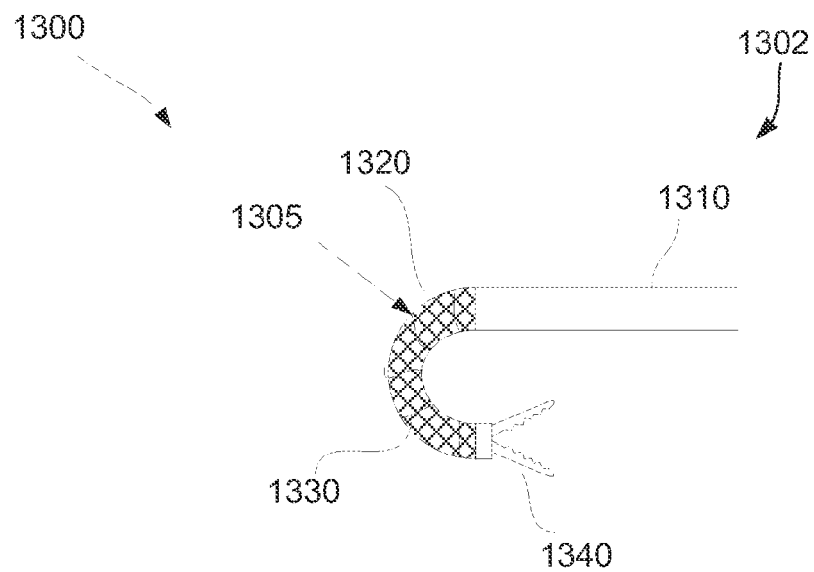
FIG. 8A illustrates embodiment of a tool with a flexible section.

FIGS. 8A-9C show embodiments of a flexible section which may be incorporated into tools described herein. FIG. 8A shows another embodiment of a tool. The tool 1300 can include a bend or elbow along a portion of the tool shaft 1302. The tool 1300 can include one or more rigid sections 1310. The tool 1300 includes one or more flexible sections 1305. The flexible section 1305 can include a sheath 1320, which is shown in cross-hatching. The tool 1300 can include an end effector 1340 (e.g., a grasper). The tool 1300 can be bent or otherwise manipulated to attain a nonlinear configuration, such as to reach around obstacles to a desired position or object. Further, the tool 1300 can be arranged such that the flexible section 1305 can selectively be made rigid and/or locked in place (e.g., to maintain said bent configuration).

In some embodiments, when used in surgical applications, the tool 1300 can be inserted through a trocar. Since trocars generally have a straight configuration, the tool 1300 can be arranged to extend along a longitudinal axis (e.g., straight, rigid) for insertion through the trocar. The tool 1300 can be bent or manipulated after exiting the trocar and into the body (e.g., when the tool is used in percutaneous surgery) to assume a shape other than straight. Once the desired shape has been obtained, the tool 1300 can be locked into position in order to rigidly maintain the bent shape. The locking of the tool 1300 may prevent the user from losing control of the position of the tool 1300.

Figure 8B:
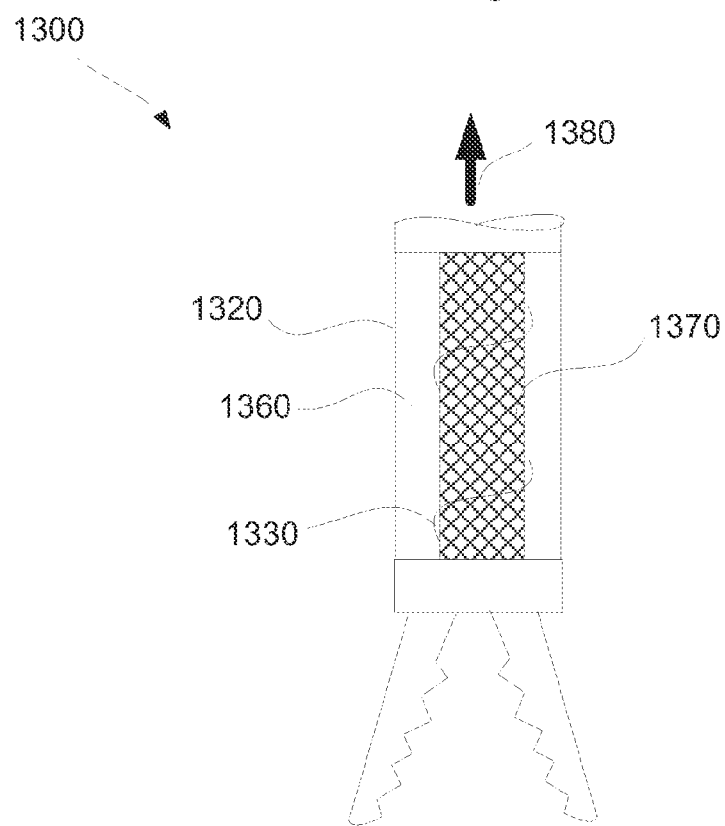
FIG. 8B illustrates the flexible section of FIG. 8A.

FIG. 8B shows the flexible section 1305 in greater detail. In one embodiment, the flexible section 1305 can include a flexible core (e.g., a braid) 1370. The flexible section 1305 can include a container 1360 which can be flexible. The container 1360 can include a low-melting point material (e.g., wax, polymer) which has both a solid state and a liquid state. In one embodiment, the flexible core (e.g., braid) 1370 can include a conductive material of filaments impregnated with a matrix of the low-melting point material. The transition between the solid state and the liquid state occurs at a low-temperature (e.g. less than 150 degrees F., less than 140 degrees F., less than 130 degrees F., less than 120 degrees F., less than 110 degrees F., less than 100 degrees F., less than 90 degrees F., etc.). The container 1360 can be surrounded by a sheath 1320. The arrow 1380 represents the cables to actuate the end effector, such as the electrical wire to actuate the flexible sheath 1320 that travel toward the proximal end of the tool 1300.

With continued reference to FIGS. 8A-8B, the low-melting point material can become fluid when activated by an activation mechanism. The low-melting point material can become solid when not activated. The activation mechanism can include a heating element 1330, which applies heat to the low melting point material. In one embodiment, the heating element 1330 can apply heat when an electric current is passed through the heating element (e.g., the heating element can be a resistive heater). In other embodiments, other rigidizing mechanisms based on electrostatic effect or magnetic effects may be used instead of, or in addition to, low melting point solids.

When the heating element 1330 is turned on, the low-melting point material transitions to a fluid state and becomes flexible. The tool 1300 can be bent or manipulated.

When the heating element 1330 is turned off, the low-melting point material transitions to a solid state and becomes rigid. The tool 1300 can maintain its bent position.

Figure 8C:
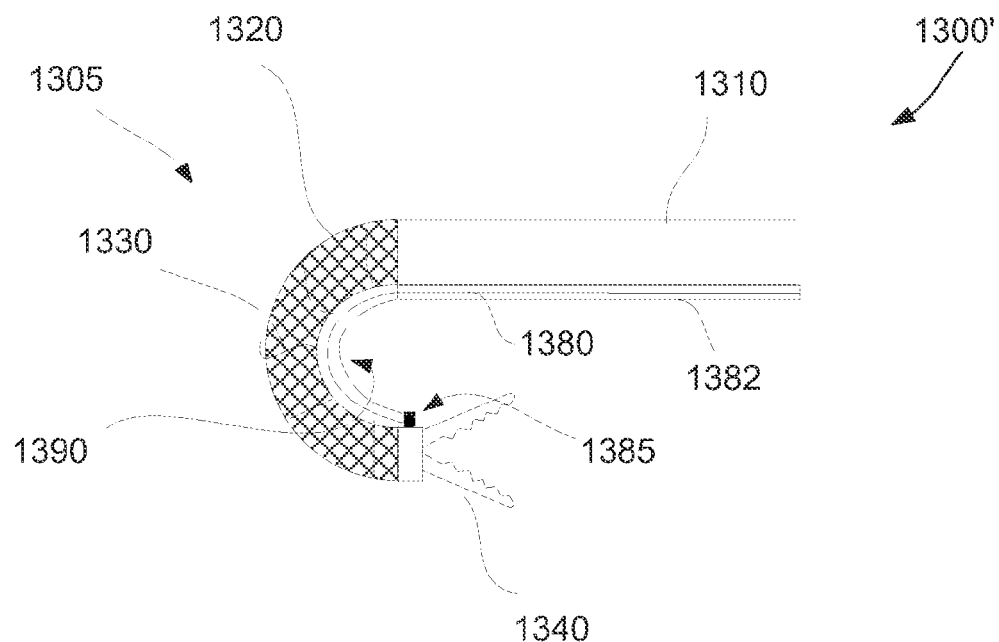
FIG. 8C illustrates an embodiment of a flexible section.

FIG. 8C shows an embodiment of the flexible section 1305 of a tool 1300'. This configuration can be considered an active elbow configuration. The tool 1300' can include a cable 1380. The cable 1380 can be enclosed by a housing 1382. The housing 1382 can be flexible to bend with the flexible section 1305. The tool 1300' can include one or more cables. The tool 1300' can include two or more cables. The cable 1380 can be attached to the one or more rigid sections 1310, the one or more flexible sections 1305, and/or the end effector 1340. The cable 1380 can be coupled to the distal end of the flexible section 1305, (e.g., to a distal location 1385). In some embodiments, the heating element 1330 is actuated and the flexible section 1305 becomes malleable. The cable 1380 is tensioned and the flexible section 1305 is tensioned to form a bend via the cable 1380 pulling on the distal location 1385 of the flexible section 1305, thereby providing an active elbow. When an appropriate or desired bend of the flexible section 1305 is obtained, the activation element may be deactivated. The flexible section 1305 becomes rigid and the bend would be locked into position. The low-melting point material would harden and maintain the position of the flexible section 1305.

Figure 8D:
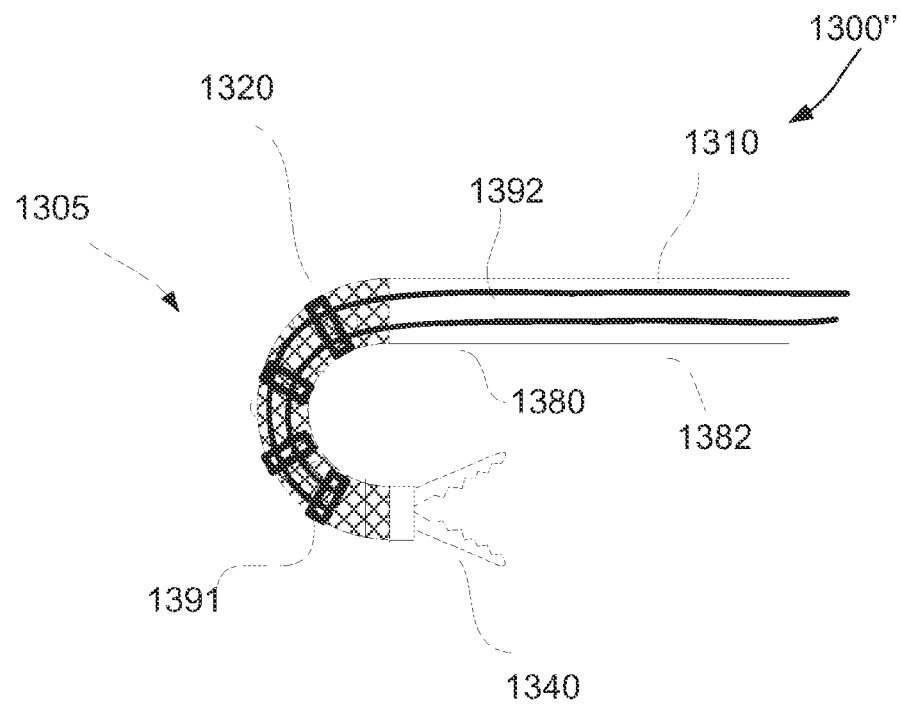
FIG. 8D illustrates an embodiment of a flexible section.

FIG. 8D shows an embodiment of the flexible section 1305 of a tool 1300". This configuration can be considered a passive elbow configuration. The flexible section 1305 can include one or more vertebra 1391 (e.g., one, two, three, four, five, six vertebrae, etc.). The vertebrae 1391 can be any cross-sectional shape (e.g., circular, disc). The vertebra 1391 are retained within or covered by the sheath 1320. The flexible section 1305 can include a flexible core (e.g., a braid), such as braid 1370 in FIG. 8B. Similar to the tool 1300 in FIG. 8B, the flexible section 1305 can include a container 1360 which can be flexible and can include a low-melting point material (e.g., wax, polymer) which has both a solid state and a liquid state and can transition between the solid state and the liquid state occurs at a low-temperature, such as the temperatures noted above.

The tool 1300" can include a cable 1392. The cable 1392 can be enclosed by a housing (not shown). The tool 1300" can include one or more cables 1392. The tool 1300" can include two or more cables 1392. The cable 1392 can be attached to the one or more rigid sections 1310, the one or more flexible sections 1305, one or more vertebra 1391 and/or the end effector 1340. The cable 1392 can extend within the tool 1300", as shown in FIG. 8D.

In some embodiments, the heating element 1330 is actuated and the flexible section 1305 becomes malleable. The cable 1392 is tensioned, which changes the orientation of the one or more vertebra 1391 to form a bend in the flexible section 1305. The bending of the flexible section 1305 originates from the one or more vertebrae 1391 which form part of the flexible section 1305. The flexible section 1305 and/or flexible sheath 1320 simply follow the bend of the one or more vertebrae 1391, thereby providing a passive elbow. When an appropriate or desired bend of the flexible section 1305 is obtained, the activation element 1330 may be deactivated. The flexible section 1305 becomes rigid and the bend would be locked into position. The low-melting point material would harden and maintain the position of the flexible section 1305.

Figure 9A:
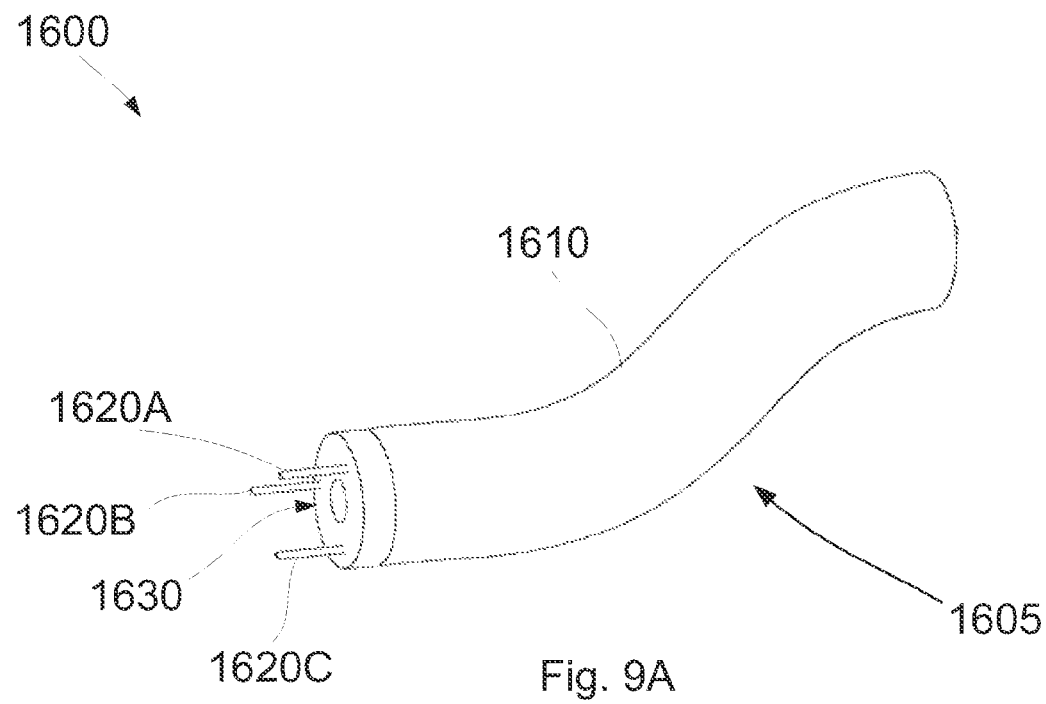
FIG. 9A illustrates an embodiment of a flexible section.

FIG. 9A shows another embodiment of a tool. The tool 1600 includes a sheath 1610. The sheath 1610 can be formed from a flexible material (e.g., cast silicon rubber). The tool 1600 can include one or more control cables 1620A, 1620B, 1620C. Three control cables are shown in FIG. 9A, but any number of control cables can be utilized (e.g., one, two, three, four, five, six cables, etc.). The control cables 1620A, 1620B, 1620C are coupled to a mechanism (not shown) for manipulating the curvature of the flexible section 1605. The three control cables 1620A, 1620B, 1620C can extend through the flexible section 1605 and exit the proximal end of the flexible section 1605. The tool 1600 can include an instrument channel 1630. The instrument channel 1630 can extend along a longitudinal axis of the tool 1600. The instrument channel 1630 can extend along then entire tool 1600 or a portion of the length of the tool 1600. The instrument channel 1630 can include a control mechanism (not shown) for manipulating the end effector and/or other components (e.g., electrical wires, safety wires).

In one embodiment, the sheath 1610 can be disposed proximal of a wrist of the tool 1600, where the wrist can have one of the configurations disclosed herein (e.g., the pulley system in FIGS. 1A-3B). The sheath 1610 can thus provide an additional joint to increase a range of motion of a distal end of the tool 1600. In some embodiments, the control cables that manipulate the curvature of the flexible section 1605 of the sheath 1610 can also effect movement of the wrist of the tool (e.g., the distal end 31 of tool 30 in FIGS. 1A-3B).

Figure 9B:
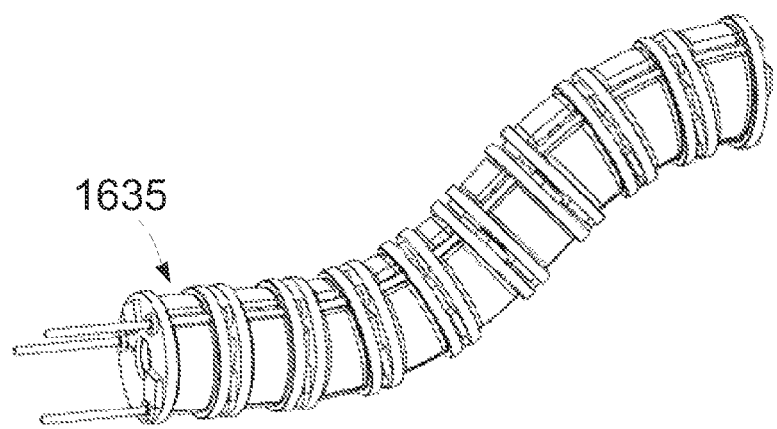
FIG. 9B illustrates the flexible section of FIG. 9A.

FIG. 9B shows the tool 1600 with the sheath 1610 removed. The tool 1600 can include one or more vertebrae 1635 (e.g., one, two, three, four, five, six vertebrae, etc.). The one or more control cables 1620A, 1620B, 1620C can extend through the one or more vertebrae 1635. The orientation of each vertebra 1635 may be controlled by the control cables 1620A, 1620B, 1620C.

Figure 9C:
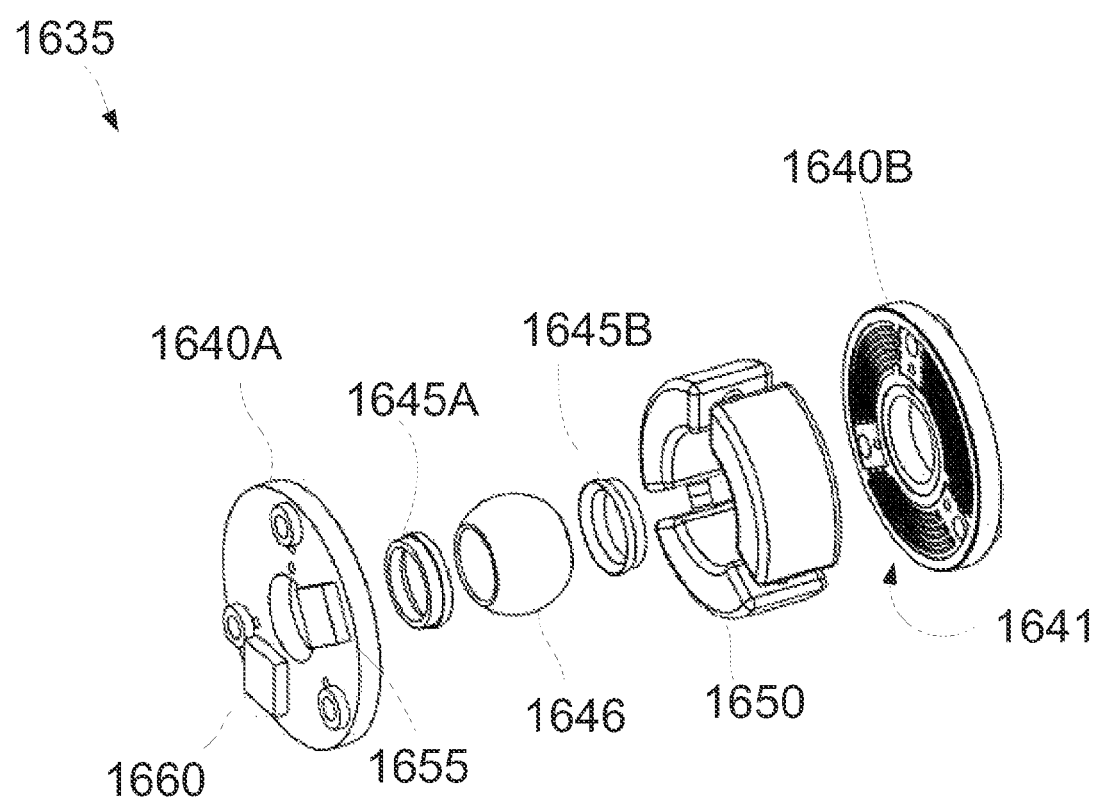
FIG. 9C illustrates a vertebra of a flexible section.

FIG. 9C shows an exploded view of a vertebra 1635. The vertebra 1635 can include one or more printed circuit boards 1640A, 1640B. The vertebra 1635 can include two printed circuit boards 1640A, 1640B disposed on either side of the vertebra 1635. The two printed circuit boards 1640A, 1640B can be identical. The two printed circuit boards 1640A, 1640B can include a heating element 1641 on one side of the printed circuit boards, as shown on printed circuit board 1640B. The two printed circuit boards 1640A, 1640B can include components on other side of the printed circuit boards, as shown on printed circuit board 1640A. The components can include a switch 1655 (e.g., an addressable micro-switch). The switch 1655 selects which vertebra to turn on. The components can include a relay or FET 1660 for turning the heating element 1641 on and off. The relay of FET 1660 provides the power source for the heating elements 1641. In other embodiments, other rigidizing mechanisms based on electrostatic effect or magnetic effects may be used instead of, or in addition to, low melting point solids. One or more electrical wires (not shown) connect the two printed circuit boards 1640A, 1640B to other components for various functions (e.g. power, data transmission). The switch 1655 and the relay 1660 may be combined into one component. The switch 1655 and/or the relay or FET 1660 can be replaced with other mechanism for activating/deactivating an element known in the art.

The vertebra 1635 can include a spherical spacer ball 1646. The spherical spacer ball 1646 can be retained in ball seats 1645A, 1645B. The ball seats 1645A, 1645B can be coupled with the printed circuit boards 1640A, 1640B. The ball seats 1645A, 1645B can maintain a pre-determined distance between each other. The vertebra 1635 can include a spacer 1650. The spacer 1650 can be formed from a low-melting point material (e.g., metal) which has both a solid state and a liquid state. The transition between the solid state and the liquid state occurs at a low-temperature (e.g. less than 150 degrees F., less than 140 degrees F., less than 130 degrees F., less than 120 degrees F., less than 110 degrees F., less than 100 degrees F., less than 90 degrees F., etc.). At room temperature, the spacer 1650 can be solid. The low-melting point material can be encapsulated by a container (e.g. silicon cast around the low-melting point material). The spacer 1650 is positioned between the two printed circuit boards 1640A, 1640B. The spherical spacer ball 1646 is retained within the spacer 1650.

To position the tool 1600, a data signal is sent to the two printed circuit boards 1640A, 1640B of a selected vertebra. The data signal can be sent to one selected vertebra 1635 or more than one selected vertebra 1635. The data signal causes the pair of heating elements 1641 of the selected vertebra 1635 to be activated. The control cables 1620A, 1620B, 1620C can be tensioned to create a bend and/or any angular orientation between the two printed circuit boards 1640A, 1640B in the selected vertebra 1635 may be obtained.

The data signal can cause the pair of heating elements 1641 of the selected vertebra 1635 to be deactivated. This turns off the heating elements 1641, allowing the low-melting point material to solidify at an orientation (e.g., position and/or angle) set by the control cables 1620A, 1620B, 1620C. In one embodiment, control cables 1620A, 1620b, 1620C can maintain the position and/or angle of the selected vertebra 1635 until the low-melting point material solidifies. In some embodiments, a coolant may be directed through the instrument channel 1630 to accelerate solidification and/or cooling of the low-melting point material. By activating and setting the angles of selected vertebra 1635 and groups of selected vertebra 1635, compound curves can be achieved as shown in FIG. 9B.

Figure 10:
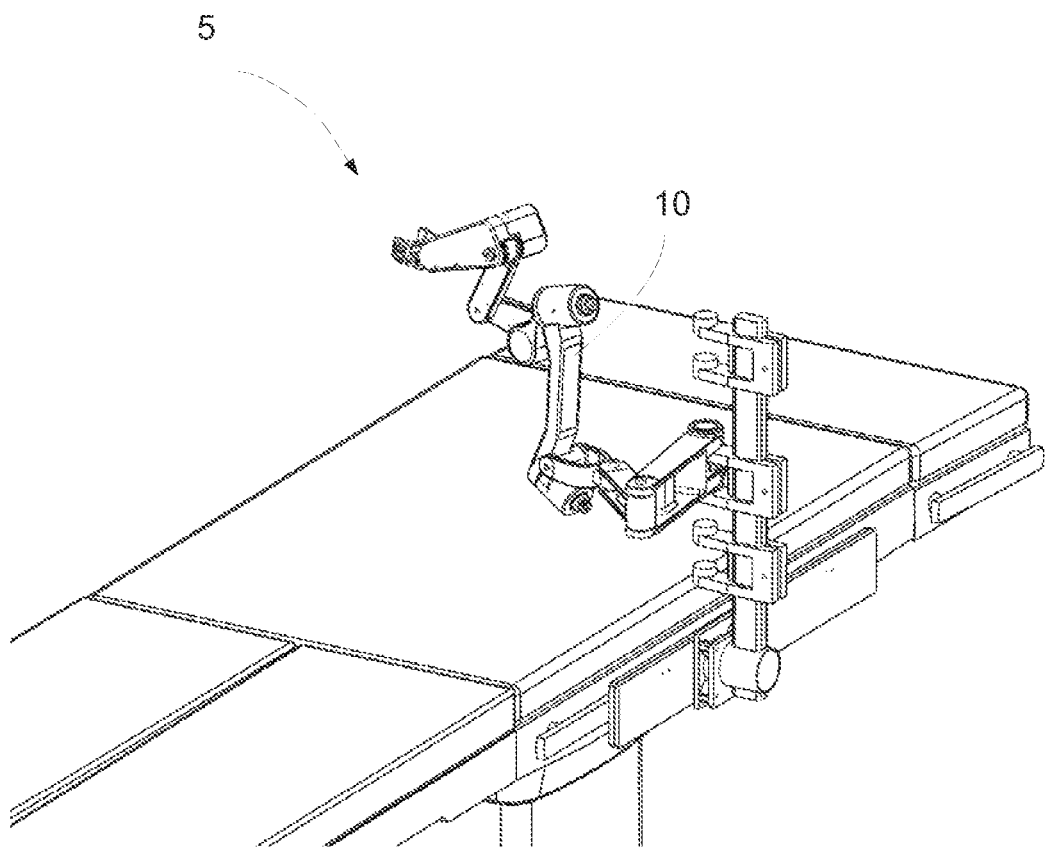
FIG. 10 illustrates a hyperdexterous surgical system.

Several concepts are now described that are advantageous for surgical systems, although these concepts can also provide advantages in non-surgical and non-medical applications. FIG. 10 shows an embodiment of a hyperdexterous surgical system 5 that can be used to perform surgical procedures (e.g., percutaneous minimally invasive surgical procedures). The hyperdexterous surgical system 5 can include one or more hyperdexterous surgical arms 10. In some embodiments, a surgical procedure is performed by manipulating a tool (e.g., any of the tools described herein), for example by manipulating a tool held by the hyperdexterous surgical arm 10.

Figure 11:
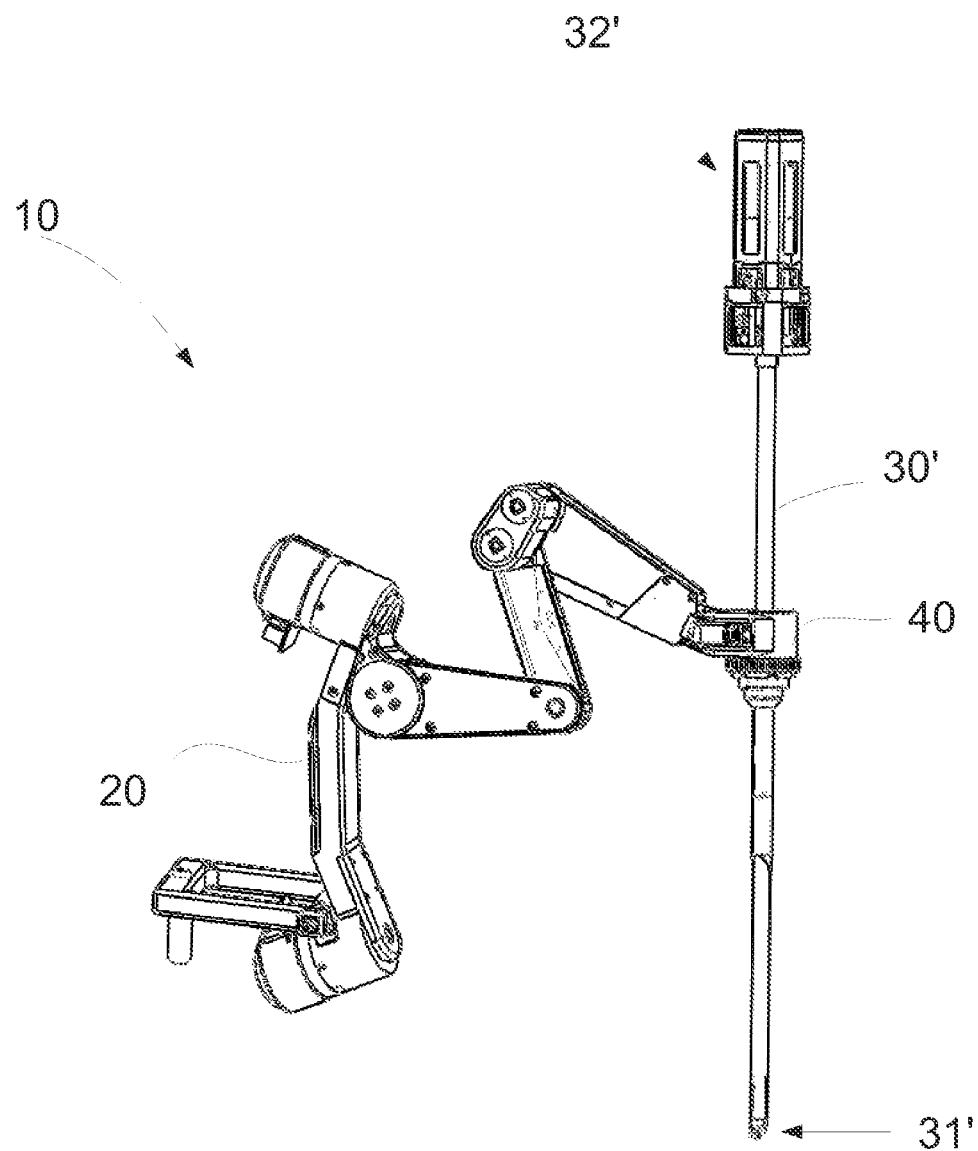
FIG. 11 illustrates a hyperdexterous surgical arm coupled to a hyperdexterous surgical tool.

FIG. 11 shows an embodiment of the hyperdexterous surgical arm 10. The hyperdexterous surgical arm 10 can be coupled to a hyperdexterous surgical tool 30'. The tool will be variably called a "hyperdexterous surgical tool" or simply the "tool". The hyperdexterous surgical tool 30' includes a distal end 31' and a proximal end 32'. In one embodiment, the hyperdexterous surgical tool 30' and distal end 31' can be similar to the tool 30 and distal end 31 in FIGS. 1A-3B. In use, the distal end 31' may be placed within the body of a patient through an incision (e.g., in a percutaneous minimally invasive surgical procedure). The distal end 31' of the tool 30' can include an end-effector (e.g., a grasper, such as the grasper 310 in FIG. 1A). The end-effector may be selected based on the surgical procedure or task to be performed. The distal end 31' of the tool 30' can include a wrist, the details of which are further described herein. Several concepts for improved design of the wrist of a tool, such as tool 310 in FIG. 1A, have been discussed above. Several concepts are now described that are advantageous for surgical systems, but that could also apply to non-surgical systems as well.

The hyperdexterous surgical system 5 and the hyperdexterous surgical arm 10 are further described in commonly owned, co-pending applications PCT/US2014/26115 filed Mar. 13, 2014, U.S. Provisional Application No. 61/791,248 filed Mar. 15, 2013, U.S. Provisional Application No. 61/906,802 filed Nov. 20, 2013, U.S. Provisional Application No. 61/908,888 filed Nov. 26, 2013, U.S. Provisional Application No. 61/915,403 filed Dec. 12, 2013, and U.S. Provisional Application No. 61/935,966 filed Feb. 5, 2014, all of which are hereby incorporated by reference in their entirety and should be considered a part of this specification.

Figure 12A:
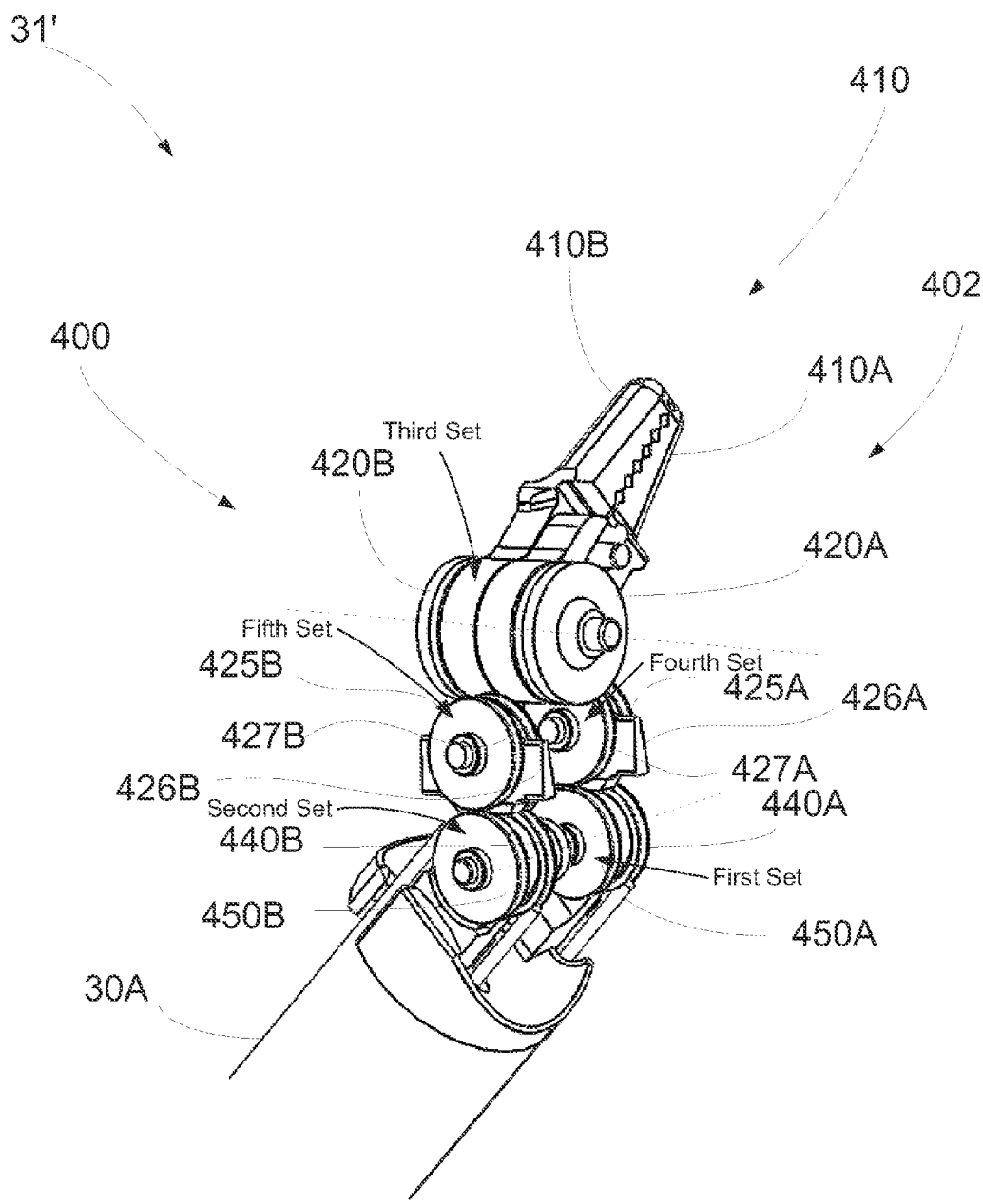
FIG. 12A illustrates a distal end of an embodiment of a tool including a wrist and an end effector.

FIG. 12A shows another embodiment of a tool. The tool 400 can be substantially similar to the tool 30 shown in FIGS. 1A-3B. The tool 400 can have a wrist 402 at a distal end 31' of the tool 400, where the wrist 402 couples an end effector 410 to a shaft 30A of the tool 400. In the illustrated embodiment, the wrist 402 can include pulleys 440A, 440B, 450A, 450B, 425A, 427A, 425B, 427B, 420A and 420B. The pulleys 440A, 450A are arranged in a first set. The pulleys 440B, 450B are arranged in a second set. The pulleys 420A, 420B are arranged in a third set. The pulleys 425A, 427A are arranged in a fourth set. The pulleys 425B, 427B are arranged in a fifth set. The third set of pulleys 420A, 420B are substantially similar to the third set of pulleys 320A, 320B discussed above with respect to FIG. 3A, and couple to jaws 410A, 410B of the end effector 410, respectively. Similarly, the first set of pulleys 440A, 450A and the second set of pulleys 440B, 450B are substantially similar to the first set of pulleys 340B, 350B and the second set of pulleys 340A, 340B discussed above with respect to FIG. 3A. The tool 400 differs from the tool 30 in FIG. 3A in that it includes two additional sets of pulleys, the fourth set of pulleys 425A, 427A and the fifth set of pulleys 425B, 427B.

Figure 12B:
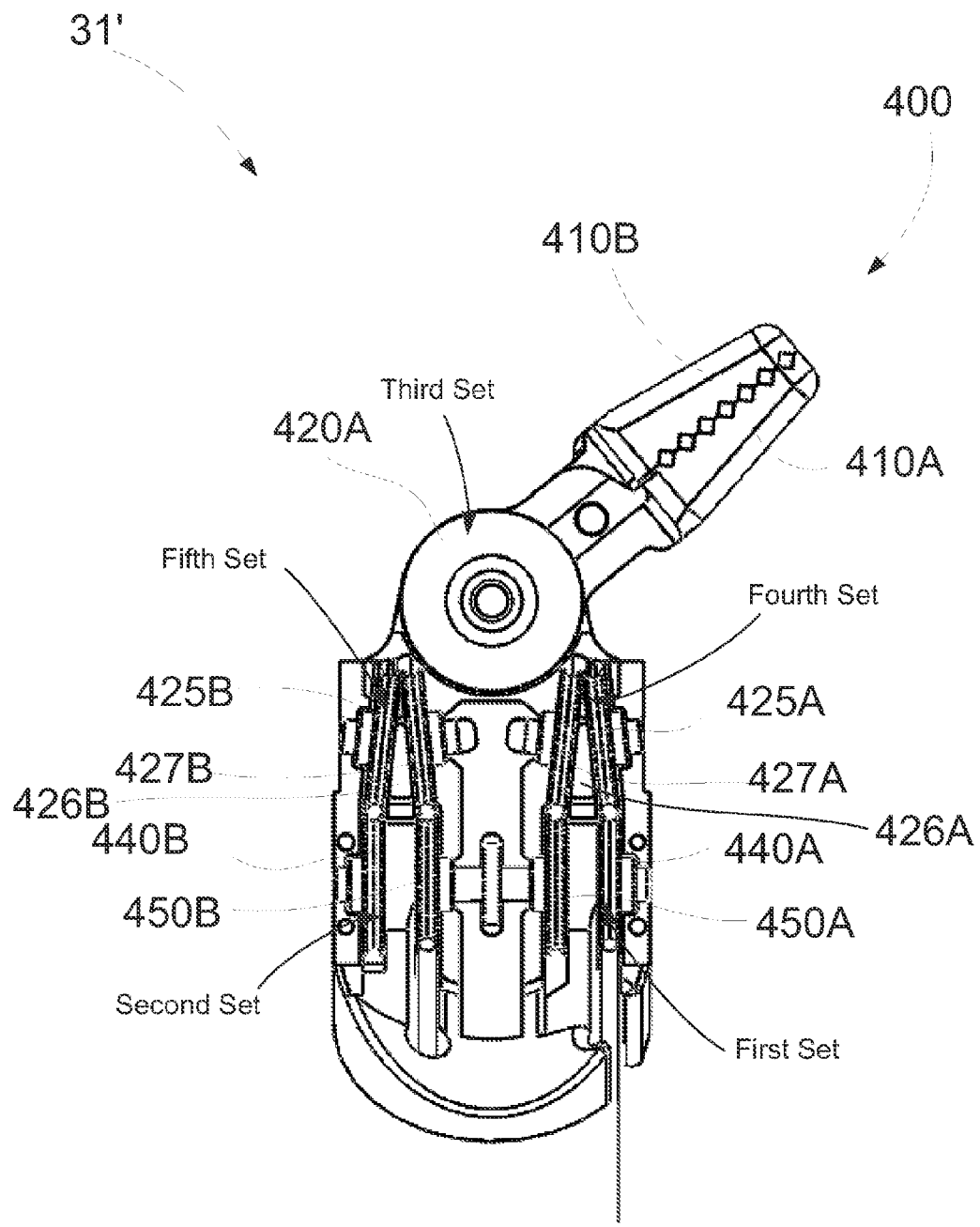
FIG. 12B illustrates the tool of FIG. 12A.

As shown in FIG. 12B, the fourth set of pulleys 425A, 427A and the fifth set of pulleys 425B, 427B are angled relative to the first set of pulley 440A, 450A and the second set of pulleys 440B, 450B. The rotational axis of pulley 425A is angled relative to the rotational axis of the pulley 440A. The rotational axis of pulley 427A is angled relative to the rotational axis of the pulley 450A. The rotational axis of pulley 425B is angled relative to the rotational axis of the pulley 440B. The rotational axis of pulley 427B is angled relative to the rotational axis of the pulley 450B.

Figure 12C:
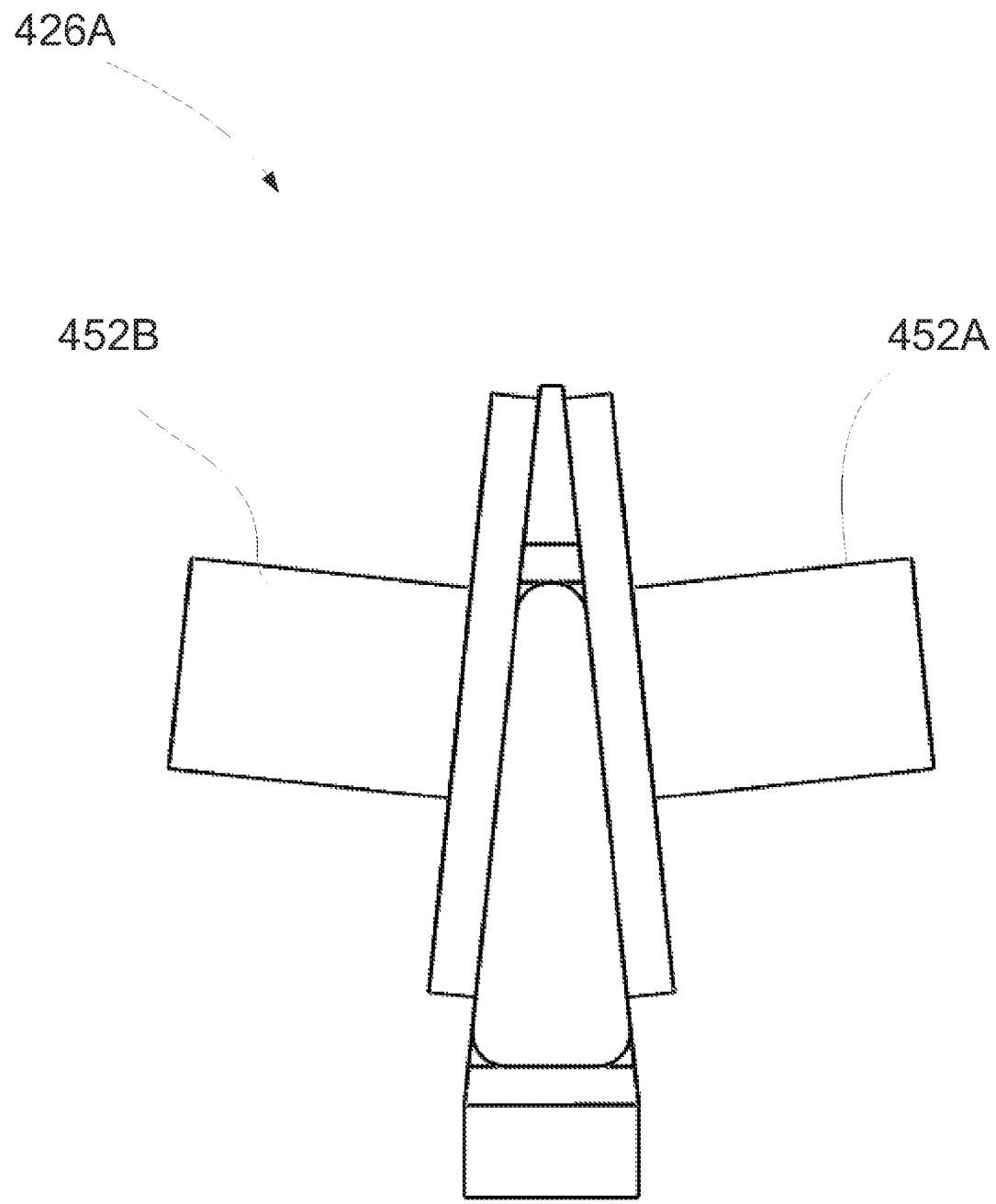
FIG. 12C illustrates an angled wedge that supports the angled pulleys of the tool of FIG. 12A.

With reference to FIG. 12C, the fourth set of pulleys 425A, 427A is maintained at an angle by an angled wedge 426A, which can include two axles 452A, 452B that extend at an angle relative to each other (e.g., 15 degrees, 30 degrees, 45 degrees, etc.). The angled axles 452A, 452B support the fourth set of pulleys 425A, 427A thereon so that the pulleys 425A, 427A can rotate about the axles 452A, 452B. In a similar manner, the fifth set of pulleys 425B, 427B can be maintained at an angle by an angled wedge 426B, as best shown in FIG. 12B. The angled wedge 426B is substantially similar to the angled wedge 426A. The design of the wrist 402, as illustrated in FIGS. 12A-12C and discussed above, decreases the cross over and friction between the cables that are routed around the pulleys of the wrist 402, thus making the routing of the cables more advantageous. The routing of the cables of the wrist 402 is further described below.

Figure 13A:
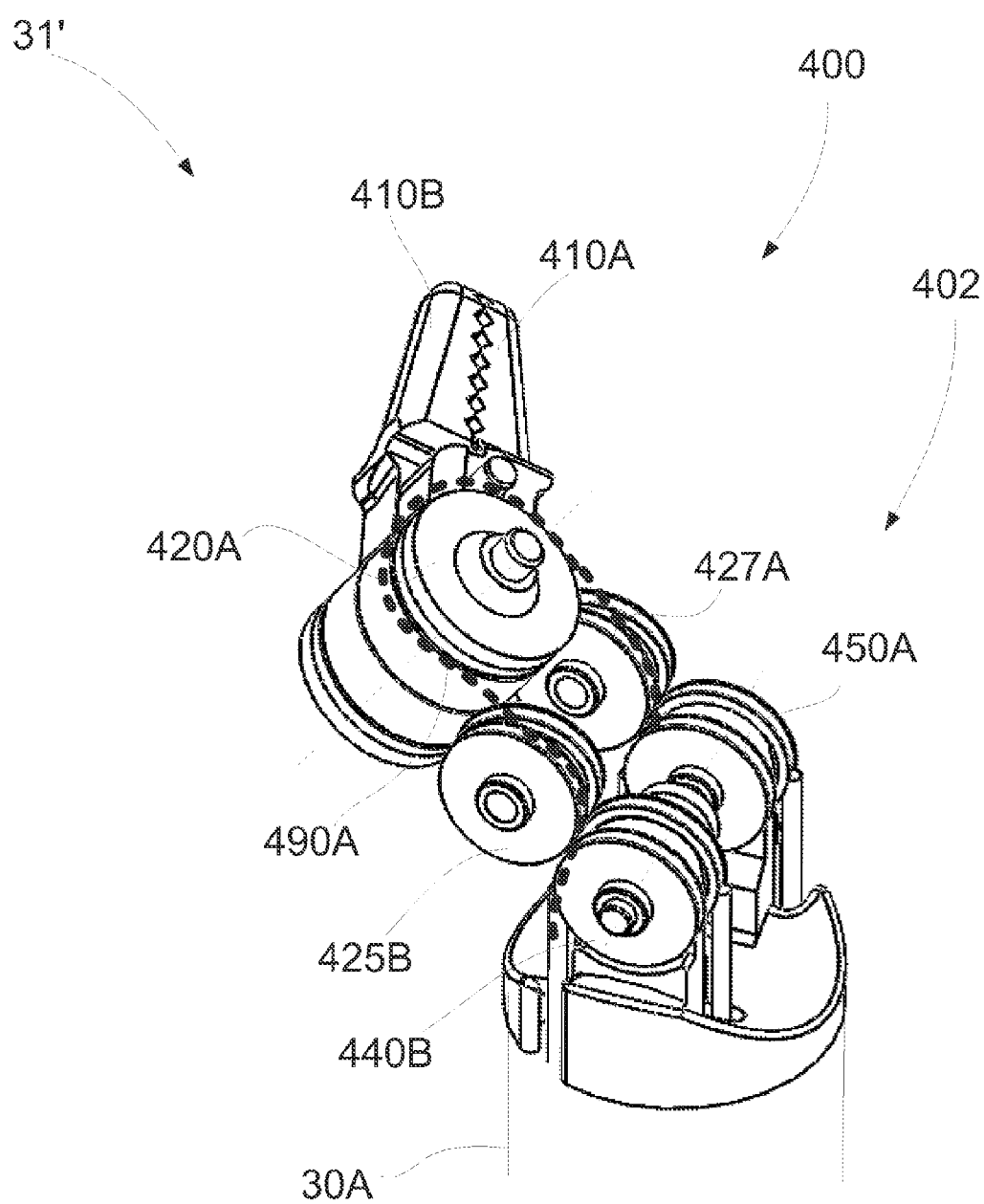
FIG. 13A illustrates the routing of a first cable of the tool of FIG. 12A.

The tool 400 can be actuated to move the jaws 410A, 410B in a variety of ways such as grasping (e.g., jaws rotating independently via pulleys 420A, 420B), yaw (e.g., jaws rotating together via pulleys 420A, 420B), and pitch (e.g., jaws rotating about pulleys 440A, 450A, 440B, 450B). FIG. 13A shows the routing of a first cable 490A in the wrist 402 of the tool 400. The first cable 490A originates in the proximal end (not shown) of the tool 400 and extends through the tool shaft 30A and out of the tool shaft 30A (e.g., through a yoke attached to the end of the shaft 30A, such as through an aperture or hole), in a similar manner as described previously in connection with the tool 30 illustrated in FIG. 3A. In the illustrated embodiment, the first cable 490A winds at least partially around one pulley in the first set of pulleys 440A, 450A. The first cable 490A then winds at least partially around one pulley in the fourth set of pulleys 425A, 427A. The first cable 490A then winds at least partially around one pulley in the third set of pulleys 420A, 420B. As discussed in previous embodiments, the first cable 490A can couple to a bead (e.g., immovably coupled to a bead, like bead 315A in FIG. 3A) that is retained within one pulley in the third set of pulleys 420A, 420B. The first cable 490A then winds at least partially around one pulley in the fifth set of pulleys 425B, 427B, after which the first cable 490A winds at least partially around one pulley in the second set of pulleys 440B, 450B. The first cable 490A then extends toward the proximal end of the tool 400 and through the tool shaft. In some embodiments, the first cable 490A winds at least partially around pulleys 450A, 427A, 420A, 425B and 440B, as shown in FIG. 13A.

In the illustrated embodiment, the pulleys 440A, 440B, 425A, 425B are considered outer pulleys and the pulleys 450A, 450B, 427A, 427B are considered inner pulleys. In some embodiments, the first cable 490A winds around two outer pulleys (e.g., pulleys 440B, 425B) and two inner pulleys (e.g., pulleys 450A, 427A). The first cable 490A is shown in FIG. 13A slightly displaced from the pulleys to more clearly illustrate the routing of the first cable 490A.

Figure 13B:
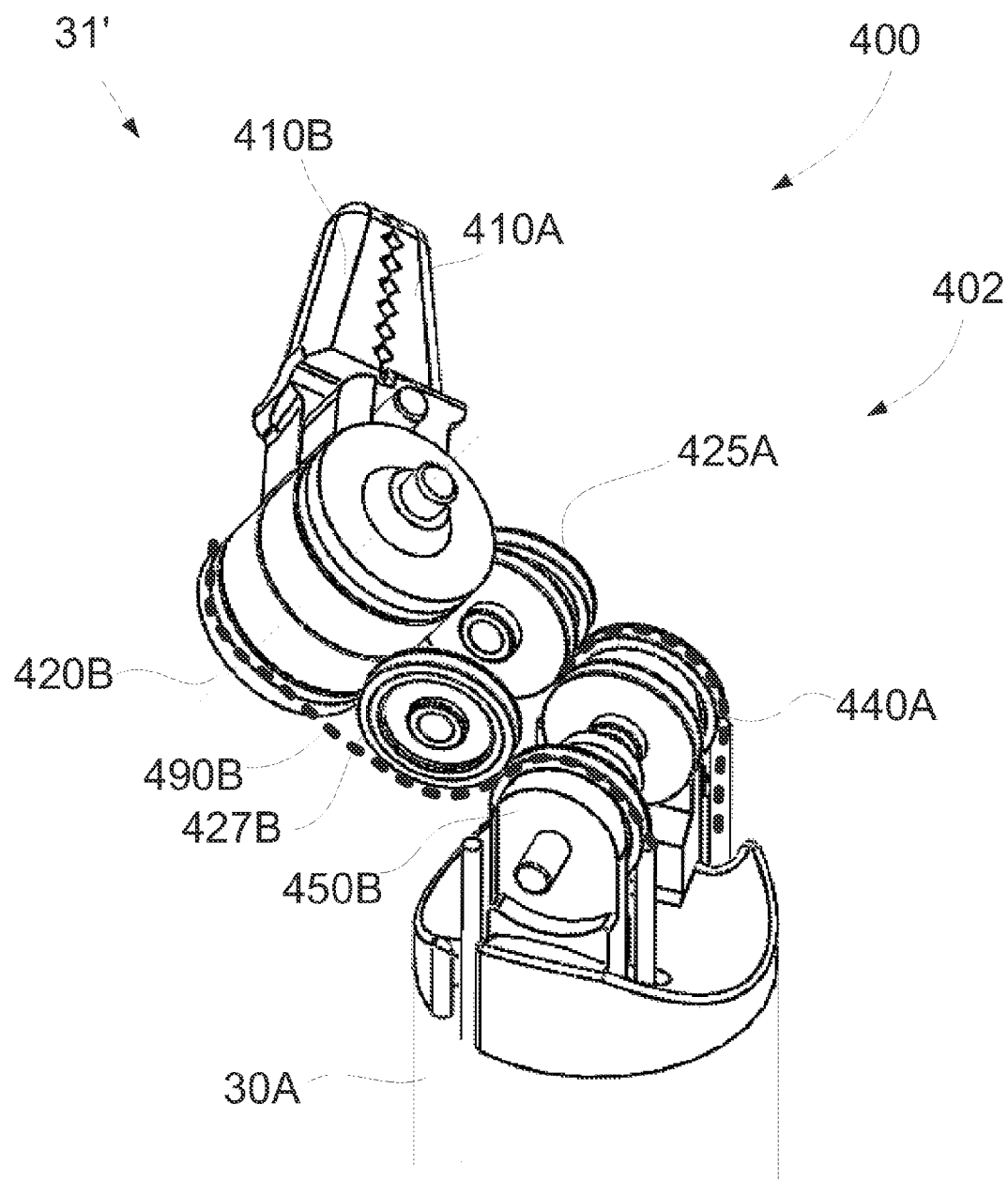
FIG. 13B illustrates the routing of a second cable of the tool of FIG. 12A.

FIG. 13B shows the routing of a second cable 490B in the wrist 402 of the tool 400. The second cable 490B winds at least partially around one pulley in the first set of pulleys 440A, 450A. The second cable 490B then winds at least partially around one pulley in the fourth set of pulleys 425A, 427A. The second cable 490B then winds at least partially around one pulley in the third set of pulleys 420A, 420B. The second cable 490B can couple to a bead (e.g., immovably coupled to a bead, like bead 315A) that is retained within one pulley in the third set of pulleys 420A, 420B, as described in previous embodiments. The second cable 490B then winds at least partially around one pulley in the fifth set of pulleys 425B, 427B, after which the second cable 490B winds at least partially around one pulley in the second set of pulleys 440B, 450B. The second cable 490B then extends toward the proximal end of the tool 400 and through the tool shaft 30A. In some embodiments, the second cable 490B winds at least partially around pulleys 450B, 427B, 420B, 425A and 440A, as shown in FIG. 13B.

In some embodiments, the second cable 490B winds at least partially around two outer pulleys (e.g., pulleys 440A, 425A) and two inner pulleys (e.g., pulleys 450B, 427B). The second cable 490B is shown in FIG. 13B slightly displaced from the pulleys to more clearly illustrate the routing of the second cable 490B.

Figure 14A:
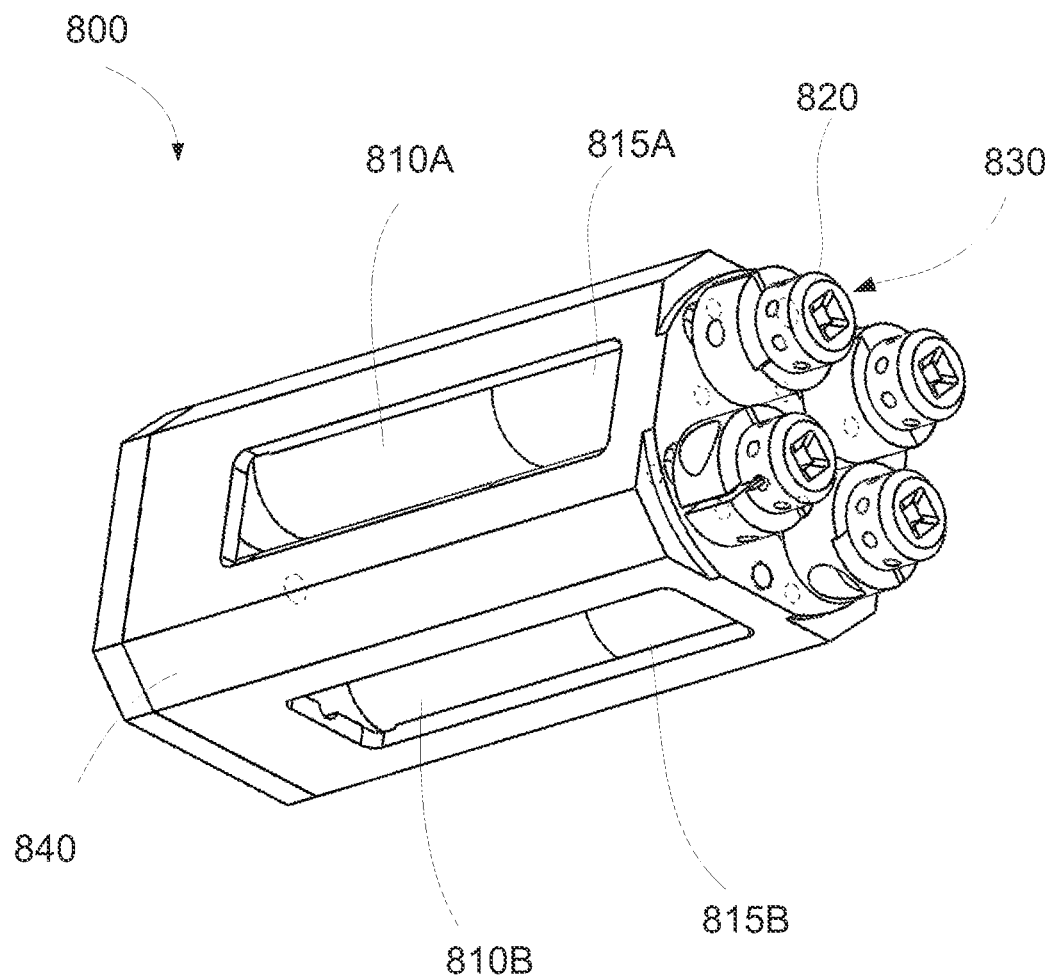
FIG. 14A illustrates an embodiment of the proximal end of a tool.
Figure 14:
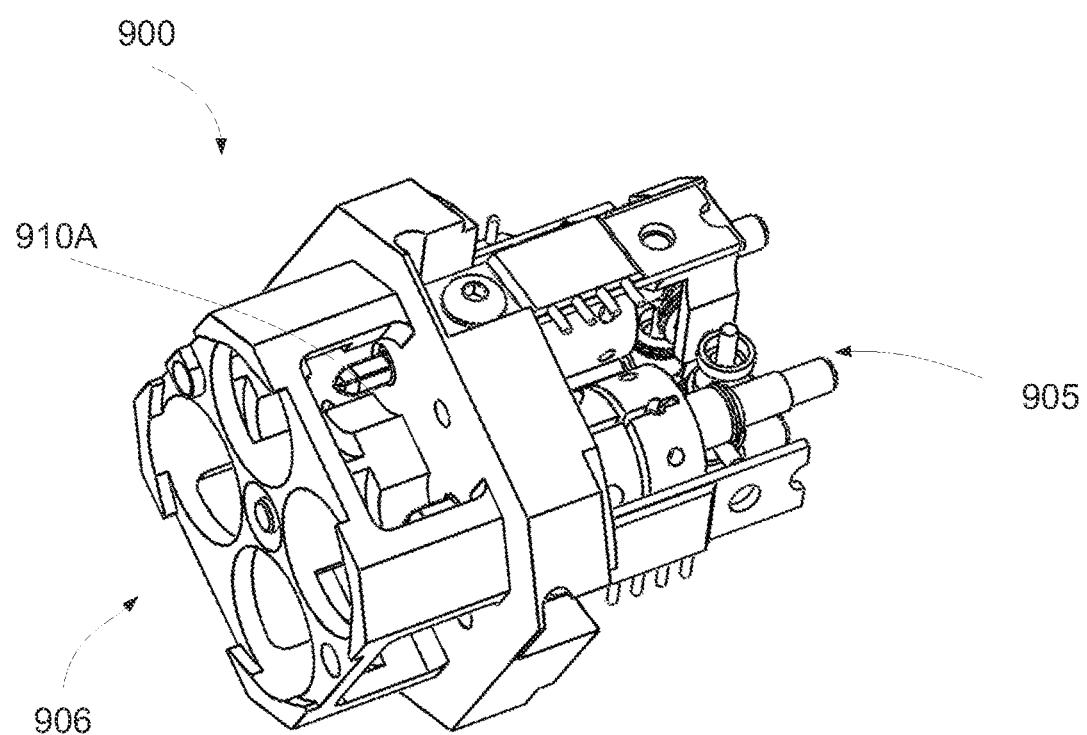
FIG. 14B illustrates a coupling unit that couples to the proximal end of FIG. 14A.
FIG. 14C illustrates the distal end of the coupling unit of FIG. 14B.
FIG. 14D illustrates the coupling unit of FIG. 14B.
FIG. 14E illustrates a partial view of the coupling unit of FIG. 14B.

FIG. 14A shows an embodiment of the proximal end of a tool that can be incorporated into tools described herein. The proximal end includes a motor pack 800. In the illustrated embodiment, the motor pack 800 includes four motors (e.g., electric motors) which drive four independent cables, as previously discussed above.

In some embodiments, each of the four cables is controlled independently by a motor of the motor pack 800. Advantageously, a tool with the motor pack 800, where each of four cables is controlled by a motor of the pack 800 does not require pre-tensioning because the motors can take out any slack in the cable. Pre-tensioning is required due to the elastic properties of the cables which may cause slippage as the cables interact with pulleys in a cable-pulley system. Pre-tensioning is therefore compensated for by the design or by other methodologies in on-market tools. While the method of driving cables described in FIGS. 5A-6D requires only three motors to drive the cables, the systems utilize cable loops that may require pre-tensioning.

With continued reference to FIG. 14A, the motor pack 800 can include a motor housing 840. The motor pack 800 can include four motors retained within the motor housing 840, only two of the motors 810A, 810B visible in FIG. 14A. The four motors 810A, 810B, 810C (not shown), 810D (not shown) can be associated with gearboxes 815A, 815B, 815C (not shown), 815D (not shown), respectively. Each motor 810A, 810B, 810C, 810D can be associated with a spindle, such as spindle 820, and each spindle 820 can have a mating interface 830 (e.g., a square aperture, hexagonal aperture, a slot). The motors 810A, 810B, 810C, 810D are driven under software control by drive units (not shown). The motor pack 840 can be attached to a proximal end of a tool, such as the proximal end 32 of the tool 30 shown in FIG. 11, or any other tool described herein.

Figure 14C:
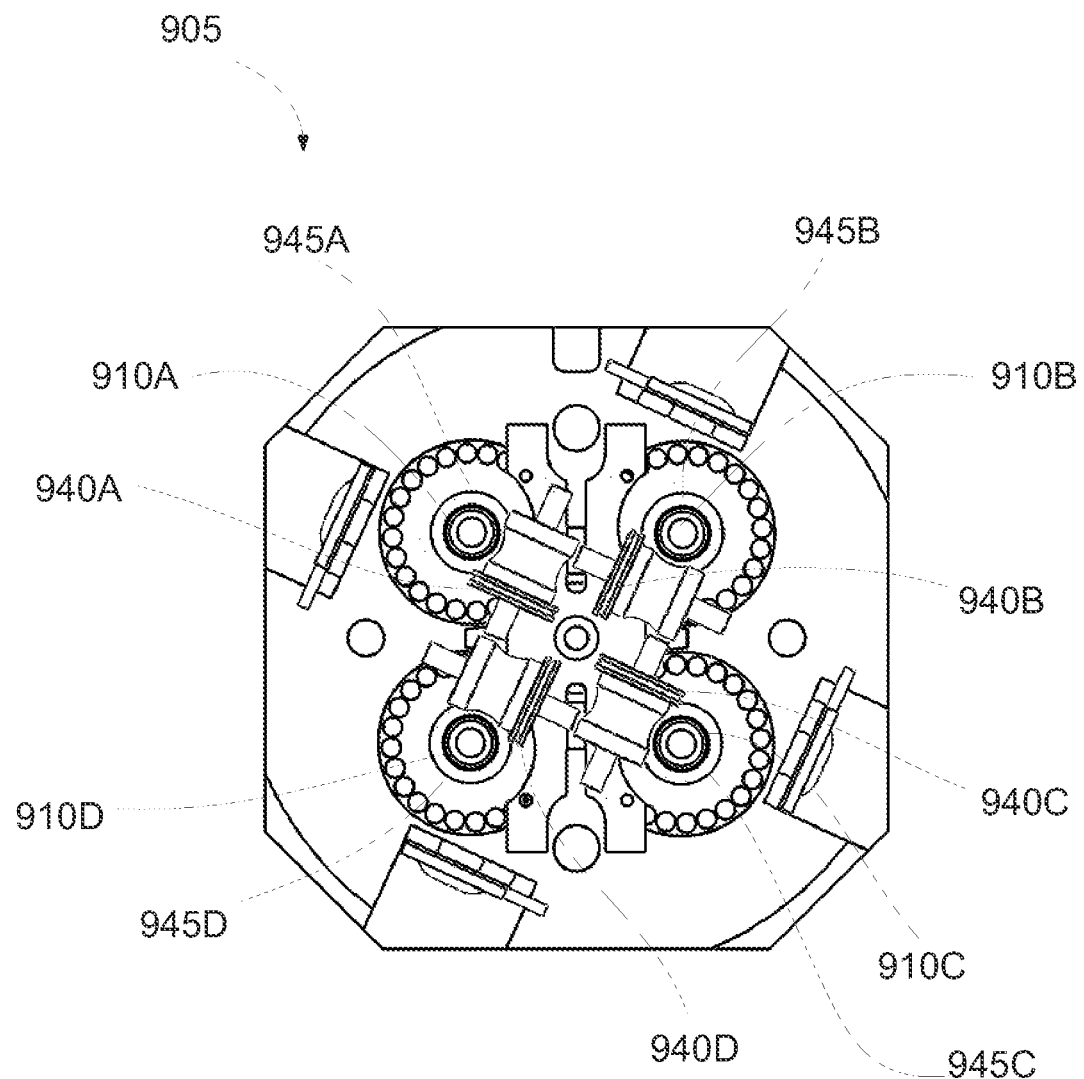

FIG. 14B shows one embodiment of a coupling unit 900 that can removably couple to the motor pack 800. The coupling unit 900 can include a proximal end 906 and a distal end 905. The mating interface 830 of each spindle 820 of the motor pack 800 shown in FIG. 14A can couple and/or mate with corresponding spindles in the coupling unit 900, such as spindle 910A. In FIG. 14B, though only one spindle 910A is visible, the coupling unit 900 can have a corresponding spindle for each of the mating interfaces 830 of the motor pack 800 (e.g., four spindles 910A, 910B, 910C, 910D, as shown in FIG. 14C) In one embodiment, the coupling unit 900 can be disposable. In another embodiment, any component distal to the motor pack 800, including coupling unit 900, tool shaft, wrist and end effector, can be disposable. Therefore, the motor pack 800, which is typically the more expensive part of a tool, can be reusable since the coupling unit 900, which can be incorporated into the proximal portion of the tool, can be easily detached and replaced with a new coupling unit 900 and associated tool shaft, wrist and end effector. This design advantageously provides for a sterile barrier. In other words, everything distal to the motor housing 840 including the coupling unit 900 may be sterile, and the coupling unit 900 can at least partially provide a sterile barrier. The motor housing 840, the motors 810A, 810B, 810C, 810D and/or any component located within the motor pack 800 can be non-sterile.

Figure 14D:
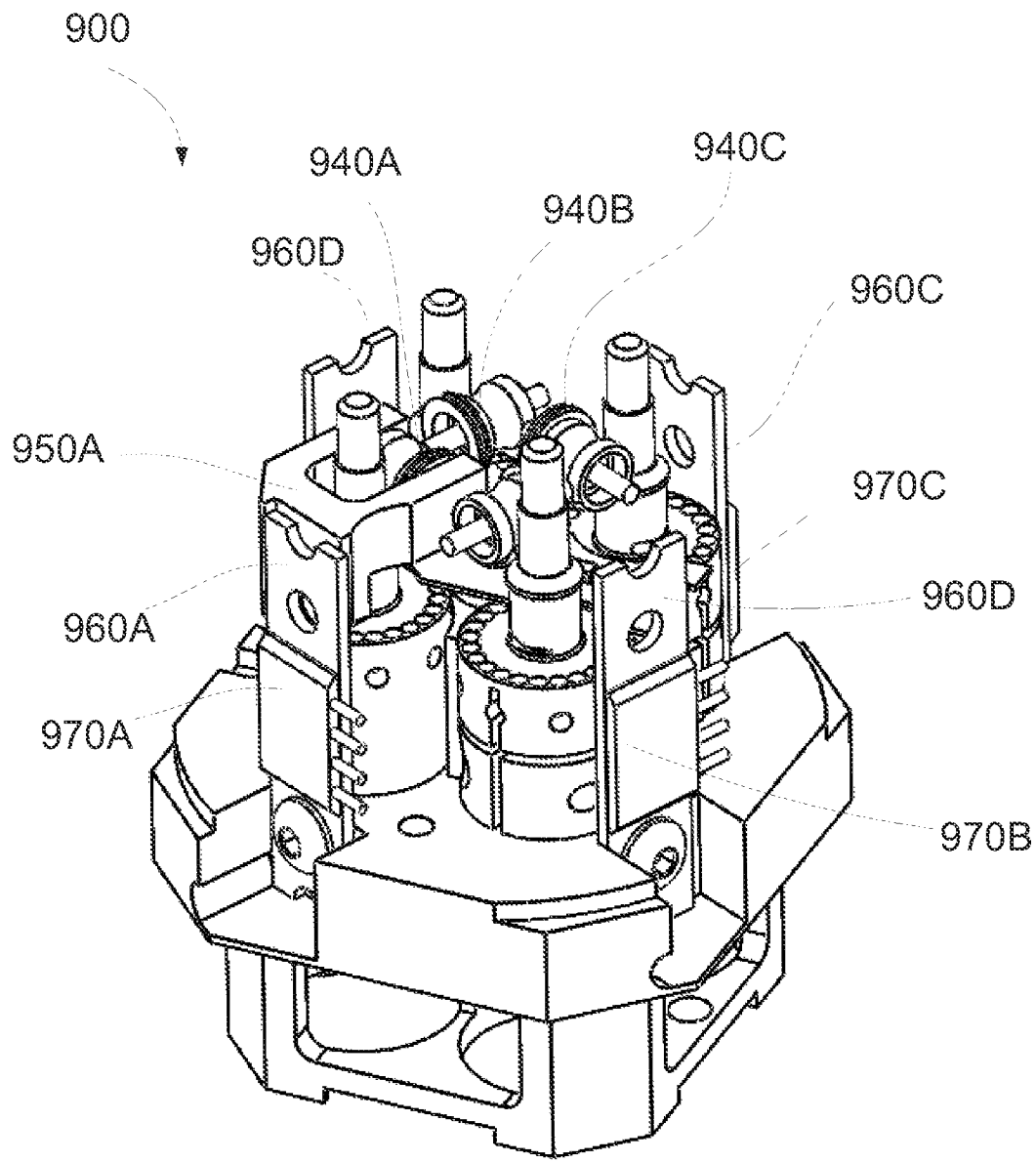

FIGS. 14B-14D further illustrate the coupling unit 900. In one embodiment, the spindles 910A, 910B, 910C, 910D extend through the coupling unit 900 from the proximal end 906 to the distal end 905. The coupling unit 900 can include four pulleys 940A, 940B, 940C, 940D. The coupling unit 900 can include four spools 945A, 945B, 945C, 945D mounted on the spindles 910A, 910B, 910C, 910D, as shown in FIG. 14C. The pulleys 940A, 940B, 940C, 940D can feed cable to the spools 945A, 945B, 945C, 945D. The spools 945A, 945B, 945C, 945D can feed the cables to other components that drive the wrist and/or jaws of the tool, such as the wrist 402 and jaws 410A, 410B in FIG. 12A. The spools 945A, 945B, 945C, 945D can also take up the slack in the cables. The pulleys 940A, 940B, 940C, 940D can be mounted to yokes 950A, 950B (not shown), 950C (not shown), 950D (not shown), as best shown in FIG. 14D.

Referring now to FIG. 14D, only yoke 950A is shown, though as discussed above each of the pulleys 940A, 940B, 940C, 940D can be mounted to a yoke that is similar to the yoke 950A. The yoke 950A can couple to the pulley 940A. The yokes 950B, 950C and 950D can couple to the pulleys 940B, 940C and 940D. The yokes 940A, 940B, 940C, 940D can be coupled to load cells 960A, 960B, 960C, 960D, and the load cells 960A, 960B, 960C, 960D can be coupled to the coupling unit 900.

Figure 14E:
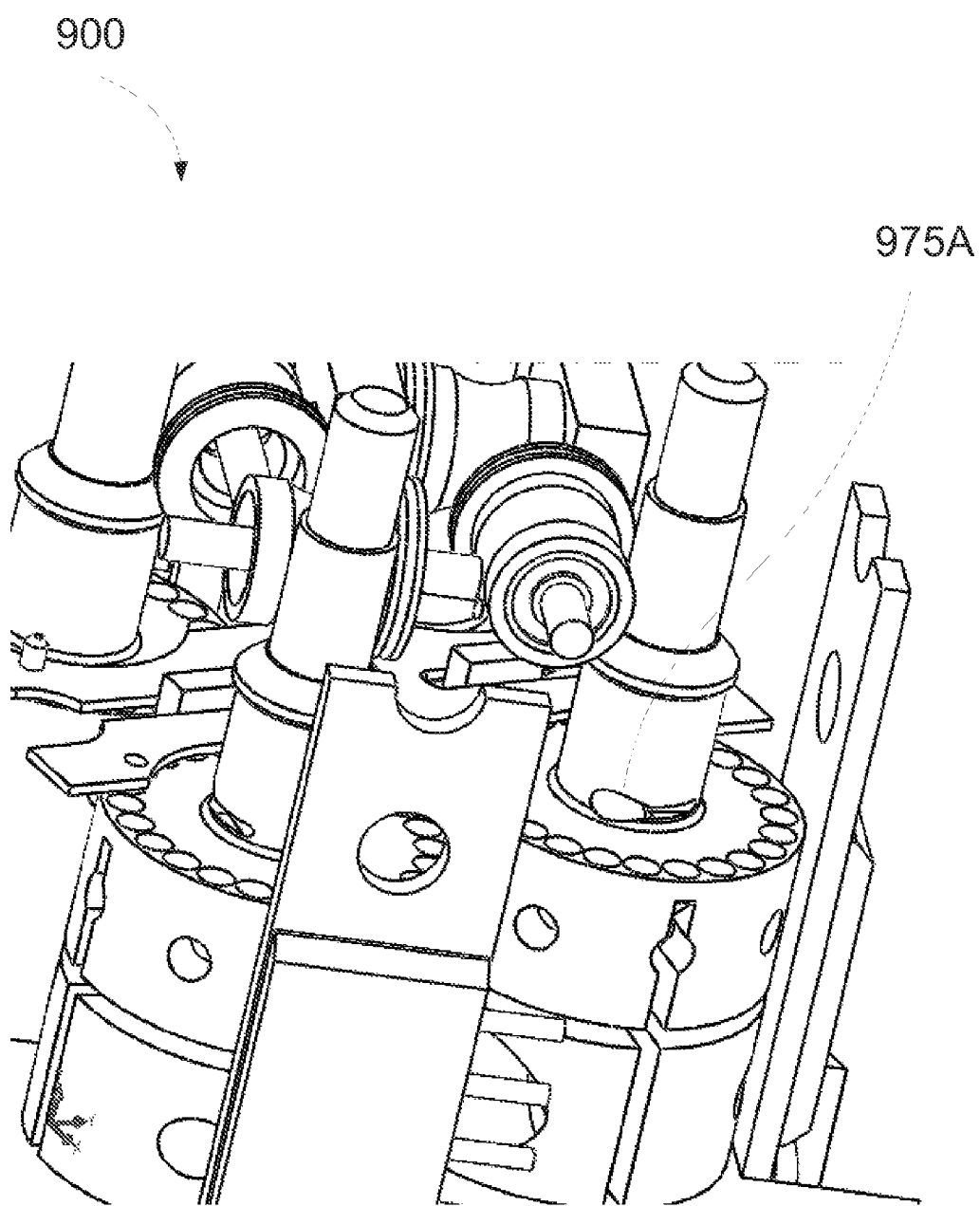

Each cable end is routed around one of the pulleys 940A, 940B, 940C, 940D and wound at least partially around a spool 945A, 945B, 945C, 945D. After winding around the spool 945A, 945B, 945C, 945D, the cable ends are secured to the spool 945A, 945B, 945C, 945D. In one embodiment, the spools 945A, 945B, 945C, 945D can each include a termination feature (e.g., a notch), such as the termination feature 975A best shown in FIG. 14E. Though only one termination feature 975A is shown in FIG. 14E, each of the spools 945A, 945B, 945C, 945D can have a termination feature (e.g., spools 945B, 945C, 945D can have termination features 975B, 975C, 975D, not shown, similar to termination feature 975A). Each cable end may be retained within the termination feature 975A, 975B, 975C, 975D to prevent the cable end from disengaging the corresponding spool 945A, 945B, 945C, 945D. In one embodiment, the cable end can have a shape corresponding to a shape of the termination feature.

With reference to FIG. 14D, the load cells 960A, 960B, 960C, 960D can include one or more sensors. For example, in one embodiment each load cell 960A, 960B, 960C, 960D can include a force sensor 970A, 970B, 970C, 970D. The force sensors 970A, 970B, 970C, 970D can measure the tension of the cable. When the cables are tensioned, the pulleys 940A, 940B, 940C and 940D transfer a force to the load cells 960A, 960B, 960C, 960D. This force can bend the load cells 960A, 960B, 960C, 960D, and said bending can be measured and converted to a measurement of tension. The measurements output by the force sensors 970A, 970B, 970C, 970D can provide haptic feedback to the operator of the tool. For example, the measurements output by the force sensors can be converted to haptic feedback for a surgeon giving him or her sense of the gripping force of the jaws of the tool (e.g., jaws 410A, 410B of tool 400).

Figure 15:
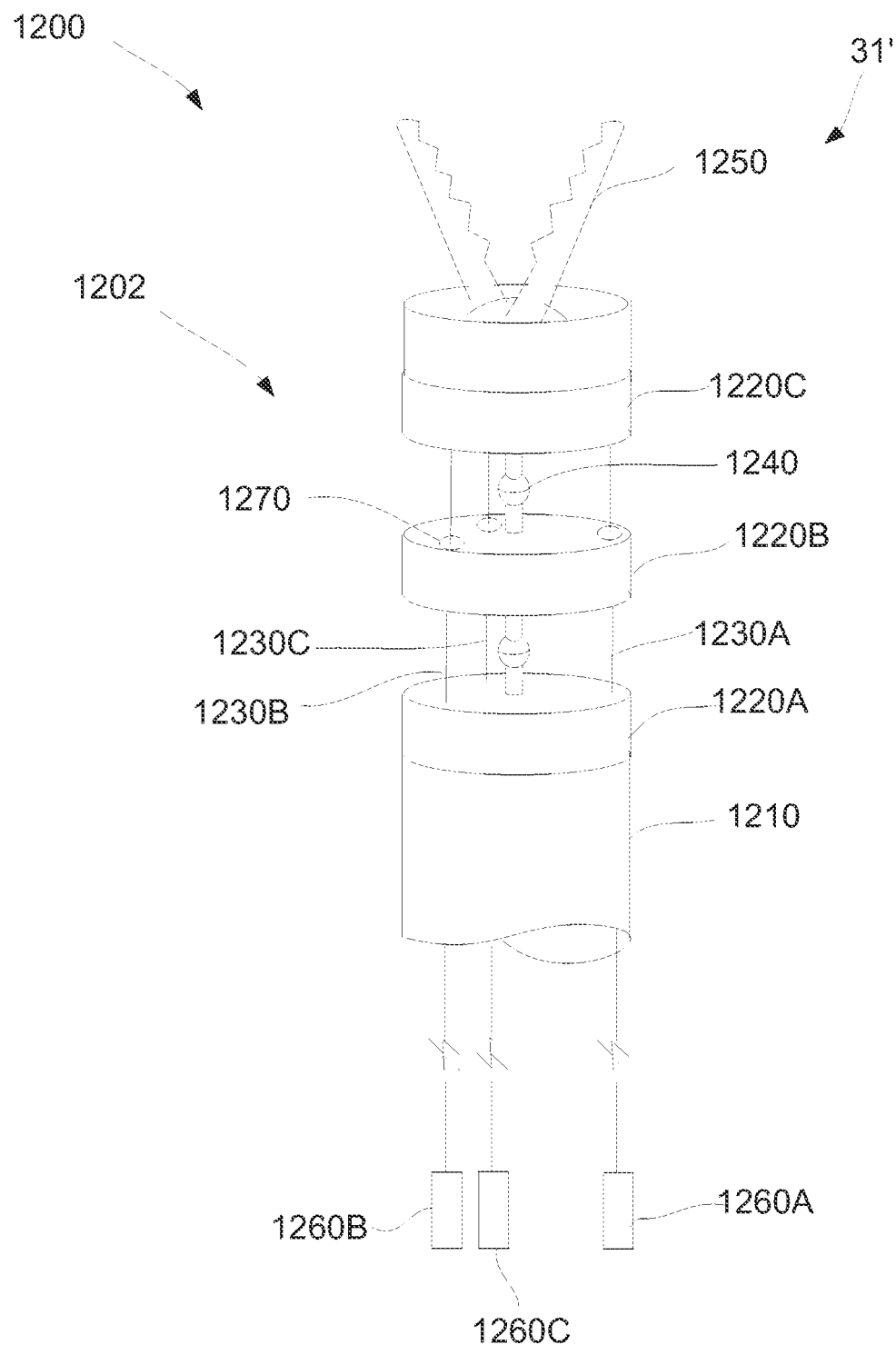
FIG. 15 schematically illustrates an embodiment of a tool including a wrist and an end effector.

FIG. 15 shows another embodiment of a tool. The tool 1200 can include a wrist 1202 that utilizes vertebrae instead of pulleys. On-market tools that utilize vertebrae utilize cable loops to control the bend of the wrist of the tool. In contrast, the tool 1200 can utilize independent cables instead of cable loops to control the position of the wrist 1202. The advantages of this arrangement of the tool 1200 include that pre-tensioning and exact control of the length of the cable is not necessary.

The wrist 1202 of the tool 1200 can include one or more vertebra 1220A, 1220B, 1220C. Although three vertebrae 1220A, 1220B, 1220C are shown, the tool 1200 can have more or fewer vertebrae (e.g., one, two, three, four, five, six vertebrae etc.). The vertebra 1220A can be coupled to the tool shaft 1210. The vertebrae 1220A, 1220B, 1220C can be coupled to other vertebrae and/or components of the tool 1200 via one or more joints 1240 (e.g., ball and socket joint). In the illustrated embodiment, the vertebrae 1220A, 1220B, 1220C can be coupled to the distal end of the tool 1200, as shown in FIG. 15. However, in other embodiments, one or more vertebra 1220A, 1220B, 1220C can be located at any position along the longitudinal length of the tool 1200.

With continued reference to FIG. 15, the tool 1200 can include one or more independent cables 1230A, 1230B, 1230C, which can extend through the tool shaft 1210. Although three cables 1230A, 1230B, 1230C are shown, the tool 1200 can have more or fewer cables (e.g., one, two, three, four, five, six cables etc.). In one embodiment, additional cables can be used to drive the end effector 1250. Each cable 1230A, 1230B, 1230C is independently driven by a motor 1260A, 1260B, 1260C. Since cable loops are not utilized in the tool 1200, this design has the benefits described previously (e.g., no need for pre-tensioning of the cables).

The cables 1230A, 1230B, 1230C can extend through the one or more vertebra 1220A, 1220B, 1220C. In the illustrated embodiment, the cables 1230A, 1230B, 1230C can couple to the vertebra 1220A, 1220B, 1220C via one or more engagement mechanism 1270 (e.g. a bead, similar to bead 315A in FIG. 3A, that is crimped onto the cable and positioned inside a pocket in the vertebra). When a cable 1230A, 1230B, 1230C is tensioned, the tension is transferred to the vertebra 1220A, 1220B, 1220C) via the engagement mechanism 1270. The components of the tools (e.g., vertebra 1220A, 1220B, 1220C can be covered by a sheath (not shown)). Various other vertebrae and cable designs are possible. With the independent control of each cable end, it is possible to manipulate the end effector 1250 in any combination of pitch and yaw.

Figure 16:
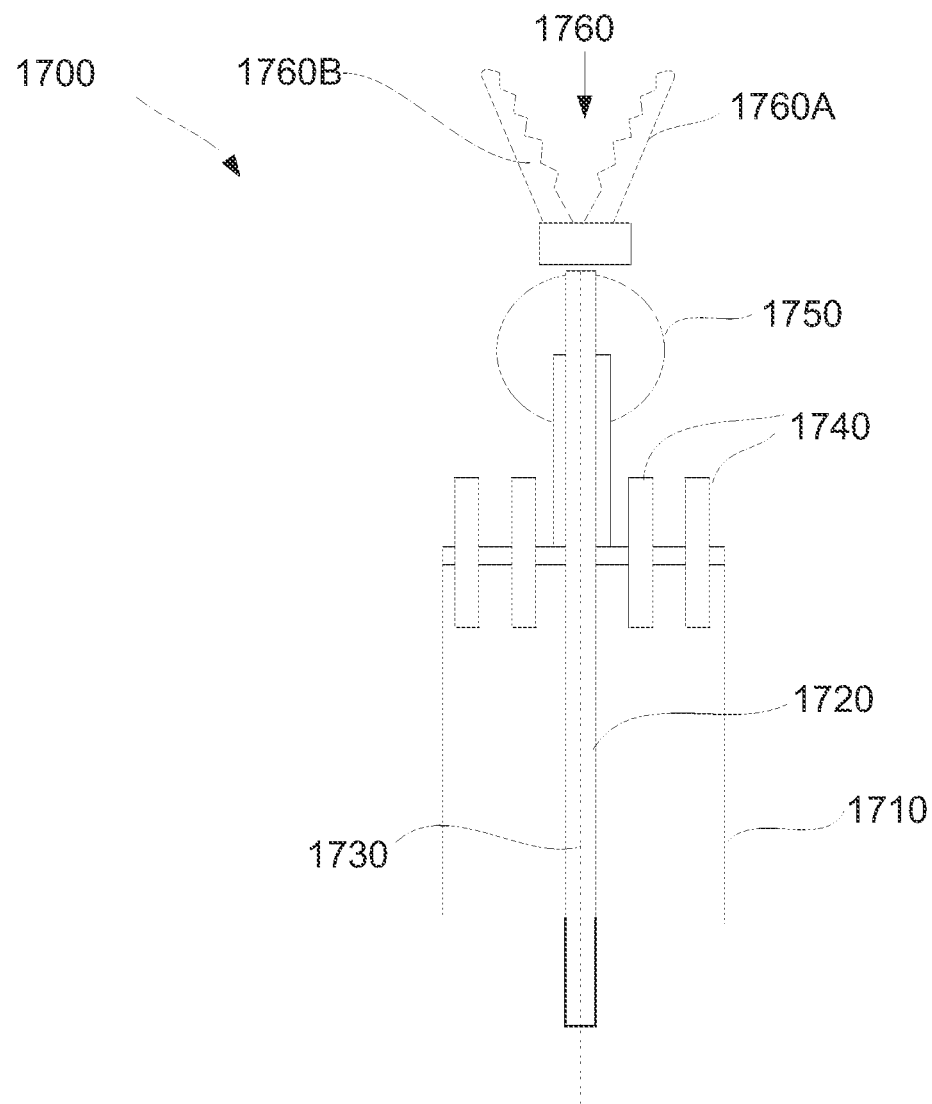
FIG. 16 schematically illustrates an embodiment of a tool including a wrist and an end effector.

FIG. 16 shows another embodiment of a tool. The tool 1700 is similar to the tool shown 30 in FIGS. 1A-3B. In some embodiments, it may be advantageous to uncouple the actuation of the jaws from the wrist of the tool. For example, decoupling the actuation of an end effector from the actuation of a wrist of a tool can inhibit transfer of loads from the end effector to the wrist (e.g., from the jaws of a grasper to pulleys of a wrist of a tool). Such loading of the wrist by the end effector may cause control of the wrist to become much more difficult and/or result in unpredictable movements of the wrist.

The tool 1700 can have a wrist 1702 and include one or more pulleys 1740 and one or more pulleys 1750. The pulleys 1740 can be substantially similar to pulleys 340A, 340B, 350A, 350B shown in FIG. 3A. The pulleys 1750 can be substantially similar to pulleys 320A, 320B shown in FIG. 3A. For clarity, the cable routing for the pulleys 1740, 1750 is not shown.

In addition to the cables (not shown) that wind at least partially around the pulleys 1740, 1750, the tool 1700 can include one or more additional cables 1730 for controlling the jaws 1760A, 1760B of an end effector 1760, (e.g., grasper). Although one cable 1730 is shown, the tool 1700 can include any number of cables (e.g., one two, three, four, five, six cables, etc.). The cable 1730 can be retained within a sheath 1720, which in one embodiment can be a flexible sheath. In the illustrated embodiment, the end effector 1760 (e.g., the jaws, the grasper) is coupled to the pulley 1750. The cable 1730 can at least partially wind around the pulley 1750 and can control the end effector 1760 via the motion of the pulley 1750. The cable 1730 can be coupled to an actuation mechanism for controlling the end effector 1760 via the pulley 1750. The actuation mechanism that actuates the cable 1730 may be one or more pulleys (e.g., pulleys located near the base of the end effector 1760). In the illustrated embodiment, the end effector 1760, including the jaws 1760A, 1760B, is decoupled from the pulleys 1740, and therefore the end effector 1760 advantageously does not transfer a load to the pulleys 1740. That is, the motion of the end effector 1760 is independent of the motion imparted on the pulleys 1740 by cables that wind about the pulleys 1740.

As described in embodiments herein, the tool may have an elbow or bend. In order to maintain control of the tool, it may be important for the user (e.g., an operator, a surgeon) to know the shape of the tool. The flexible section of the tools described herein (e.g., flexible section 1305) can be coupled to one or more sensors (e.g., a plurality of sensors), where the sensors can transmit data based on the shape of the tool. In one embodiment, the data may be in real time. The data may be transmitted through a wired or wireless connection.

The one or more sensors can include various types of sensors (e.g., strain sensors, position sensors). The one or more sensors can be placed at any location on or within the tool and/or flexible section (e.g. coupled along the length of the tool, coupled to the flexible core, coupled to the vertebra). The sensors may be coupled to the tool using various techniques (e.g. biocompatible glue or adhesive).

In some embodiments, indirect ways of calculating the shape of the flexible section may be utilized. For example, the tension of the cables causing the bend may be monitored. If the relative tension of each of the cables responsible for causing the bend is known, then the bend may be estimated. Where no external forces pushing against the flexible section are present while the flexible section is bent, such monitoring of the tension on the cables causing the bend can provide an estimate of the shape of the bend. The estimate may be combined with data from the sensors to improve the estimation of the shape of the tool (e.g., the bend).

In some embodiments, a camera may monitor the shape of the tool. The camera may be a camera inserted into the body cavity of a patient. The camera may be positioned at any location to aid the user. The camera can send data related to the tool (e.g., images) to a processing unit (e.g., a processing unit of the hyperdexterous surgical system 5). The processing unit may further process the images and use pattern recognition techniques to recognize the flexible section of the tool. Once the flexible section is recognized, the parameters of the bend may be calculated based on the image. These parameters may be transmitted to a main processing unit responsible for maintaining control of the tool.

Figure 17A:
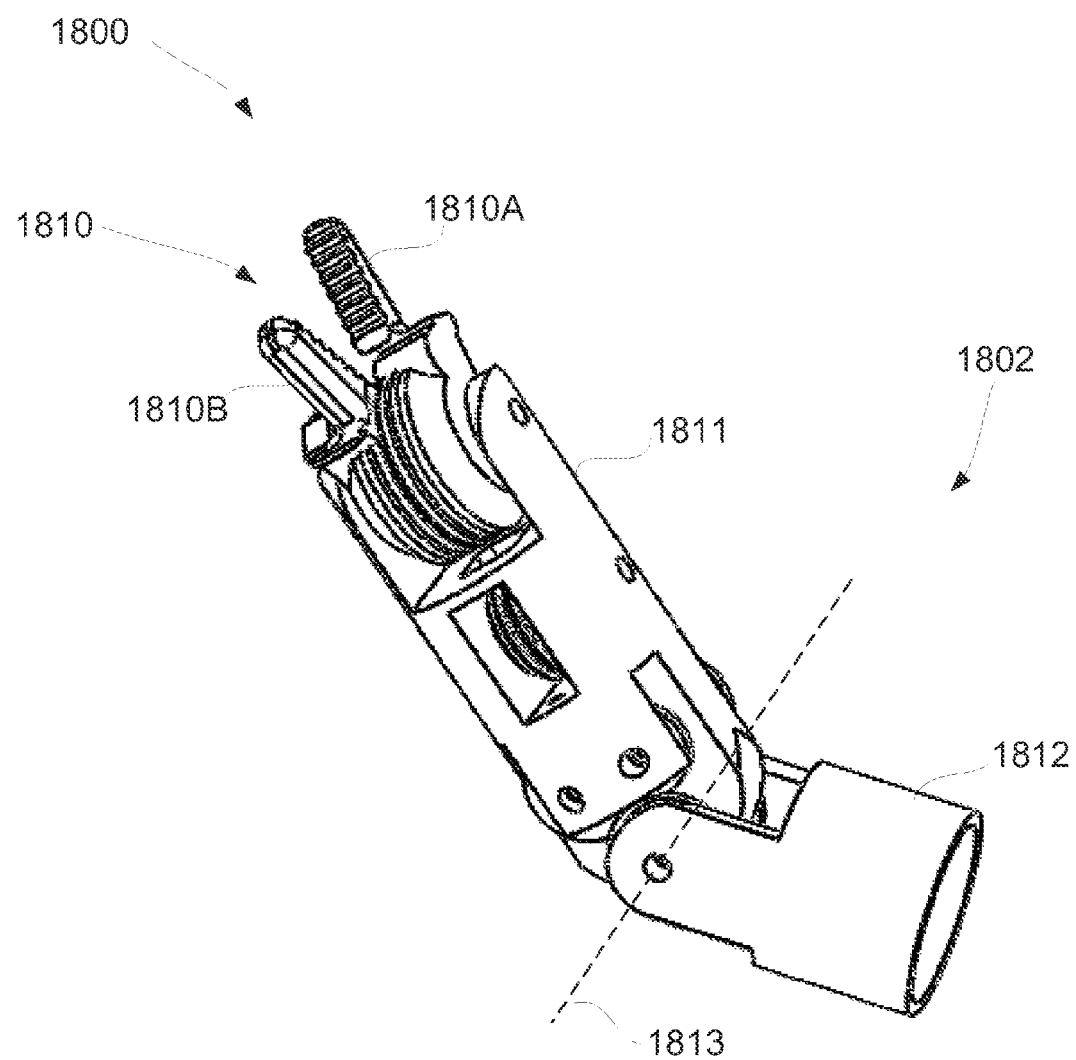
FIG. 17A illustrates a distal portion of an embodiment of a tool including a wrist and an end effector.
Figure 17B:
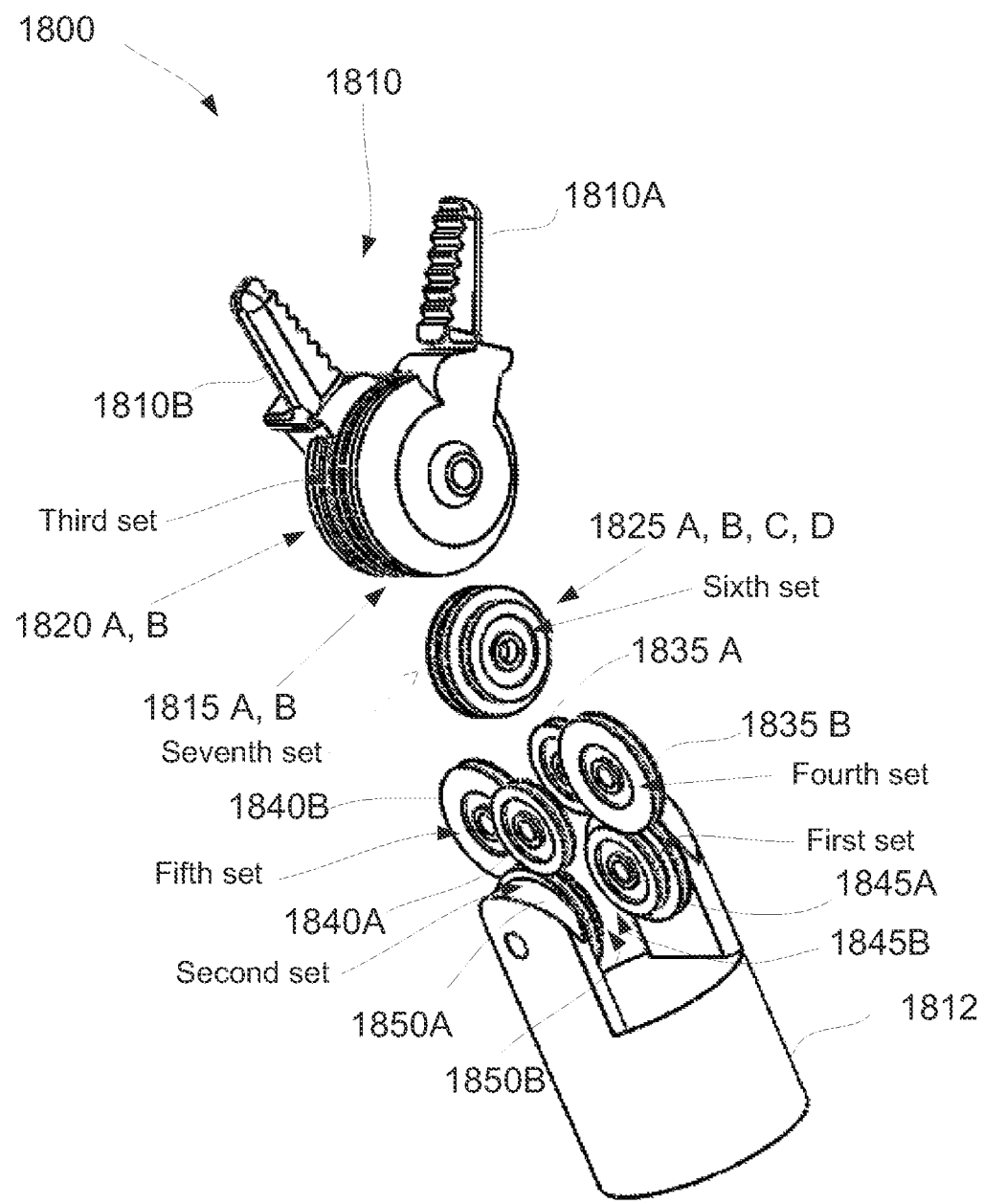
FIG. 17B illustrates the tool of FIG. 17A.
Figure 17C:
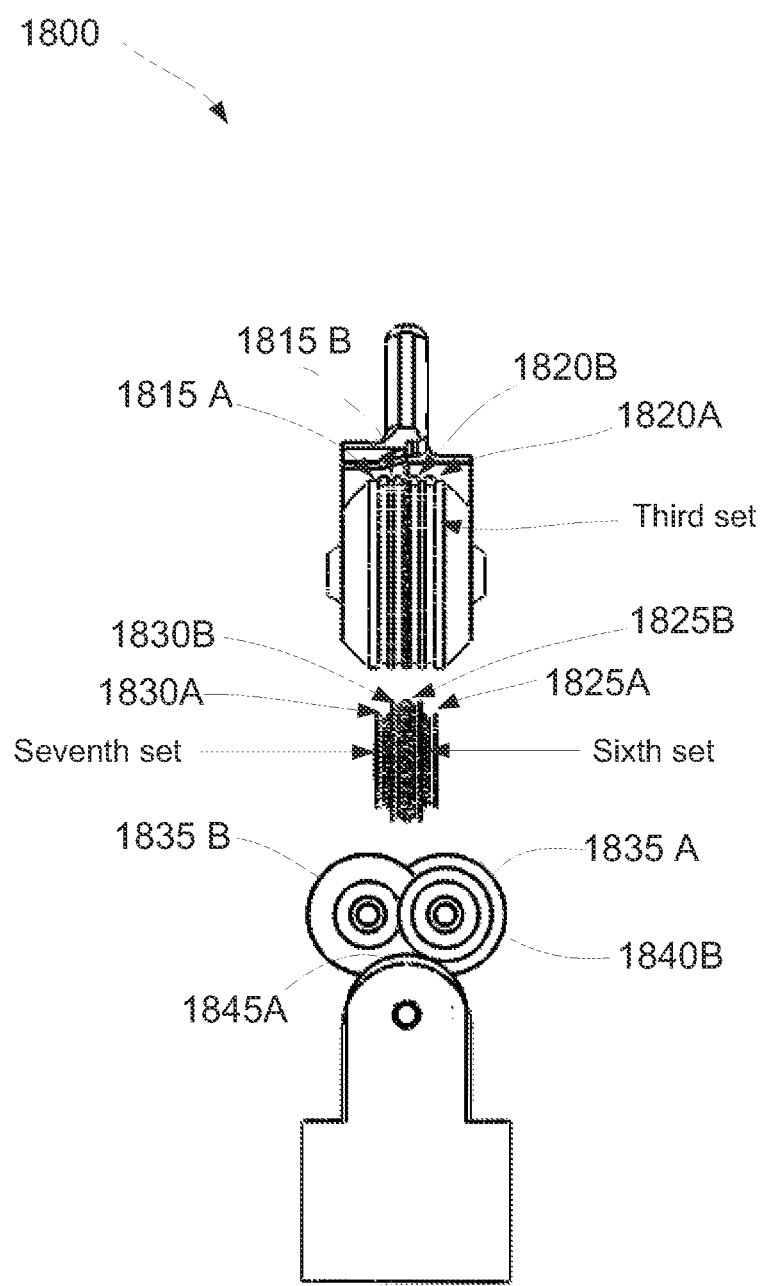
FIG. 17C illustrates the tool of FIG. 17A.

FIG. 17A shows another embodiment of a tool. The tool 1800 can have a wrist 1802 and can include a housing 1811. FIGS. 17B-17C shows the tool 1800 with the housing 1811 removed. The tool 1800 can include an end effector 1810 with a pair of jaws 1810A, 1810B. Other embodiments of end effectors can be utilized. The tool 1800 can include various pulleys, as shown in FIG. 17B.

The pulleys 1845A, 1845B are arranged as a first set of pulleys. The pulleys 1850A, 1850B are arranged as a second set of pulleys. The first set of pulleys 1845A, 1845B and the second set of pulleys 1850A, 1850B can be coupled to a yoke 1812, which can couple to a tool shaft (not shown). The tool can also include pulleys 1820A, 1820B, 1815A, 1815B arranged as a third set of pulleys. The jaws 1810A, 1810B can be coupled to the third set of pulleys 1815A, 1815B, 1820A, 1820B. In the illustrated embodiment, the jaw 1810A is coupled to the pulleys 1815A, 1815B and the jaw 1810B is coupled to the pulleys 1820A, 1820B.

The tool 1800 can also include pulleys 1835A, 1835B arranged as a fourth set of pulleys. The center of rotation of pulley 1835A can be offset from the center of rotation of pulley 1835B. In one embodiment, the pulley 1835A can have a smaller diameter than the pulley 1835B. The tool 1800 can also include pulleys 1840A, 1840B arranged as a fifth set of pulleys. The center of rotation of pulley 1840A can be offset from the center of rotation of pulley 1840B. The pulley 1840A can have a smaller diameter than the pulley 1840B. The pulleys 1835A, 1840B can be located on the same axis of rotation. The pulleys 1835B, 1840A can be located on the same axis of rotation. The center of rotation of the pulleys 1835A, 1840B can be offset from the center of rotation of the first set of pulleys 1845A, 1845B and the second set of pulleys 1850A, 1850B. The center of rotation of the pulleys 1835B, 1840A can be offset from the center of rotation of the first set of pulleys 1845A, 1845B and the second set of pulleys 1850A, 1850B.

With reference to FIG. 17C, the pulleys 1825A, 1825B are arranged as a sixth set of pulleys. The pulleys 1830A, 1830B are arranged as a seventh set of pulleys. In the illustrated embodiment, the pulleys 1825A, 1830A are outer pulleys and the pulleys 1825B, 1830B are inner pulleys. The outer pulleys 1825A, 1830A can be smaller in diameter than the inner pulleys 1825B, 1830B.

The sixth set of pulleys 1825A, 1825B and the seventh set of pulleys 1830A, 1830B can align with the pair of jaws 1810A, 1810B and/or the third set of pulleys 1820A, 1820B, 1815A, 1815B. In some embodiments, the pulleys 1820A, 1820B, 1815B, 1815A aligns with the pulleys 1825A, 1825B, 1830B, 1830A, respectively, to thereby allow cables to extend along a straight path between the pulleys 1820A, 1820B, 1815B, 1815A and the pulleys 1825A, 1825B, 1830B, 1830A, respectively, thus advantageously reducing bends in the cables and friction between the cables and the pulleys. Other advantages of this arrangement are explained below.

The third set of pulleys 1815A, 1815B, 1820A, 1820B can have a large diameter (e.g., relative to the other pulleys in the tool 1800). In one embodiment, the diameter of the third set of pulleys 1815A, 1815B, 1820A, 1820B can have a diameter as large as (e.g., substantially equal to) the diameter of the tool shaft (not shown). The third set of pulleys 1815A, 1815B, 1820A, 1820B can be arranged close to each other and/or closer to the central axis of the tool shaft than the pulleys 320A, 320B of tool 30 shown in FIG. 1A. The placement and the diameter size of the third set of pulleys 1815A, 1815B, 1820A, 1820B can advantageously increase the reliability and usable lifetime (e.g., less wear and tear) of the cables. Since larger pulleys have a larger diameter, cables that traverse larger pulleys bend less thus affecting the reliability in a positive way. The placement of the third set of pulleys 1815A, 1815B, 1820A, 1820B along with the placement of the other sets of pulleys ensures that the one or more cables of the tool 1800 experience fewer and less tight turns, again affecting the reliability and usable lifetime of the cables in a positive way. The placement and the diameter size of the third set of pulleys 1815A, 1815B, 1820A, 1820B is arranged to apply a larger force on jaws than the pulleys 320A, 320B shown in FIG. 1A, since the cables experience fewer bends and less tight turns, thereby being able to apply larger forces on the jaws.

Figures 17D, 17E:
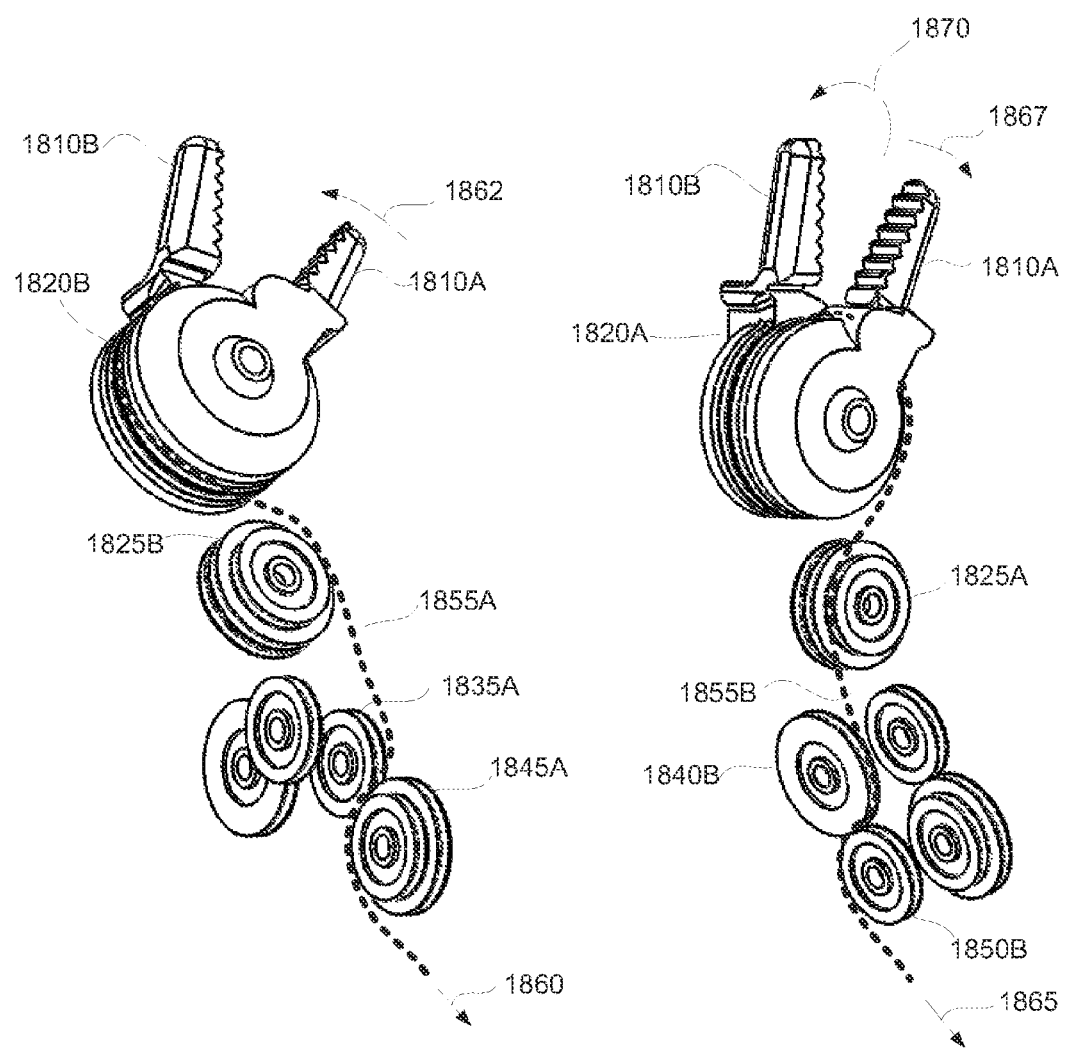
FIG. 17D illustrates the cable routing of a first cable for the tool of FIG. 17A.
FIG. 17E illustrates the cable routing of a second cable for the tool of FIG. 17A.

The tool 1800 can be actuated to move the jaws 1810A, 1810B in a variety of ways such as grasping (e.g., jaws rotating independently via pulleys 1815A, 1815B, 1820A, 1820B), yaw (e.g., jaws rotating together via pulleys 1815A, 1815B, 1820A, 1820B), and pitch (e.g., jaws rotating about axis 1813 through yoke 1812). FIGS. 17D-17E shows the cable routing of a first cable 1855A of the tool 1800. As discussed previously in other embodiments, four cables can be controlled independently to effect motion on the yoke 1812 and/or one or both of the jaws 1810A, 1810B. The independent control of each cable end may provide more accurate movement of the wrist 1802 (see FIG. 17A) and the end effector 1810. The cable routing for FIGS. 17D-17E control jaw 1810A. The tool 1800 utilizes four cables with four cable ends (similar to cables 390A', 390A", 390B', 390B" described herein).

Referring to FIG. 17D, the first cable 1855A originates from the tool shaft (not shown). The first cable 1855A winds at least partially around one pulley in the first set of pulleys 1845A, 1845B. The first cable 1855A then winds at least partially around one pulley in the fourth set of pulleys 1835A, 1835B. The first cable 1855A then winds at least partially around one pulley in the sixth set of pulleys 1825A, 1825B. The first cable 1855A then winds at least partially around one pulley in the third set of pulleys 1815A, 1815B, 1820A, 1820B. In some embodiments, the first cable 1855A winds at least partially around the pulleys 1845A, 1835A, 1825B, 1820B, as shown in FIG. 17D. The cable 1855A can be immovably coupled to the pulley 1820B (e.g., via crimping to a bead retained in a pocket of the pulley, such as the bead 315A in FIG. 3A). In some embodiments, the first cable 1855A winds at least partially around the inner pulleys 1820B, 1825B, and the outer pulley 1835A, 1845A.

Referring to FIG. 17E, a second cable 1855B originates from the tool shaft (not shown). The second cable 1855B winds at least partially around one pulley in the second set of pulleys 1850A, 1850B. The second cable 1855B then winds at least partially around one pulley in the fifth set of pulleys 1840A, 1840B. The second cable 1855B then winds at least partially around one pulley in the sixth set of pulleys 1825A, 1825B. The second cable 1855B then winds at least partially around one pulley in the third set of pulleys 1815A, 1815B, 1820A, 1820B. In some embodiments, the second cable 1855B winds at least partially around the pulleys 1850B, 1840B, 1825A, 1820A, as shown in FIG. 17E. In some embodiments, the second cable 1855B winds at least partially around the outer pulleys 1820A, 1825A and the inner pulleys 1840B, 1850B.

With reference to FIGS. 17D-17E, if only one cable is actuated or tensioned, the jaw will rotate in one direction, and if the other cable is actuated or tensioned, the jaw will rotate in an opposite direction. Additionally, the amount of tension placed on the cables can control the position of the jaws 1810A, 1810B. For example, the cable 1855A shown in FIG. 17D is tensioned in the direction of arrow 1860 and the cable 1855B is relaxed. The jaw 1810A will thus move in the direction of the arrow 1862. If instead the cable 1855B is tensioned in the direction of arrow 1865, the jaw 1810A will move in the direction of the arrow 1867. If both cables are tensioned at the same time, the third set of pulleys 1815A, 1815B, 1820A, 1820B do not rotate. Rather, the third set of pulleys 1815A, 1815B, 1820A, 1820B move in a motion as shown by the arrow 1870, into the plane of the paper (i.e., about axis 1813 of yoke 1812, as shown in FIG. 17A).

Another pair of cables can be coupled to the jaw 1810B in a similar manner as cables 1855A, 1855B are coupled to jaw 1810A. The action of pulling said other set of cables attached to the jaw 1810B is not explained as it is similar to the above explanation for cables 1855A, 1855B. From the above explanation it can be seen how the motion of the jaws 1810A, 1810B can in one embodiment be controlled with four independent cables.

Figure 18A:
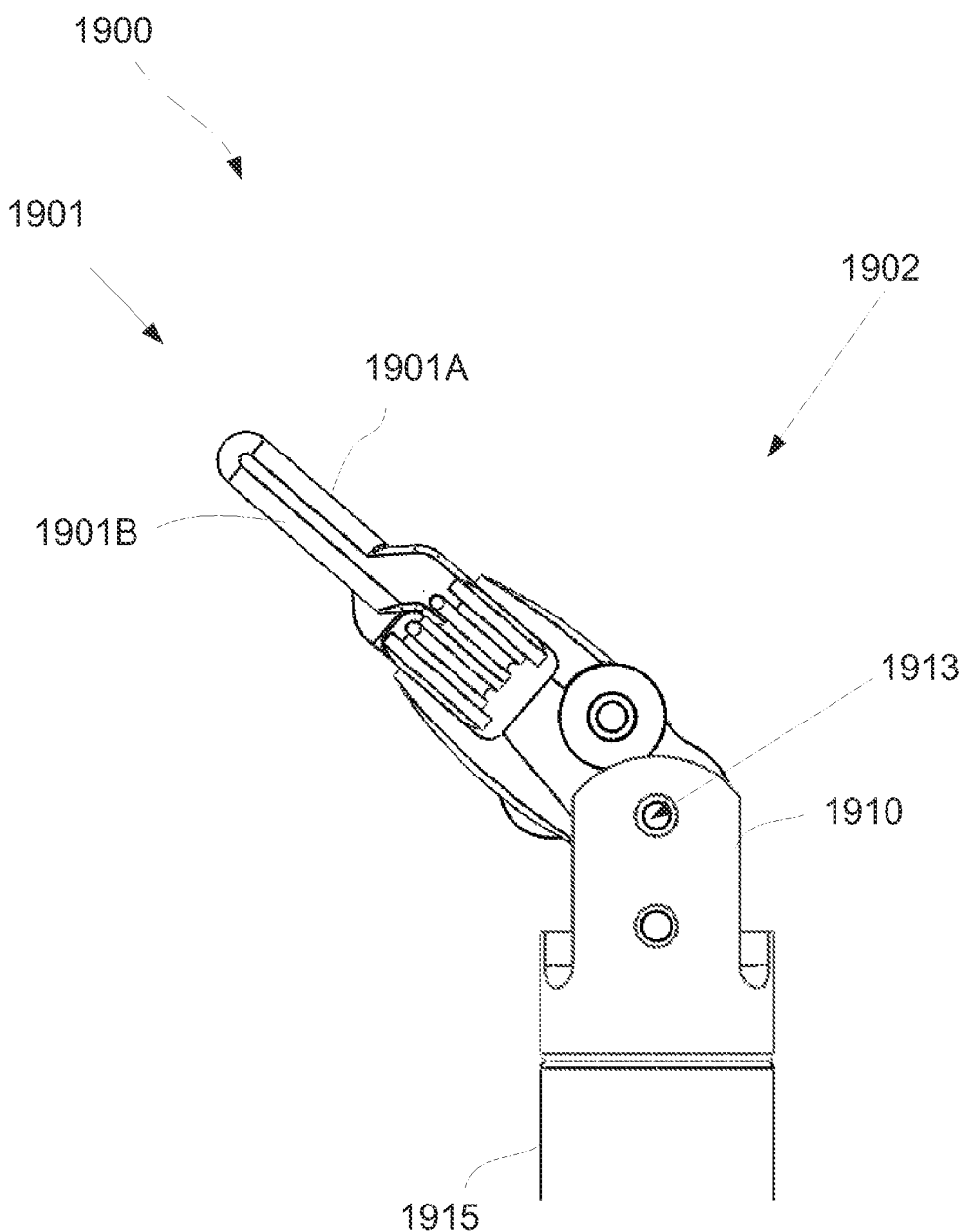
FIG. 18A illustrates a distal end of an embodiment of a tool including a wrist and an end effector.

FIG. 18A shows another embodiment of a tool. The tool 1900 can have a wrist 1902 and end effector 1901 that includes two jaws 1901A, 1901B. The tool 1900 can include a yoke 1910 coupled to a tool shaft 1915. FIG. 18B shows the yoke 1910 removed. The tool 1900 can include a first set of pulleys 1930A, 1930B. The tool 1900 can also include a second set of pulleys 1935A, 1935B. The axis of rotation of the first set of pulleys 1930A, 1930B can be aligned with the axis of rotation of the second set of pulleys 1935A, 1935B. The tool 1900 can include a third set of pulleys 1905A, 1905B. The jaws 1901A, 1901B can be coupled third set of pulleys 1905A, 1905B.

The tool 1900 can include a fourth set of pulleys 1920A, 1920B, and can include a fifth set of pulleys 1925A, 1925B. The fourth set of pulleys 1920A, 1920B can be located on one side of the tool 1900 and fifth set of pulleys 1925A, 1925B can be located on the other side of the tool 1900. The axis of rotation of the fourth set of pulleys 1920A, 1920B can be aligned with the axis of rotation of the fifth set of pulleys 1925A, 1925B.

The tool 1900 can additionally include a sixth set of pulleys 1910A, 1910B and a seventh set of pulleys 1915A, 1915B. The sixth set of pulleys 1910A, 1910B can be located on one side of the tool 1900 and seventh set of pulleys 1915A, 1915B can be located on the other side of the tool 1900. The sixth and seventh sets of pulleys are offset pulleys because the center of rotation of the sixth set of pulleys 1910A, 1910B is offset from the center of rotation of the seventh set of pulleys 1915A, 1915B.

Figures 18D, 18E:
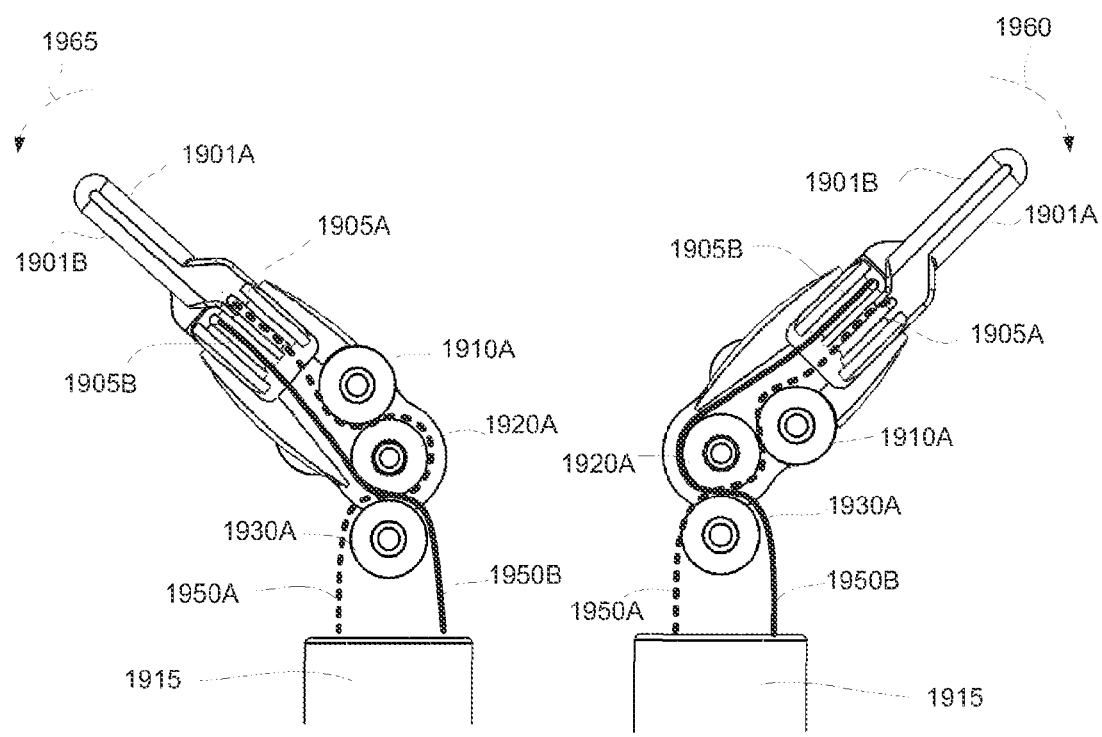
FIG. 18D illustrates the cable routing of a first cable for the tool of FIG. 18A.
FIG. 18E illustrates the cable routing of a second cable for the tool of FIG. 18A.

The tool 1900 can be actuated to move the jaws 1905A, 1905B in a variety of ways such as grasping (e.g., jaws rotating independently via pulleys 1905A, 1905B), yaw (e.g., jaws rotating together via pulleys 1905A, 1905B), and pitch (e.g., jaws rotating about axis 1913 of yoke 1910 shown into plane of paper in FIG. 18A). FIG. 18D shows the routing of a first cable 1950A and a second cable 1950B. For clarity, the first cable 1950A is shown in a dashed line and the second cable 1950B is shown in a solid line. The first cable 1950A originates from the tool shaft 1915. The first cable 1950A winds at least partially around one pulley in the first set of pulleys 1930A, 1930B. The first cable 1950A then winds at least partially around one pulley in the fourth set of pulleys 1920A, 1920B. The first cable 1950A then winds at least partially around one pulley in the sixth set of pulleys 1910A, 1910B. The first cable 1950A then winds at least partially around one pulley in the third set of pulleys 1905A, 1905B. In some embodiments, the first cable 1950A winds at least partially around the pulley 1905A, the outer pulley 1910A, the outer pulley 1920A, and the outer pulley 1930A. The cable 1950A can be immovably coupled to the pulley 1905A (e.g., via crimping to a bead retained in a pocket of the pulley, such as the bead 315A in FIG. 3A).

The second cable 1950B also originates from the tool shaft 1915. The second cable 1950B winds at least partially around one pulley in the first set of pulleys 1930A, 1930B. The second cable 1950B then winds at least partially around one pulley in the fourth set of pulleys 1920A, 1920B. The second cable 1950B then winds at least partially around one pulley in the third set of pulleys 1905A, 1905B. In some embodiments, the second cable 1950B winds at least partially around the pulley 1905B, inner pulley 1920B, and inner pulley 1930B. The second cable 1950B does not wind around one pulley in the sixth set of pulleys 1910A, 1910B. The cable 1950B can be immovably coupled to the pulley 1905B (e.g., via crimping to a bead retained in a pocket of the pulley, such as the bead 315A in FIG. 3A). The cables 1950A, 1950B extend toward the proximal end of the tool 1900.

The jaw 1910A is coupled to pulley 1905A, and the jaw 1901B is coupled to pulley 1905B. The first cable 1905A can couple to the pulley 1905A and control jaw 1901A. The second cable can couple to the pulley 1905B and control the jaw 1901B. Another pair of cables (1905C, 1905D) can extend along the opposite side of the pulleys and can couple to the pulleys 1905A and 1905B, and the cable routing would have the same configuration shown in FIGS. 18D-

18E, except the cables would wind at least partially around pulleys 1915A, 1915B. In some embodiments, the cables 1905A and 1905C are integral and form a single cable. In some embodiments, the cables 1905B and 1905D are integral and form a single cable. The action of pulling said other set of cables (e.g., 1905C, 1905D) is not explained as it is similar to the above explanation for cables 1950A, 1950B.

From the above explanation it can now be seen how the motion of the jaws 1901A, 1901B may be controlled with four independent cables (e.g., four independent cable ends). The cables 1950A, 1950B, 1950C, 1950D, can be coupled to the pulleys 1905A, 1905B with an engagement mechanism (e.g. via crimping to a bead retained in a pocket of the pulley, such as the bead 315A in FIG. 3A).

For example, the cable 1950A is tensioned and the other cables are relaxed. The jaw 1901A will move according to the tension that is experienced by the third set of pulleys 1905A, 1905B. When both sides of the pulley 1905A are tensioned (e.g., if there are two independent cables, when both cables are tensioned at the same time), the wrist moves in the direction of arrow 1960 as shown in FIG. 18E. When both sides of pulley 1905B are tensioned (e.g., if there are two independent cables, when both cables are tensioned at the same time), the wrist moves in the direction of arrow 1965 as shown in FIG. 18D. From the above explanation it can now be seen how the motion of the jaws 1901A, 1901B may be controlled with four cables (e.g., four independent cables having four independent cable ends, or two cables having four independent cable ends).

While certain embodiments have been described herein, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A minimally-invasive surgical tool, comprising:
a tool shaft;
an end effector;
a multi-axial wrist disposed between the tool shaft and the end effector, the wrist comprising three or more sets of pulleys arranged in two orthogonal directions; and
a drive mechanism comprising a plurality of motors configured to effect movement of one or both of the wrist and the end effector by controlling four cable ends of a plurality of cables that wind at least partially around one or more of the three or more sets of pulleys, the drive mechanism configured to vary relative tension between the four cable ends to effect a yaw or pitch motion of the end effector,
wherein one of the motors is coupled to a rocker mechanism configured to rock back and forth so that a first end of the rocker mechanism moves proximally to thereby increase tension on one cable end coupled to the first end of the rocker mechanism, and a second opposite end of the rocker member moves distally to thereby relax tension on a second cable end coupled to the second end, to thereby effect the pitch motion of the end effector.

2. The surgical tool of claim 1, wherein the three or more sets of pulleys comprises two sets of pulleys oriented in two orthogonal directions and a third set of pulleys that are angled between said two sets of pulleys, thereby decreasing cross-over and friction between the cables.

3. The surgical tool of claim 1, wherein control of the cables controls movement of a pair of jaws of the end effector.

4. The surgical tool of claim 1, wherein the three or more sets of pulleys comprises a first set of pulleys attached to the end effector and a second set of pulleys aligned with the first set of pulleys such that part of one or more of the cables extends along a straight path from the second set of pulleys to the first set of pulleys.

5. The surgical tool of claim 4, wherein the first set of pulleys are arranged proximate a central axis of the tool shaft, the first set of pulleys having a diameter substantially equal to a diameter of the tool shaft.

6. The surgical tool of claim 1, wherein at least a portion of the motors are in a motor pack that is removably coupleable to a coupling unit attached to a proximal end of the tool shaft.

7. The surgical tool of claim 6, wherein the coupling unit provides a sterile barrier.

8. A minimally-invasive surgical tool, comprising:
a tool shaft;
an end effector;
a multi-axial wrist disposed between the tool shaft and the end effector, the wrist comprising three or more sets of pulleys arranged in two orthogonal directions; and
a drive mechanism comprising a plurality of motors configured to effect movement of one or both of the wrist and the end effector by controlling four cable ends of a plurality of cables that wind at least partially around one or more of the three or more sets of pulleys, the drive mechanism configured to vary relative tension between the four cable ends to effect a yaw or pitch motion of the end effector,
wherein one of the motors is coupled to a shuttle mechanism configured to move axially within the tool shaft, the shuttle mechanism configured to relax tension on one cable end and to increase tension on a second cable end to thereby effect a pitch motion of the end effector.

9. The surgical tool of claim 8, wherein the drive mechanism comprises three electric motors.

10. The surgical tool of claim 9, wherein at least a portion of the motors are in a motor pack that is removably coupleable to a coupling unit attached to a proximal end of the tool shaft.

11. The surgical tool of claim 10, wherein the coupling unit provides a sterile barrier.

12. The surgical tool of claim 8, wherein the three or more sets of pulleys comprises two sets of pulleys oriented in two orthogonal directions and a third set of pulleys that are angled between said two sets of pulleys, thereby decreasing cross-over and friction between the cables.

13. The surgical tool of claim 8, wherein control of the cables controls movement of a pair of jaws of the end effector.

14. The surgical tool of claim 8, wherein the three or more sets of pulleys comprises a first set of pulleys attached to the end effector and a second set of pulleys aligned with the first set of pulleys such that part of one or more of the cables extends along a straight path from the second set of pulleys to the first set of pulleys.

15. The surgical tool of claim 14, wherein the first set of pulleys are arranged proximate a central axis of the tool shaft, the first set of pulleys having a diameter substantially equal to a diameter of the tool shaft.

16. A minimally-invasive surgical tool, comprising:
a tool shaft;
an end effector;
a multi-axial wrist disposed between the tool shaft and the end effector, the wrist comprising three or more sets of pulleys arranged in two orthogonal directions; and
a drive mechanism comprising three electric motors configured to effect movement of one or both of the wrist and the end effector, the drive mechanism configured to independently control two cable loops that wind at least partially around one or more of the three or more sets of pulleys to vary relative tension between the two cable loops and between two ends of each cable loop to effect a yaw or pitch motion, one of the three motors coupled to a mechanism configured to tension two sides of the same cable loop to effect a pitch motion,
wherein said mechanism is a rocker mechanism configured to rock back and forth so that a first end of the rocker mechanism moves proximally, thereby increasing tension on a side of a cable coupled to the first end, and a second opposite end of the rocker member moves distally, thereby relaxing tension on an opposite side of the cable coupled to the second end, to thereby effect the pitch motion of the end effector.

17. A minimally-invasive surgical tool, comprising:

a tool shaft;

an end effector;

a multi-axial wrist disposed between the tool shaft and the end effector, the wrist comprising three or more sets of pulleys arranged in two orthogonal directions; and a drive mechanism comprising three electric motors configured to effect movement of one or both of the wrist and the end effector, the drive mechanism configured to independently control two cable loops that wind at least partially around one or more of the three or more sets of pulleys to vary relative tension between the two cable loops and between two ends of each cable loop to effect a yaw or pitch motion, one of the three motors coupled to a mechanism configured to tension two sides of the same cable loop to effect a pitch motion, wherein the mechanism is a shuttle mechanism configured to move axially within the tool shaft, the shuttle mechanism configured to relax tension on one of the two cable loops and to increase tension on another of the two cable loops to thereby effect the pitch motion of the end effector.

\* \* \* \* \*